US012575991B2

(12) United States Patent
Lim et al.

(10) Patent No.: US 12,575,991 B2
(45) Date of Patent: Mar. 17, 2026

(54) SURGICAL CART SUPPORTING ONE OR MORE SURGICAL ROBOTIC ARMS AND INTERFACE MOVEABLY INTERCONNECTING SURGICAL CART WITH SURGICAL TABLE

(71) Applicant: Warsaw Orthopedic, Inc., Warsaw, IN (US)

(72) Inventors: Roy K. Lim, Germantown, TN (US); Mark C. Dace, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 115 days.

(21) Appl. No.: 18/676,213

(22) Filed: May 28, 2024

(65) Prior Publication Data

US 2024/0398647 A1     Dec. 5, 2024

Related U.S. Application Data

(60) Provisional application No. 63/471,144, filed on Jun. 5, 2023.

(51) Int. Cl.
*A61G 13/10* (2006.01)
*A61B 34/30* (2016.01)
(Continued)

(52) U.S. Cl.
CPC ............ *A61G 13/101* (2013.01); *A61B 34/30* (2016.02); *A61B 50/13* (2016.02);
(Continued)

(58) Field of Classification Search
CPC .. A61G 13/101; A61G 13/0054; A61G 13/08; A61G 2200/325; A61G 13/04;
(Continued)

(56) References Cited

U.S. PATENT DOCUMENTS

| | | | |
|---|---|---|---|
| 2,691,979 | A | 10/1954 | Watson |
| 3,060,925 | A | 10/1962 | Honsaker et al. |

(Continued)

FOREIGN PATENT DOCUMENTS

| | | |
|---|---|---|
| EP | 3158986 | 4/2017 |
| EP | 3434248 | 1/2019 |

(Continued)

OTHER PUBLICATIONS

International Search Report and Written Opinion dated Sep. 11, 2024 in PCT/IB2024/055262.

*Primary Examiner* — Myles A Throop

(57) ABSTRACT

A surgical cart supporting one or more surgical robotic arms and an interface moveably interconnecting the surgical cart with a surgical table. The surgical cart can include a base portion, a first surgical robotic arm, and a second surgical robotic arm with end portions of the first surgical robotic arm and the second surgical robotic arm each capable of supporting surgical equipment thereon. The interface can including an extension portion attached relative to the surgical cart, a collar portion moveably attached relative to a longitudinal cross-member of the surgical table, a receiver portion provided on the collar portion and an actuator portion actuatable to facilitate movement of the collar portion relative to the longitudinal cross member. When an end portion of the extension portion is received in a recess provided on the collar portion, a locking member be engaged to attach the extension portion and the collar portion to one another. After attachment of the extension portion and the collar portion, the surgical cart can be moved relative to the surgical table via actuation of the actuator portion.

20 Claims, 39 Drawing Sheets

(51) Int. Cl.
    *A61B 50/13*        (2016.01)
    *A61G 13/00*        (2006.01)
    *A61G 13/08*        (2006.01)

(52) U.S. Cl.
    CPC .......... *A61G 13/0054* (2016.11); *A61G 13/08*
        (2013.01); *A61G 2200/325* (2013.01)

(58) Field of Classification Search
    CPC .. A61G 13/06; A61G 2210/50; A61G 13/104;
            A61G 13/121; A61G 13/122; A61G
            13/123; A61G 13/1245; A61B 34/30;
                A61B 50/13; A61B 2034/304
    See application file for complete search history.

(56)              References Cited

U.S. PATENT DOCUMENTS

| | | | |
|---|---|---|---|
| 3,227,440 A | 1/1966 | Scott | |
| 3,293,667 A | 12/1966 | Ohrberg | |
| 3,306,287 A | 2/1967 | Arp | |
| 3,389,702 A | 6/1968 | Kennedy | |
| 3,745,996 A | 7/1973 | Rush | |
| 3,828,377 A | 8/1974 | Fary, Sr. | |
| 4,029,089 A | 6/1977 | Mulhlland | |
| 4,194,257 A | 3/1980 | Martin et al. | |
| 4,627,119 A | 12/1986 | Hachey et al. | |
| 4,655,200 A | 4/1987 | Knight | |
| 4,705,026 A | 11/1987 | Chaussy | |
| 4,866,796 A | 9/1989 | Robinson | |
| 4,872,656 A | 10/1989 | Brendgord | |
| 4,901,384 A | 2/1990 | Eary | |
| 4,915,101 A | 4/1990 | Cuccia | |
| 5,009,407 A | 4/1991 | Watanabe | |
| 5,013,018 A | 5/1991 | Sicek | |
| 5,088,706 A | 2/1992 | Jackson | |
| 5,103,511 A | 4/1992 | Sequin | |
| 5,131,106 A | 7/1992 | Jackson | |
| 5,362,302 A | 11/1994 | Jenson et al. | |
| 5,390,383 A | 2/1995 | Carn | |
| 5,410,769 A | 5/1995 | Waterman | |
| 5,444,882 A | 8/1995 | Andrews | |
| 5,613,254 A * | 3/1997 | Clayman | A61G 13/12 |
| | | | 5/613 |
| 5,642,302 A | 6/1997 | Dumont | |
| 5,860,899 A | 1/1999 | Rassman | |
| 5,991,651 A | 11/1999 | LaBarbera | |
| 6,003,176 A | 12/1999 | Wasley | |
| 6,076,525 A | 6/2000 | Hoffman | |
| 6,112,349 A | 9/2000 | Connolly | |
| 6,154,901 A | 12/2000 | Carr | |
| 6,260,220 B1 | 7/2001 | Lamb | |
| 6,295,671 B1 | 10/2001 | Reesby et al. | |
| 6,311,349 B1 | 11/2001 | Kazakia | |
| 6,367,104 B1 | 4/2002 | Fallbo, Sr. et al. | |
| 6,378,149 B1 | 4/2002 | Sanders et al. | |
| 6,516,483 B1 | 2/2003 | VanSteenburg | |
| 6,566,833 B2 | 5/2003 | Barlett | |
| 6,615,430 B2 | 9/2003 | Heimbrock | |
| 6,671,905 B2 | 1/2004 | Bartlett et al. | |
| 6,681,423 B2 | 1/2004 | Zachrisson | |
| 6,701,553 B1 | 3/2004 | Hand et al. | |
| 6,701,554 B2 | 3/2004 | Heimbrock | |
| 6,701,558 B2 | 3/2004 | VanSteenburg | |
| 6,715,169 B2 | 4/2004 | Niederkrom | |
| 6,728,983 B2 | 5/2004 | Bartlett et al. | |
| 6,732,390 B2 | 5/2004 | Krywiczanin | |
| 6,739,006 B2 | 5/2004 | Borders et al. | |
| 6,820,621 B2 | 11/2004 | DeMayo | |
| 6,874,181 B1 | 4/2005 | Connolly et al. | |
| 6,934,986 B2 | 8/2005 | Krywiczanin et al. | |
| 6,941,951 B2 | 9/2005 | Hubert et al. | |
| 6,966,081 B1 | 11/2005 | Sharps | |
| 7,100,225 B1 | 9/2006 | Bailey | |
| 7,152,261 B2 | 12/2006 | Jackson | |
| 7,189,214 B1 | 3/2007 | Saunders | |
| 7,219,379 B2 | 5/2007 | Krywiczanin et al. | |
| 7,234,180 B2 | 6/2007 | Horton et al. | |
| 7,290,302 B2 | 11/2007 | Sharps | |
| 7,343,635 B2 | 3/2008 | Jackson | |
| 7,426,930 B1 | 9/2008 | Bailey | |
| 7,472,440 B2 | 1/2009 | Bartlett et al. | |
| 7,484,253 B1 | 2/2009 | Coppens | |
| 7,496,980 B2 | 3/2009 | Sharps | |
| 7,565,708 B2 | 7/2009 | Jackson | |
| 7,600,281 B2 | 10/2009 | Skripps | |
| 7,603,790 B2 | 10/2009 | Jordan et al. | |
| 7,669,262 B2 | 3/2010 | Skripps | |
| 7,739,762 B2 | 6/2010 | Lamb et al. | |
| 7,882,583 B2 | 2/2011 | Skripps | |
| 8,060,960 B2 | 11/2011 | Jackson | |
| 8,118,029 B2 | 2/2012 | Gneiting et al. | |
| 8,234,730 B2 | 8/2012 | Skripps | |
| 8,286,283 B2 | 10/2012 | Copeland et al. | |
| 8,286,637 B2 | 10/2012 | Kaska | |
| 8,381,331 B2 | 2/2013 | Sharps et al. | |
| 8,381,335 B2 | 2/2013 | Ahlman | |
| 8,413,660 B2 | 4/2013 | Weinstein et al. | |
| 8,439,948 B1 | 5/2013 | King | |
| 8,443,473 B2 | 5/2013 | Maxwell | |
| 8,584,281 B2 | 11/2013 | Diel et al. | |
| 8,635,725 B2 | 1/2014 | Tannoury et al. | |
| 8,677,529 B2 | 3/2014 | Jackson | |
| 8,707,484 B2 | 4/2014 | Jackson et al. | |
| 8,978,180 B2 | 3/2015 | Jackson | |
| 9,072,646 B2 | 7/2015 | Skripps et al. | |
| 9,180,062 B2 | 11/2015 | Jackson | |
| 9,186,291 B2 | 11/2015 | Jackson et al. | |
| 9,226,865 B2 | 1/2016 | Jackson et al. | |
| 9,265,680 B2 | 2/2016 | Sharps | |
| 9,295,433 B2 | 3/2016 | Jackson et al. | |
| 9,308,145 B2 | 4/2016 | Jackson | |
| 9,339,430 B2 | 5/2016 | Jackson et al. | |
| 9,358,170 B2 | 6/2016 | Jackson | |
| 9,402,775 B2 | 8/2016 | Jackson et al. | |
| 9,414,982 B2 | 8/2016 | Jackson | |
| 9,468,576 B2 | 10/2016 | Jackson | |
| 9,498,397 B2 | 11/2016 | Hight et al. | |
| 9,522,078 B2 | 12/2016 | Pizzini | |
| 9,554,959 B2 | 1/2017 | Carn | |
| 9,622,928 B2 | 4/2017 | Jackson et al. | |
| 9,642,760 B2 | 5/2017 | Jackson et al. | |
| 9,655,793 B2 | 5/2017 | Hertz | |
| 9,700,476 B2 | 7/2017 | Hoel et al. | |
| 9,713,562 B2 | 7/2017 | Perlman et al. | |
| 9,744,089 B2 | 8/2017 | Jackson | |
| 9,849,054 B2 | 12/2017 | Jackson | |
| 9,937,006 B2 | 4/2018 | Skripps et al. | |
| 9,993,380 B2 | 6/2018 | Jackson | |
| 10,136,863 B2 | 11/2018 | Kaiser et al. | |
| 10,314,758 B2 | 6/2019 | Dolliver et al. | |
| 10,342,722 B2 | 7/2019 | Garrido | |
| 10,406,054 B1 | 9/2019 | Scholl et al. | |
| 10,426,684 B2 | 10/2019 | Dubois et al. | |
| 10,531,998 B2 | 1/2020 | Jackson et al. | |
| 10,543,142 B2 | 1/2020 | Lim et al. | |
| 10,548,796 B2 | 2/2020 | Lim et al. | |
| 10,576,006 B2 | 3/2020 | Lim et al. | |
| 10,695,252 B2 | 6/2020 | Jackson | |
| 10,722,413 B2 | 7/2020 | Lim et al. | |
| 10,729,607 B2 | 8/2020 | Jackson | |
| 10,751,240 B2 | 8/2020 | Lim et al. | |
| 10,835,438 B2 | 11/2020 | Jackson | |
| 10,835,439 B2 * | 11/2020 | Lim | A61G 13/08 |
| 10,849,809 B2 | 12/2020 | Lim et al. | |
| 10,874,570 B2 | 12/2020 | Lim et al. | |
| 10,888,484 B2 | 1/2021 | Lim et al. | |
| 10,893,996 B2 | 1/2021 | Lim et al. | |
| 10,898,401 B2 | 1/2021 | Lim et al. | |
| 10,900,448 B2 | 1/2021 | Lim et al. | |
| 12,213,905 B2 * | 2/2025 | Lim | A61G 13/10 |
| 2002/0138905 A1 | 10/2002 | Barltett et al. | |
| 2002/0138906 A1 | 10/2002 | Barltett et al. | |
| 2002/0157186 A1 | 10/2002 | VanSteenburg | |
| 2003/0140419 A1 | 7/2003 | Barltett et al. | |

(56) References Cited

U.S. PATENT DOCUMENTS

| | | | |
|---|---|---|---|
| 2003/0140420 A1 | 7/2003 | Niederkrom | |
| 2003/0145382 A1 | 8/2003 | Krywiczanin | |
| 2003/0178027 A1 | 9/2003 | DeMayo et al. | |
| 2004/0010849 A1 | 1/2004 | Krywiczanin et al. | |
| 2004/0133979 A1 | 7/2004 | Newkirk et al. | |
| 2004/0133983 A1 | 7/2004 | Newkirk | |
| 2005/0181917 A1 | 8/2005 | Dayal | |
| 2006/0037141 A1 | 2/2006 | Krywiczanin et al. | |
| 2006/0123546 A1 | 6/2006 | Horton | |
| 2006/0162076 A1 | 7/2006 | Bartlett et al. | |
| 2006/0162084 A1 | 7/2006 | Mezue | |
| 2006/0185090 A1 | 8/2006 | Jackson | |
| 2008/0034502 A1 | 2/2008 | Copeland et al. | |
| 2008/0134434 A1 | 6/2008 | Celauro | |
| 2008/0222811 A1 | 9/2008 | Gilbert et al. | |
| 2009/0070936 A1 | 3/2009 | Henderson | |
| 2009/0139030 A1 | 6/2009 | Yang | |
| 2009/0248041 A1 | 10/2009 | Williams et al. | |
| 2010/0037397 A1 | 2/2010 | Wood | |
| 2010/0192300 A1 | 8/2010 | Tannoury | |
| 2010/0293713 A1* | 11/2010 | Sharps | A61G 13/06 |
| | | | 5/83.1 |
| 2010/0293719 A1 | 11/2010 | Klemm et al. | |
| 2011/0030702 A1 | 2/2011 | Czajka, Jr. | |
| 2011/0099716 A1 | 5/2011 | Jackson | |
| 2012/0103344 A1 | 5/2012 | Hunter | |
| 2012/0144589 A1 | 6/2012 | Skripps et al. | |
| 2012/0255122 A1 | 10/2012 | Diel et al. | |
| 2013/0111666 A1 | 5/2013 | Jackson | |
| 2013/0191994 A1 | 8/2013 | Bellows et al. | |
| 2013/0247921 A1 | 9/2013 | Dye | |
| 2013/0283526 A1 | 10/2013 | Gagliardi | |
| 2013/0307298 A1 | 11/2013 | Meiki | |
| 2014/0020183 A1 | 1/2014 | Dominick | |
| 2014/0059773 A1 | 3/2014 | Carn | |
| 2014/0068861 A1 | 3/2014 | Jackson | |
| 2014/0109316 A1 | 4/2014 | Jackson et al. | |
| 2014/0130258 A1* | 5/2014 | Kobuss | B62B 3/008 |
| | | | 280/79.3 |
| 2014/0137327 A1 | 5/2014 | Tannoury et al. | |
| 2015/0038982 A1 | 2/2015 | Kilroy et al. | |
| 2015/0044956 A1 | 2/2015 | Hacker | |
| 2015/0245969 A1 | 9/2015 | Hight et al. | |
| 2015/0245971 A1 | 9/2015 | Bernardoni et al. | |
| 2015/0272681 A1 | 10/2015 | Skripps et al. | |
| 2016/0000621 A1 | 1/2016 | Jackson | |
| 2016/0047394 A1 | 2/2016 | Lee et al. | |
| 2016/0081582 A1 | 3/2016 | Rapoport | |
| 2016/0089287 A1 | 3/2016 | Buerstner | |
| 2016/0193099 A1 | 7/2016 | Drake | |
| 2016/0317373 A1 | 11/2016 | Jackson et al. | |
| 2016/0331477 A1 | 11/2016 | Yu et al. | |
| 2017/0027797 A1 | 2/2017 | Dolliver et al. | |
| 2017/0049651 A1 | 2/2017 | Lim | |
| 2017/0049653 A1 | 2/2017 | Lim | |
| 2017/0079864 A1 | 3/2017 | Riley | |

| | | | |
|---|---|---|---|
| 2017/0112698 A1 | 4/2017 | Hight et al. | |
| 2017/0135891 A1 | 5/2017 | Kettner | |
| 2017/0151115 A1 | 6/2017 | Jackson | |
| 2017/0341232 A1 | 11/2017 | Perplies | |
| 2017/0348171 A1 | 12/2017 | Jackson | |
| 2018/0116891 A1 | 5/2018 | Beale et al. | |
| 2018/0185106 A1* | 7/2018 | Itkowitz | A61B 90/35 |
| 2018/0185228 A1 | 7/2018 | Catacchio et al. | |
| 2018/0193104 A1 | 7/2018 | Beale et al. | |
| 2018/0207044 A1* | 7/2018 | Sabet | A61G 13/105 |
| 2018/0222044 A1 | 8/2018 | Guerrera et al. | |
| 2018/0344421 A1 | 12/2018 | Gagle et al. | |
| 2018/0363596 A1 | 12/2018 | Lim et al. | |
| 2019/0000702 A1 | 1/2019 | Lim et al. | |
| 2019/0000707 A1* | 1/2019 | Lim | A61G 13/1295 |
| 2019/0046381 A1 | 2/2019 | Lim et al. | |
| 2019/0046383 A1 | 2/2019 | Lim et al. | |
| 2019/0209409 A1 | 7/2019 | Jackson et al. | |
| 2019/0374420 A1 | 12/2019 | Lehman | |
| 2020/0000668 A1 | 1/2020 | Lim et al. | |
| 2020/0060913 A1 | 2/2020 | Lim et al. | |
| 2020/0060914 A1 | 2/2020 | Lim et al. | |
| 2020/0060915 A1 | 2/2020 | Lim et al. | |
| 2020/0138659 A1 | 5/2020 | Lim et al. | |
| 2020/0138660 A1 | 5/2020 | Jackson | |
| 2020/0170868 A1 | 6/2020 | Jackson | |
| 2020/0188208 A1 | 6/2020 | Lim et al. | |
| 2020/0281788 A1 | 9/2020 | Lim et al. | |
| 2020/0297568 A1 | 9/2020 | Lim et al. | |
| 2020/0337923 A1 | 10/2020 | Lim et al. | |
| 2020/0337926 A1 | 10/2020 | Lim et al. | |
| 2020/0337927 A1 | 10/2020 | Lim et al. | |
| 2020/0360214 A1 | 11/2020 | Lim et al. | |
| 2022/0008016 A1 | 1/2022 | Harrison et al. | |
| 2022/0409311 A1 | 12/2022 | Tadano et al. | |
| 2023/0147674 A1 | 5/2023 | Mirbagheri et al. | |
| 2023/0301862 A1 | 9/2023 | Lim et al. | |
| 2023/0310109 A1* | 10/2023 | Timm | B25J 9/0009 |
| | | | 248/645 |
| 2023/0363715 A1* | 11/2023 | Lim | A61G 13/06 |
| 2023/0363936 A1 | 11/2023 | Lim et al. | |
| 2023/0363969 A1 | 11/2023 | Lim et al. | |
| 2023/0414431 A1* | 12/2023 | Lim | A61G 13/08 |
| 2024/0065912 A1 | 2/2024 | Lim et al. | |
| 2024/0382362 A1* | 11/2024 | Lim | A61G 13/10 |
| 2024/0390206 A1 | 11/2024 | Lim et al. | |

FOREIGN PATENT DOCUMENTS

| | | |
|---|---|---|
| EP | 3909539 | 11/2021 |
| JP | 2018069048 | 5/2018 |
| JP | 6449958 | 12/2018 |
| WO | WO0062731 | 10/2000 |
| WO | 2007058673 | 5/2007 |
| WO | 2017031225 | 2/2017 |
| WO | 2019067028 | 4/2019 |
| WO | 2021176531 | 9/2021 |

* cited by examiner

SURGICAL CART SUPPORTING ONE OR MORE SURGICAL ROBOTIC ARMS AND INTERFACE MOVEABLY INTERCONNECTING SURGICAL CART WITH SURGICAL TABLE

CROSS-REFERENCE TO RELATED APPLICATION

This application claims the benefit of and priority to U.S. Provisional Patent Application No. 63/471,144 filed Jun. 5, 2023, the entire disclosure of which is incorporated by reference herein.

FIELD

The present technology generally relates to a surgical cart for supporting one or more surgical robotic arms and an interface for moveably interconnecting the surgical cart with a surgical table, where the surgical cart moves relative to the surgical table using the interface, and the one or more surgical robotic arms can manipulate surgical equipment supported thereby relative to the patient supported by the surgical table to aid and/or perform surgery on the patient.

BACKGROUND

Use of imaging systems and conventional surgical robots and robotic systems during surgery has become common. Such imaging systems and conventional surgical robots and robotic systems are typically separate from conventional surgical tables supporting patients, and the base portions thereof are typically positionable adjacent the head, the feet, or the lateral sides of the patients and corresponding portions of the surgical tables. Movement of the imaging systems and conventional surgical robots and robotic systems is typically independent of and not coordinated with movement of the conventional surgical tables. To illustrate, the base portions of the imaging systems and conventional surgical robots and robotic systems typically can be positioned and repositioned on the ground relative to the surgical tables and the patients supported thereby, and various portions of the imaging systems and various arms of the surgical robots and robotic systems typically can be positioned and repositioned relative to the surgical tables and the patients supported thereby. And the surgical tables typically can be positioned and repositioned on the ground relative to the imaging systems and surgical robot and robotic systems, and the conventional surgical tables typically can be adjusted/articulated to adjust/articulate the positions of the patients supported thereby. However, the imaging systems and conventional surgical robots and robotic systems do not control movement of the conventional surgical tables, and vice versa. As such, coordinated movement between the imaging systems and conventional surgical robots and robotics systems, and the conventional surgical tables can be very difficult.

Therefore, there is a need for a surgical cart and an interface for moveably interconnecting the surgical cart and a surgical table relative to one another, where the surgical cart can support one or more surgical robotic arms thereon, and the interface can move the surgical cart relative to the surgical table relative in at least a cranial-caudal direction of a patient supported by the surgical table. Portions of the interface can be incorporated on the cart and the surgical table, and these portions can be used to move the surgical cart and the one or more surgical robotic arms supported thereby relative to patient supported by the surgical table.

The one or more surgical robotic arms can support surgical equipment such as an imaging system thereon, and manipulation of the surgical robotic arms to position and reposition portions of the imaging system relative to the patient, along with movement afforded by the interface, can facilitate generation of 2D and/or 3D imagery using the imaging system.

SUMMARY

The techniques of this disclosure generally relate to a surgical cart for supporting one or more surgical robotic arms and an interface for moveably interconnecting the surgical cart with a surgical table, where the surgical table can be moved relative to the surgical table using the interface, and the one or more surgical robotic arms can be used to manipulate equipment supported thereby relative to the patient supported by the surgical table to aid and/or perform surgery one the patient.

In one aspect, the present disclosure provides a combination of a surgical table, a surgical cart supporting at least two surgical robotic arms, and an interface for moveably interconnecting the surgical cart with the surgical table, the combination including the surgical table comprising a first end, an opposite second end, a longitudinal cross-member extending between the first end and the second end, at least one track attached to the longitudinal cross-member, and at least one patient support portion being configured to rotatably support a patient thereon; the surgical cart including a base portion having at least an upper portion and a side portion; and a first surgical robotic arm and a second surgical robotic arm of the at least two surgical robotic arms supported by the base portion, the first surgical robotic arm supported relative to the upper portion, and the second surgical robotic arm supported relative to the side portion, the first surgical robotic arm including at least an end portion, and the second surgical robotic arm including a first arm portion, a second arm portion, and an end portion, the first arm portion and the second arm portion each including a first end and a second end, the first end of the first arm portion being pivotally attached relative to the to the side portion, the second end of the first arm portion and the first end of the second arm portion being pivotally attached to one another, and the second end of the second arm portion supporting the end portion of the second surgical robotic arm, the end portions of the first surgical robotic arm and the second surgical robotic arm each supporting surgical equipment thereon; and the interface including an extension portion attached relative to the surgical cart, the extension portion including an end portion and a receiving aperture formed in the end portion, and the extension portion being moveable outwardly and inwardly relative to the surgical cart; a receiver portion provided on the collar portion, the receiver portion including a recess and a locking member moveable into and out of the recess, and the recess being configured to receive the end portion of the extension portion, and the locking member configured to be moved into and out of the receiving aperture; a collar portion moveably attached relative to the longitudinal cross-member of the surgical table, the collar portion including a first end, an opposite second end, an interior cavity extending between the first end and the second end, an interior surface defining a portion of the interior cavity, and at least one truck attached relative to the interior surface; and an actuator portion actuatable to facilitate movement of the at least one truck along the at least one track; where portions of the longitudinal cross member of the surgical table are received in the interior cavity to attach the collar portion to the surgical table with the at least one truck being engaged to at least one track portion attached to the longitudinal cross member; where, when the end portion of the extension portion is received in the recess, the locking member can be received in the receiving aperture to attach the extension portion and the collar portion to one another, and after attachment of the extension portion and the collar portion, the surgical cart is moveably interconnected to the surgical table via actuation of the actuator portion; and where the first surgical robotic arm and the second surgical robotic arm can be manipulated to position and reposition the surgical equipment thereon relative to the patient supported by the surgical table.

In another aspect, the present disclosure provides a combination of a surgical table, a surgical cart supporting at least two surgical robotic arms, and an interface for moveably interconnecting the surgical cart with the surgical table, the combination including the surgical table comprising a first end, an opposite second end, a longitudinal cross-member extending between the first end and the second end, and at least one patient support portion being configured to support a patient thereon; the surgical cart including a base portion; and a first surgical robotic arm and a second surgical robotic arm of the at least two surgical robotic arms supported by the base portion, the first surgical robotic arm including at least an end portion, and the second surgical robotic arm including a first arm portion, a second arm portion, and an end portion, the first arm portion and the second arm portion each including a first end and a second end, the first end of the first arm portion being pivotally attached relative to the to the side portion, the second end of the first arm portion and the first end of the second arm portion being pivotally attached to one another, and the second end of the second arm portion supporting the end portion of the second surgical robotic arm, the end portions of the first surgical robotic arm and the second surgical robotic arm each supporting surgical equipment thereon; and the interface including an extension portion attached relative to the surgical cart, the extension portion including an end portion and a receiving aperture formed in the end portion; a collar portion moveably attached relative to the longitudinal cross-member of the surgical table, the collar portion including a first end, an opposite second end, an interior cavity extending between the first end and the second end, an interior surface defining a portion of the interior cavity; a receiver portion provided on the collar portion, the receiver portion including a recess and a locking member moveable into and out of the recess, and the recess being configured to receive the end portion of the extension portion, and the locking member configured to be moved into and out of the receiving aperture; and an actuator portion actuatable to facilitate movement of the collar portion relative to the longitudinal cross member; where portions of the longitudinal cross member of the surgical table are received in the interior cavity to attach the collar portion to the surgical table; where, when the end portion of the extension portion is received in the recess, the locking member can be received in the receiving aperture to attach the extension portion and the collar portion to one another, and after attachment of the extension portion and the collar portion, the surgical cart is moveably interconnected to the surgical table via actuation of the actuator portion; and where the first surgical robotic arm and the second surgical robotic arm can be manipulated to position and reposition the surgical equipment thereon relative to the patient supported by the surgical table.

In yet another aspect, the present disclosure provides a combination of a surgical table, a surgical cart supporting at least two surgical robotic arms, and an interface for moveably interconnecting the surgical cart with the surgical table, the combination including the surgical table comprising a first end, an opposite second end, a longitudinal cross-member extending between the first end and the second end, and at least one patient support portion being configured to support a patient thereon; the surgical cart including a base portion; and a first surgical robotic arm and a second surgical robotic arm of the at least two surgical robotic arms supported by the base portion, the first surgical robotic arm including at least an end portion, and the second surgical robotic arm including a first arm portion, a second arm portion, and an end portion, the first arm portion and the second arm portion each including a first end and a second end, the first end of the first arm portion being pivotally attached relative to the to the side portion, the second end of the first arm portion and the first end of the second arm portion being pivotally attached to one another, and the second end of the second arm portion supporting the end portion of the second surgical robotic arm, the end portions of the first surgical robotic arm and the second surgical robotic arm each supporting surgical equipment thereon; and the interface including an extension portion attached relative to the surgical cart, the extension portion including an end portion and a receiving aperture formed in the end portion; a collar portion moveably attached relative to the longitudinal cross-member of the surgical table; a receiver portion provided on the collar portion, the receiver portion including a recess and a locking member moveable into and out of the recess, and the recess being configured to receive the end portion of the extension portion, and the locking member configured to be moved into and out of the receiving aperture; and an actuator portion actuatable to facilitate movement of the collar portion relative to the longitudinal cross member; where, when the end portion of the extension portion is received in the recess, the locking member can be received in the receiving aperture to attach the extension portion and the collar portion to one another, and after attachment of the extension portion and the collar portion, the surgical cart is moveably interconnected to the surgical table via actuation of the actuator portion; and where the first surgical robotic arm and the second surgical robotic arm can be manipulated to position and reposition the surgical equipment thereon relative to the patient supported by the surgical table.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

The techniques of this disclosure generally relate to an interface for moveably interconnecting a surgical table and a cart portion supporting an imaging device and/or a surgical robotic system relative to one another.

DETAILED DESCRIPTION

Figure 1A:
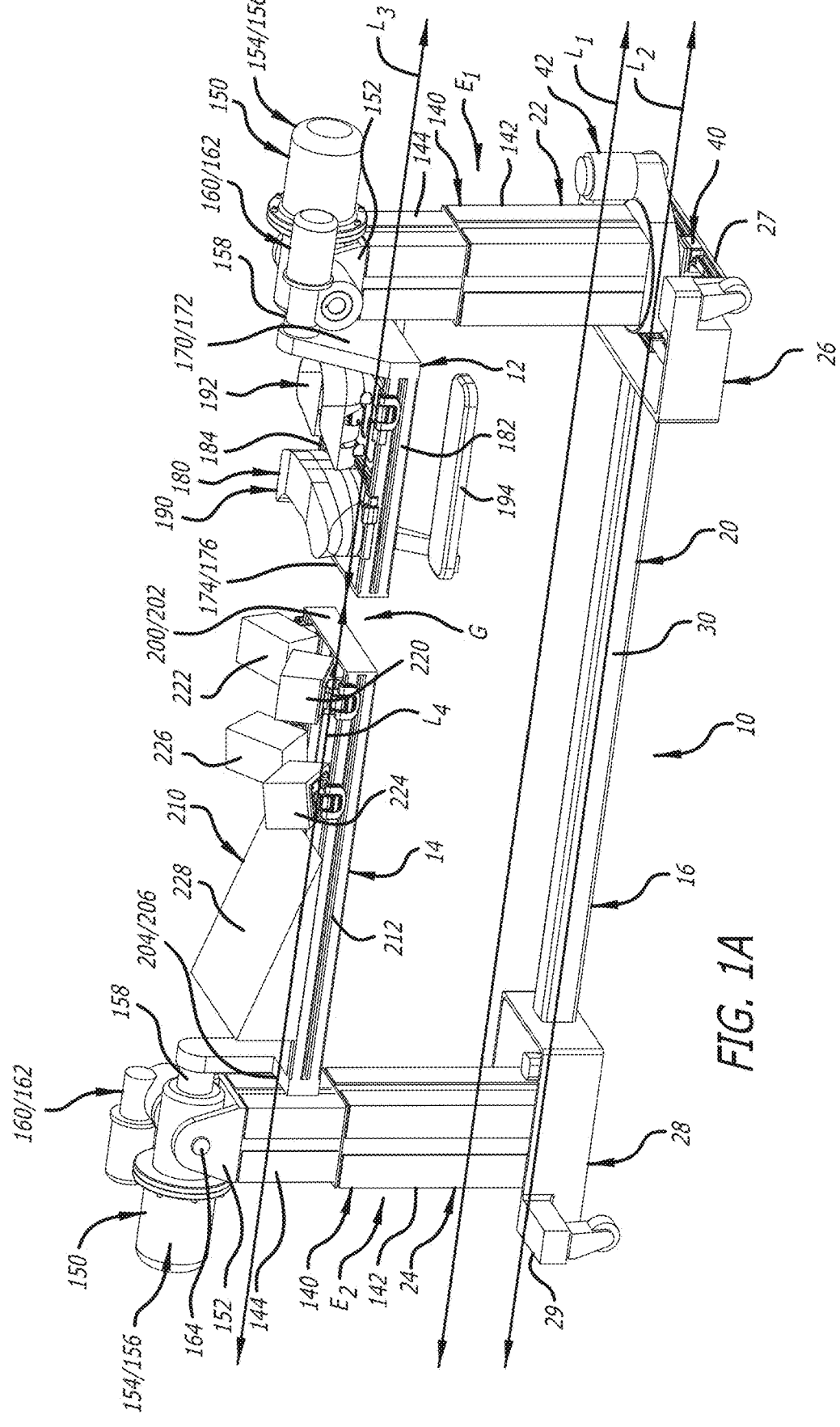
FIG. 1A is a side, perspective view that illustrates a surgical table of the present disclosure.

FIGS. 1-12 depict a prior art embodiment of a surgical table generally indicated by the numeral 10. FIGS. 1-12 were previously described in U.S. Ser. No. 17/741,125, filed May 10, 2022, which is hereby incorporated by reference herein in its entirety.

The surgical table 10 includes a first end E1, a second end E2, and a mid-longitudinal L1 extending through the first end E1 and the second end E2. The surgical table 10 includes a first platform portion 12, a second platform portion, 14 and a support portion 16. The support portion 16 supports the first platform portion 12 and the second platform portion 14 above the ground, and the first platform portion 12 and the second platform portion 14 can each support a portion of a patient P thereon.

The first platform portion 12 and the second platform portion 14, as depicted in FIGS. 1A-1C and 6-12, are spaced apart from another across a gap G, and can be independently positioned/oriented and repositioned/reoriented relative to one another. Together, when the patient is supported thereby, adjustment of the first platform portion 12 and the second platform portion 14 relative to one another can be used to manipulate and provide access to the spine of the patient. The manipulation of the patient P and the access afforded by the gap G can aid the performance of surgery on the patient P, and such surgery, for example, can include spinal surgery on the spine of the patient.

The support portion 16, as depicted in FIGS. 1A and 6-12, includes a horizontally-oriented portion 20, a first vertically-oriented portion 22, and a second vertically-oriented portion 24. The horizontally-oriented portion 20 is used in supporting the first vertically-oriented portion 22 and the second vertically-oriented portion 24 relative to the ground, the first vertically-oriented portion 22 is used in supporting the first platform portion 12 relative to the horizontally-oriented portion 20, and the second vertically-oriented portion 24 is used in supporting the second platform portion 14 relative to the horizontally-oriented portion 20. The surgical table 10, as discussed below, can include a controller or controllers for controlling motorized actuators included in the surgical table 10 to facilitate the operation thereof.

As depicted in FIG. 1A, the horizontally-oriented portion 20 includes a first end portion 26 at a first end 27 thereof (collocated with the first end E1), a second end portion 28 at a second end 29 thereof (collocated with the second end E2), and a cross member 30 extending between the first end portion 26 and the second end portion 26. The cross member 30 can be aligned with a mid-longitudinal axis L2 of the horizontally-oriented portion 20, can be used to connect the first end portion 26 and the second end portion 28, and can be expandable and contractable to expand and contract a length of the horizontally-oriented portion 20 along the mid-longitudinal axis L2.

Figure 2:
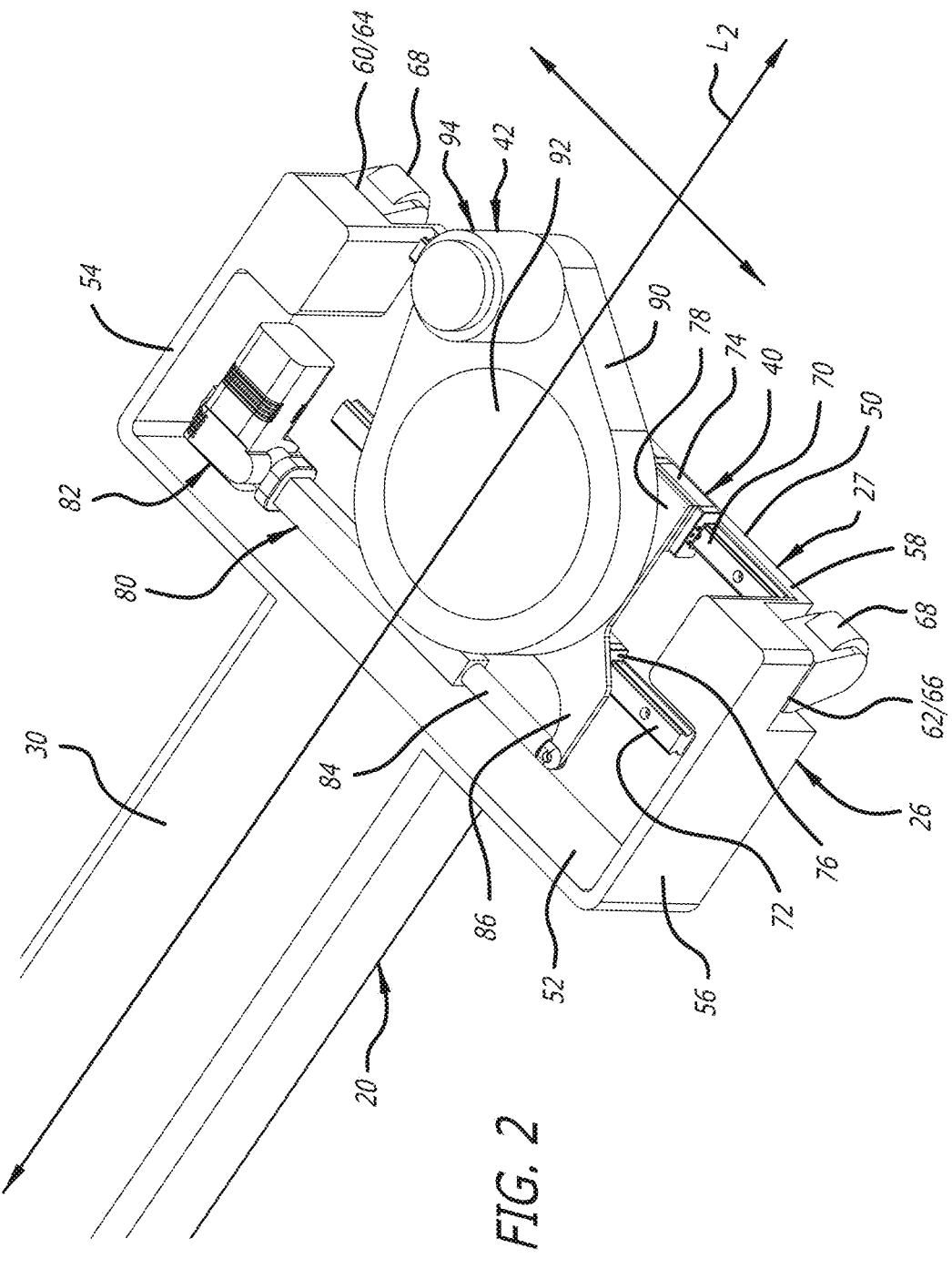
FIG. 2 is a top, perspective view that illustrates a slider portion and a rotatable portion of a first end portion of the surgical table of FIG. 1A.
Figure 3:
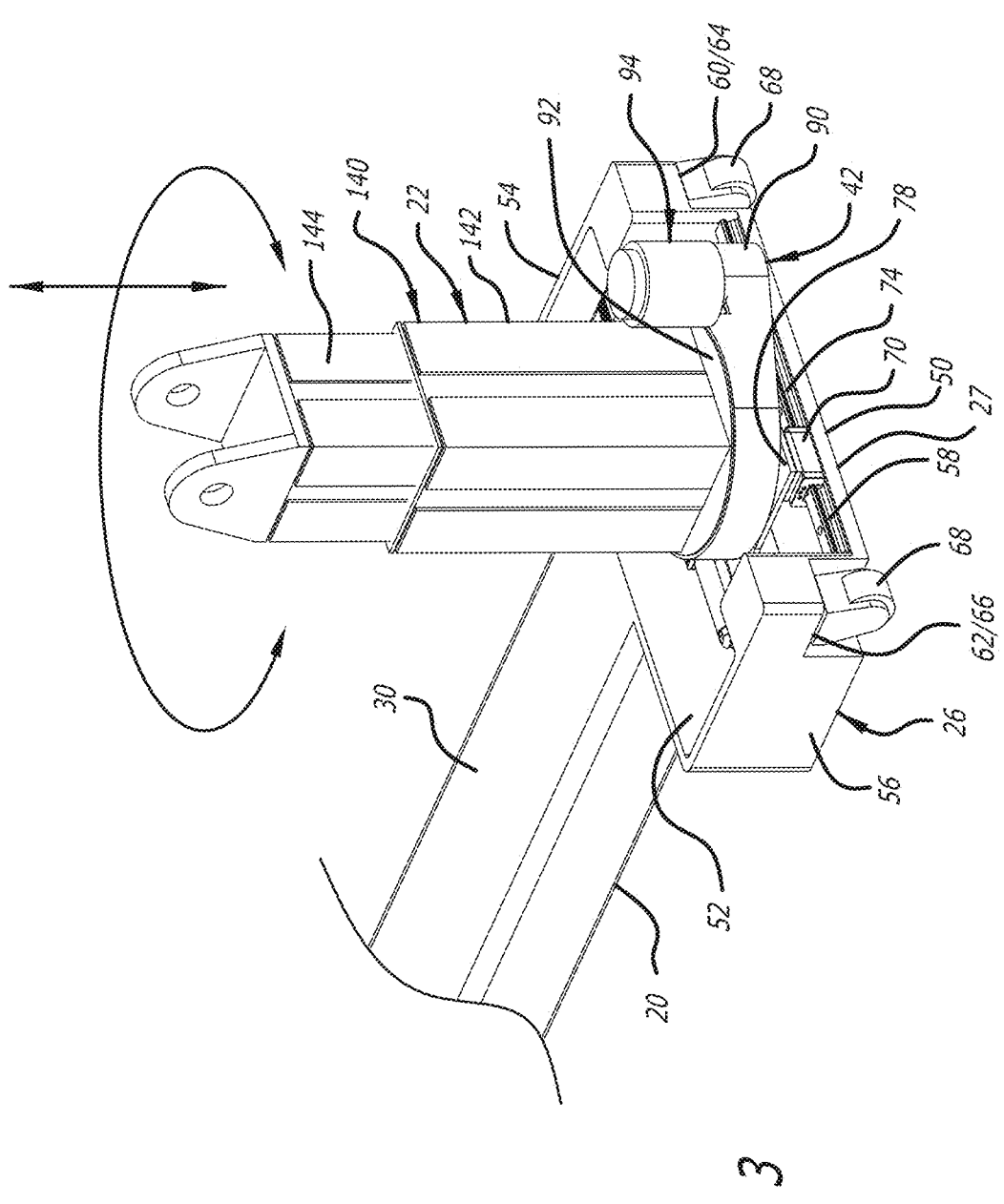
FIG. 3 is an end, perspective view that illustrates the slider portion and the rotatable portion of the first end portion supporting a first vertically-oriented portion of the surgical table of FIG. 1A.

The first end portion 26, as depicted in FIGS. 2 and 3, supports the first vertically-oriented portion 22, and includes a slider portion 40 and a rotator portion 42. As discussed below, the slider portion 40 is configured to move the first vertically-oriented portion 22 in directions transverse to the mid-longitudinal axes L1 and L2, and the rotator portion 42 is configured to rotate the first vertically-oriented portion 22 about a vertically-oriented axis. As depicted in FIGS. 2 and 3, the first end portion 26 includes a bottom portion 50, an endwall portion 52, a first sidewall portion 54, and a second sidewall portion 56.

The first end portion 26 includes an open end 58 adjacent the first end 27, and together, the bottom portion 50, the endwall portion 52, the first sidewall portion 54, and the second sidewall portion 56 define an area in which the slider portion 40 and the rotator portion 42 are provided. Furthermore, the first sidewall portion 54 and the second sidewall portion 56 include indentations 60 and 62 that include undersurfaces 64 and 66, respectively. Casters 68 can be attached to each of the undersurfaces 64 and 66, and together with other casters, the casters 68 can be used to space the support portion 16 from the ground and to facilitate movement of the support portion 16.

The slider portion 40, as depicted in FIGS. 2 and 3, includes a first track portion 70, a second track portion 72, first trucks 74 moveable along the first track portion 70, second trucks 76 moveable along the second track portion 72, and a platform portion 78 supported by the first trucks 74 and the second trucks 76. Using movement of the first trucks 74 and the second trucks 76 on the first track portion 70 and the second track portion 72, respectively, the platform portion 78 is moveable relative to the bottom portion 50 in side-to-side directions transverse to the mid-longitudinal axes L1 and L2 between a first position and a second position. In the first position, a majority of the platform portion 78 is located on one side of the mid-longitudinal axis L2, and, in the second position, a majority of the platform portion 78 is located on the other side of the mid-longitudinal axis L2.

Linear movement of the platform portion 78 can be controlled via operation of an actuator 80 that includes a motor and transmission portion 82 that is actuatable to move a telescoping arm portion 84 inwardly and outwardly. The telescoping arm portion 84 is attached to an extension portion 86 that extends outwardly from the platform portion 78. As such, the inward movement and the outward movement of the telescoping arm portion 84 serves to move the platform portion 78 (and the first vertically-oriented portion 22 supported thereby) between the first position and the second position thereof. As such, the first platform portion 12 supported by the first vertically-oriented portion 22 can be moved in side-to-side directions relative to the mid-longitudinal axes L1 and L2 via actuation of the actuator 80 of the slider portion 40. Furthermore, the operation of the slider portion 40 and the actuator 80 thereof can be controlled by the controllers of the surgical table 10.

As depicted in FIG. 3, the platform portion 78 can support the rotator portion 42 thereon, and the rotator portion 42 can support the first vertically-oriented portion 22 thereon. The rotator portion 42 can include a base portion 90, a rotatable portion 92, and an actuator 94. Rotation of the rotatable portion 92 can be controlled via operation of the actuator 94 that includes a motor and transmission portion 94 that is actuatable to rotate the rotatable portion 92 and the first vertically-oriented portion 22 supported by the rotatable portion 92 about a vertically-oriented axis. As such, the first platform portion 12 can be rotated relative to the platform portion 78, the first end portion 26, and the support portion 16 via actuation of the actuator 94 of the rotator portion 42. Furthermore, the operation of the rotator portion 42 and the actuator 94 thereof can be controlled by the controllers of the surgical table 10.

Figure 4:
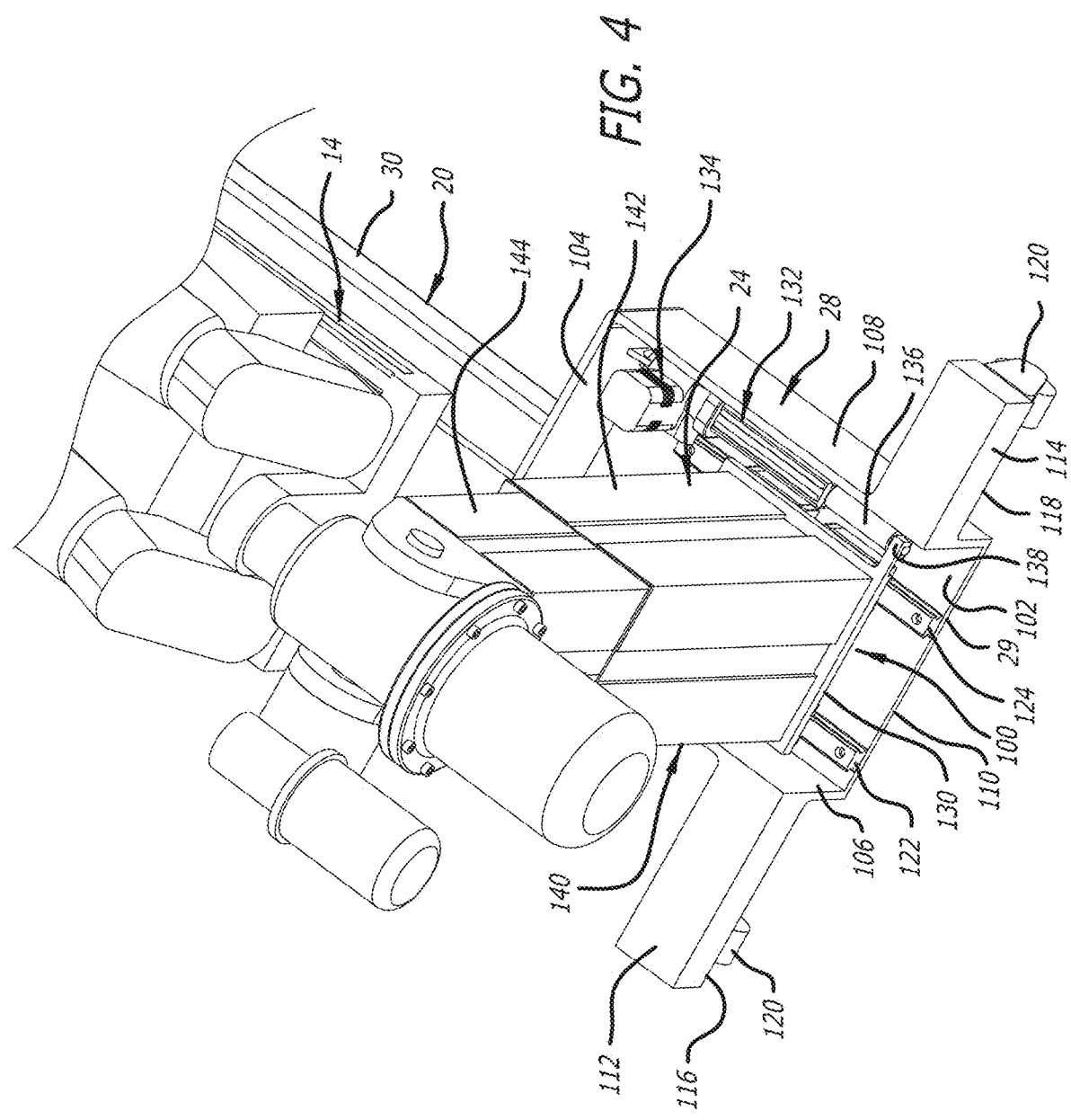
FIG. 4 is a top, perspective view that illustrates a slider portion of a second end portion supporting a second vertically-oriented portion of the surgical table of FIG. 1A.
Figure 5:
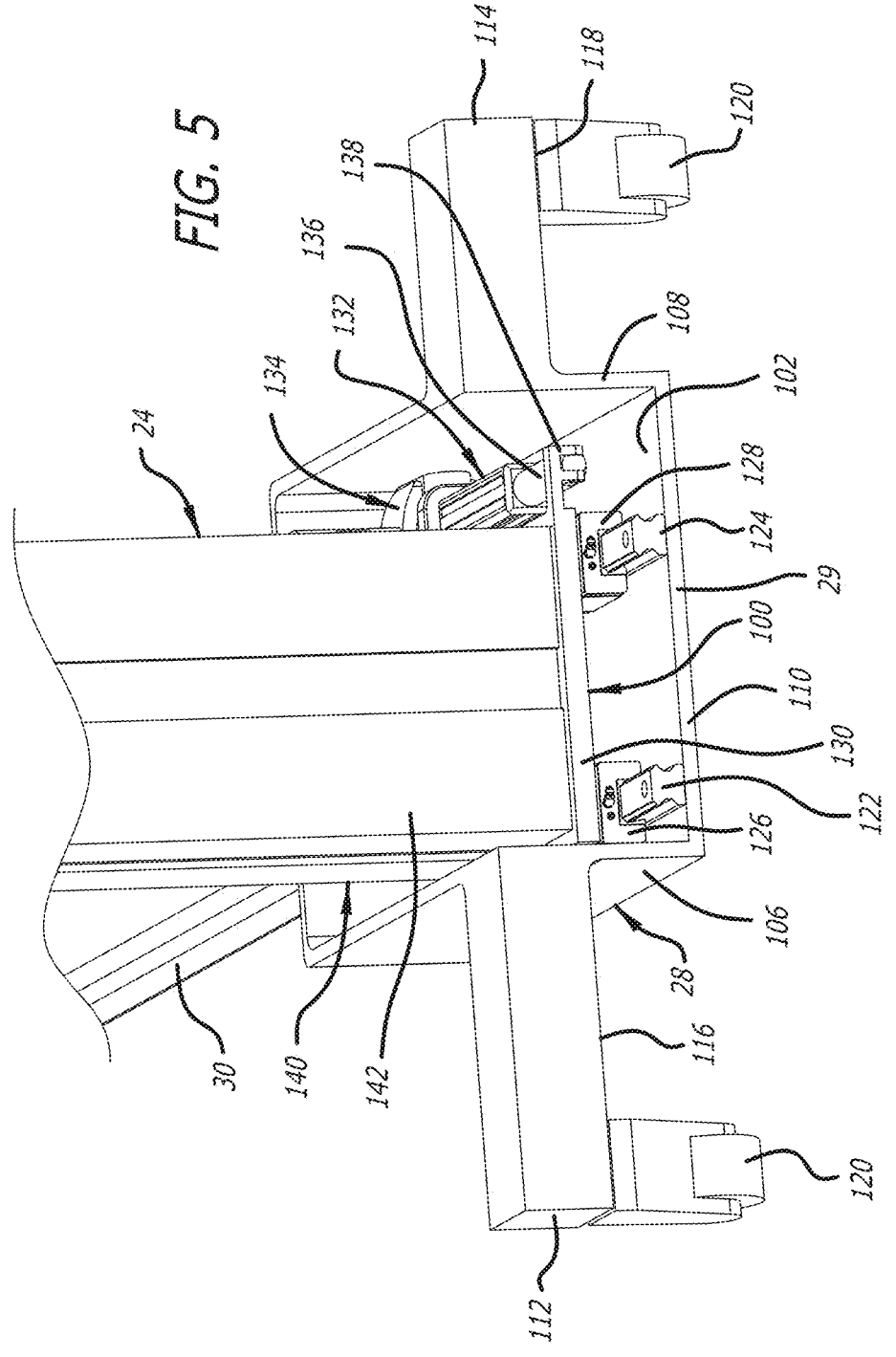
FIG. 5 is an end, perspective view that illustrates the slider portion of the second end portion supporting the second vertically-oriented portion of the surgical table of FIG. 1A.

The second end portion 28, as depicted in FIGS. 4 and 5, supports the second vertically-oriented portion 24, and includes a slider portion 100. As discussed below, the slider portion 100 is configured to move the second vertically-oriented portion 24 toward and away from the first vertically-oriented portion 22 in directions aligned with the longitudinal axes L1 and L2. As depicted in FIGS. 4 and 5, the second end portion 28 includes a bottom portion 102, an endwall portion 104, a first sidewall portion 106, and a second sidewall portion 108.

The second end portion 28 includes an open end 110 adjacent the second end 29, and together, the bottom portion 102, the endwall 104, the first sidewall portion 106, and the second sidewall portion 108 define an area in which the slider portion 100 are provided. An arm portion 112 extends outwardly from the first sidewall portion 106 and an arm portion 114 extends outwardly from the second sidewall portion 108, and the arm portions 112 and 114 include undersurfaces 116 and 118, respectively. Casters 120 can be attached to each of the undersurfaces 116 and 118, and together with the casters 68, the casters 120 can be used to space the support portion 16 from the ground and to facilitate movement of the support portion 16.

The slider portion 100, as depicted in FIGS. 4 and 5, includes a first track portion 122, a second track portion 124, first trucks 126 moveable along the first track portion 122, second trucks 128 moveable along the second track portion 124, and a platform portion 130 supported by the first trucks 126 and the second trucks 128. Using movement of the first trucks 126 and the second trucks 128 on the first track portion 122 and the second track portion 124, respectively, the platform portion 130 is moveable relative to the bottom portion 102 in directions aligned with the longitudinal axes L1 and L2 between a first position and a second position. In the first position, the platform portion 130 is located adjacent the second end 29, and, in the second position, the platform portion 130 is located adjacent the endwall portion 104.

Linear movement of the platform portion 130 can be controlled via operation of an actuator 132 that includes a motor and transmission portion 134 that is actuatable to move a telescoping arm portion 136 inwardly and outwardly. The telescoping arm portion 136 is attached to an extension portion 138 that extends outwardly from the platform portion 130. As such, the inward movement and the outward movement of the telescoping arm portion 138 serves to move the platform portion 130 (and the second vertically-oriented portion 24 supported thereby) between the first position and the second position thereof. As such, the second platform portion 14 supported by the second vertically-oriented portion 24 can be moved toward and away from the first platform portion 12 in directions aligned with the mid-longitudinal axes L1 and L2 via actuation of the actuator 132 of the slider portion 100. Furthermore, the operation of the slider portion 100 and the actuator 132 thereof can be controlled by the controllers of the surgical table 10.

As discussed below, the use of the slider portion 40 and the rotator portion 42 of the first end portion 26, and the use of the slider portion 100 of the second end portion 28 can afford independent movement and adjustment of the first platform portion 12 and the second platform portion 14 relative to one another. Furthermore, rather than employing the slider portion 40 and the rotator portion 42, the first vertically-oriented portion 22 can be supported directly by the first end portion 26 and be fixed in position relative thereto, and rather than employing the slider portion 100, the second vertically-oriented portion 24 can be supported directly by the second end portion 28. As such, if the slider portion 40, the rotatable portion 42, and the slider portion 100 are not provided, portions of the first vertically-oriented portion 22 and the second vertically-oriented portion 24 can be used to facilitate independent movement and adjustment of the first platform portion 12 and the second platform portion 14 relative to one another.

As depicted in FIGS. 1A, 1B, and 6-12, each of the first vertically-oriented portion 22 and the second vertically oriented 24 can include a telescoping column 140 for positioning/orienting and repositioning/reorienting the first platform portion 12 and the second platform portion 14 relative to the horizontally-oriented portion 20. Each of the telescoping columns 140 can include a lower portion 142 and an upper portion 144. The upper portions 144 can be telescopically moved upwardly and downwardly relative to the lower portions 142 between a lower position and an upper position. The lower portions 142 of the telescoping columns 140 are supported by the first end portion 26 and the second end portion 28. As such, the telescopic expansion and contraction of the telescoping columns 140 can be used to correspondingly raise and lower the first platform portion 12 and the second platform portion 14 relative to the horizontally-oriented portion 20.

Figure 1B:
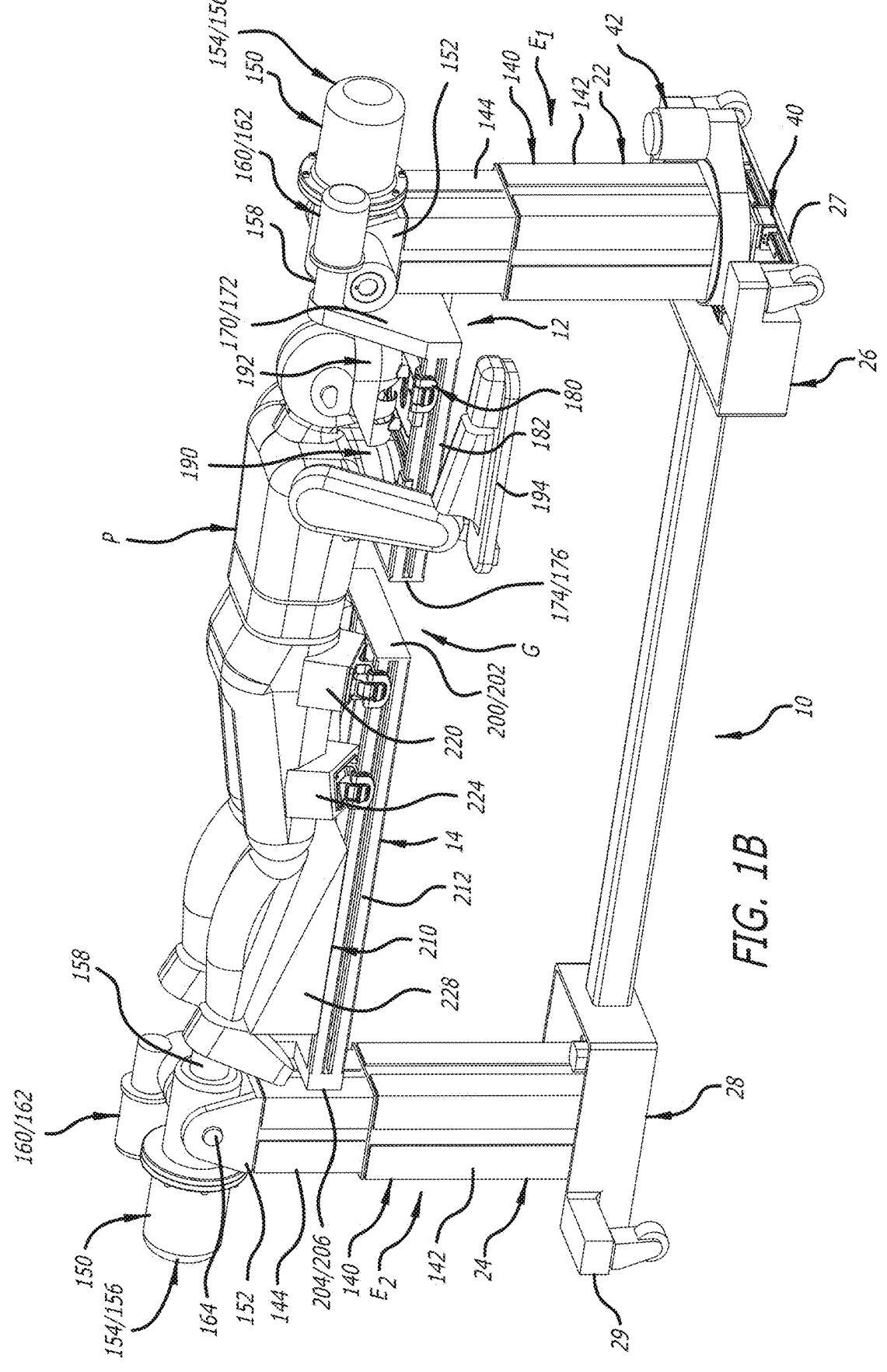
FIG. 1B is a side, perspective view similar to FIG. 1A that illustrates the surgical table of FIG. 1A with a patient positioned thereon in a prone position.
Figure 1C:
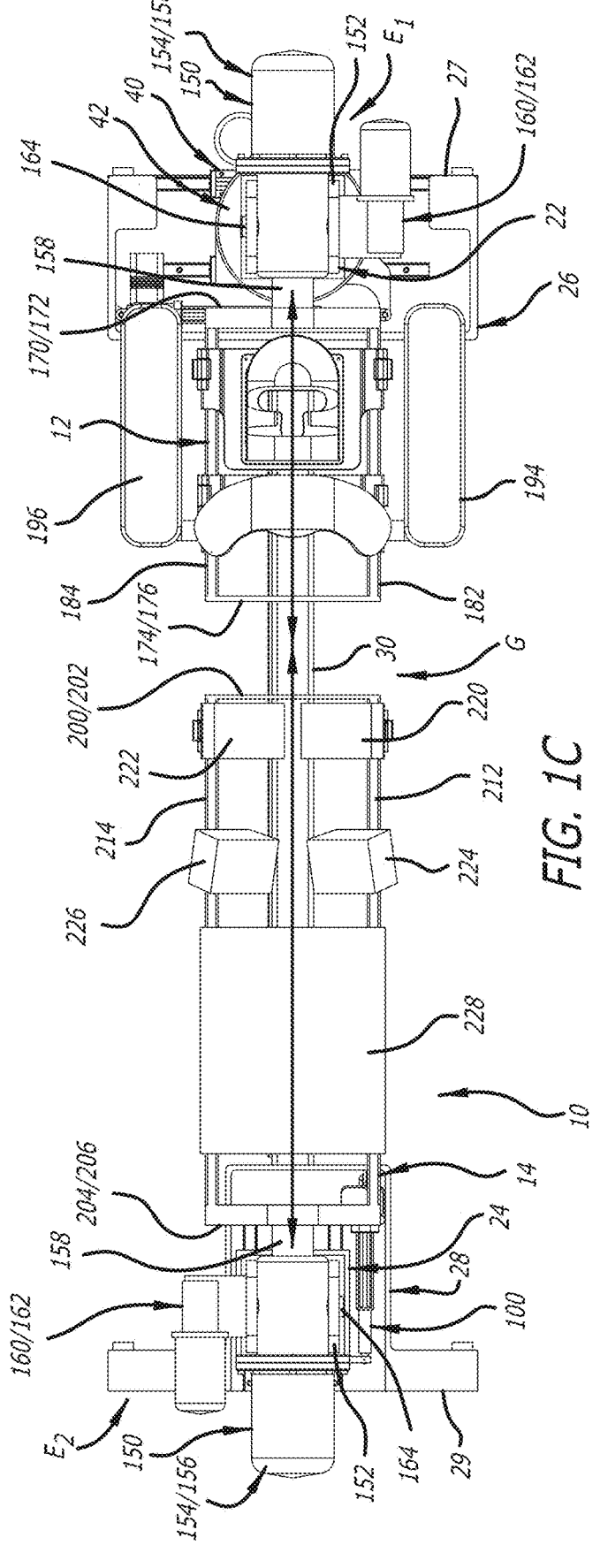
FIG. 1C is a top, plan view that illustrates the surgical table of FIG. 1A with the patient positioned thereon.

As depicted in FIGS. 1A, 1B, and 6-12, each of the first vertically-oriented portion 22 and the second vertically-oriented portion 24 also include a rotational/tilt positioner 150. Each of the rotational/tilt positioners 150 can be supported relative to the telescoping column 140 by a clevis 152 attached to the upper portion 144. The rotational/tilt positioners 150 each include a rotational portion 154 including a motor and transmission 156 and an axle 158, and a tilt portion 160 including a motor and transmission 162 and an axle 164. As depicted in FIGS. 1A-1C, portions of the motors and transmissions 156 of the rotational portions 154 can be positioned between portions of the clevis 152, and the axles 158 can extend outwardly from the motors and transmissions 156 and be attached to the first platform portion 12 and the second platform portion 14. Furthermore, the motors and transmissions 162 of the tilt portions 160 can be positioned on one side of portions of the clevises 152, and the axles 164 can be received through the clevises 152 and be attached to portions of the rotational portions 154. Operation of the motors and transmissions 156 serve in rotating the axle 158 to rotate the first platform portion 12 and the second platform portion 14 attached thereto, and operation of the motors and transmissions 162 serves in rotating the axles 164 to tilt the rotational portions 154 and the first platform portion 12 and the second platform portion 14 attached thereto.

Accordingly, to further position/orient and reposition/reorient the first platform portion 12 and the second platform portion 14, the platform portion 12 and the second platform portion 14 each can be raised and lowered via expansion and contraction of the telescoping columns 140, the first platform portion 12 and the second platform portion 14 each can be rotated side to side by rotation of the axles 158 using the motors and transmissions 156, and the first platform portion 12 and the second platform portion 14 can be tilted upwardly or downwardly by rotation of the axles 164 using the motors and transmissions 162. The rotation of the axles 158 can rotate the first platform portion 12 and the second platform portion 14 side to side in a vertical plane perpendicular to the mid-longitudinal axes L1 and L2, and the rotation of the axles 164 can tilt the first platform portion 12 and the second platform portion 14 upwardly and downwardly in a vertical plane aligned with the mid-longitudinal axes L1 and L2 As discussed below, the operation of the telescoping columns 140, the motors and transmissions 156, and the motors and transmissions 162 can be controlled by the controllers of the surgical table 10.

As depicted in FIGS. 1A-1C, the first platform portion 12 includes a first end portion 170 at and adjacent a first end 172 thereof, a second end portion 174 at and adjacent a second end 176 thereof, and various rails positioned therebetween that connect the first end portion 170 and the second end portion 174 to one another. A portion of first end portion 170 has a height sufficient enough to afford attachment relative to the axle 158 of the rotational/tilt positioner 150 of the first vertically-oriented portion 22, and such attachment affords movement thereof via operation of the rotational/tilt positioner 150.

The first platform portion 12 includes a first patient support portion 180, and the various rails, as depicted in FIGS. 1A and 1C, can include a first outer rail 182 and a second outer rail 184 that extend between the first end portion 170 and the second end portion 174. First end portions of the first outer rail 182 and the second outer rail 184 can be attached to the first end portion 170, opposite second end portions of the first outer rail 182 and the second outer rail 184 can be attached to the second end portion 174, and/or the first and second end portions can be attached to intermediate portions (not shown) positioned between the various rails and the first end portion 170 and/or the second end portion 174. Furthermore, the first outer rail 182 and the second outer rail 184 can be aligned with a mid-longitudinal axis L3 of the first platform portion 12, with the first outer rail 182 being positioned on one side of the mid-longitudinal axis L3, and the second outer rail 184 being positioned on the other side of the mid-longitudinal axis L3.

In addition to providing structural rigidity to the first platform portion 12, the first outer rail 182 and the second outer rail 184 can also be used to support the first patient support portion 180 of the first platform portion 12. The patient support portion 180 can include a chest support portion 190 and a head support portion 192 that are integrated with or separate from one another. As depicted in FIG. 1C, the chest support portion 190 and the head support portion 192 are separate from one another. Furthermore, the chest support portion 190 and/or the head support portion 192 can be moveably adjusted or fixed in position along portions of the first outer rail 182 and the second outer rail 184 to accommodate differently-sized patients. As such, the first outer rail 182 and the second outer rail 184 serves as tracks affording movement of the chest support portion 190 and the head support portion 192. As depicted in FIGS. 1B and 6-12, the patient P is supported in a prone position by the first patient support portion 180, with the upper torso of the patient being supported by the chest support portion 190, and the head of the patient being supported by the head support portion 192. The chest support portion 190 and the head support portion 192 can be configured and operate in similar fashion to those disclosed in U.S. Ser. Nos. 17/740,559 and 17/740,588, both filed May 10, 2022, which are hereby incorporated by reference herein.

In addition to the chest support portion 190 and the head support portion 192, first and second arm supports 194 and 196 can be provided as part of the first platform portion 12 to support arms of the patient relative to the remaining portions thereof. As depicted in FIG. 1C, the first arm support 194 is attached relative to the first outer rail portion 182, and the second arm support 196 is attached relative to the second outer rail portion 184. As such, when the patient P is in the prone position with the upper torso of the patient supported by the chest support portion 190 and the head of the patient supported by the head support portion 192, the right arm and the left arm of the patient can be supported relative to the remainder of the first platform portion 12 by the first arm support 194 and the second arm support 196, respectively.

As depicted in FIGS. 1A-1C, the second platform portion 14 includes a first end portion 200 at and adjacent a first end 202 thereof, a second end portion 204 at and adjacent a second end 206 thereof, and various rails positioned therebetween that connect the first end portion 200 and the second end portion 204 to one another. A portion of second end portion 204 has a height sufficient enough to afford attachment relative to the axle 158 of the rotational/tilt positioner 150 of the second vertically-oriented portion 24, and such attachment affords movement thereof via operation of the rotational/tilt positioner 150.

The second platform portion 14 includes a second patient support portion 210, and the various rails, as depicted in FIGS. 1A and 1C, can include a first outer rail 212 and a second outer rail 214 that extend between the first end portion 200 and the second end portion 204. First end portions of the first outer rail 212 and the second outer rail 214 can be attached to the first end portion 200, opposite second end portions of the first outer rail 212 and the second outer rail 214 can be attached to the second end portion 204, and/or the first and second end portions can be attached to intermediate portions (not shown) positioned between the various rails and the first end portion 200 and/or the second end portion 204. Furthermore, the first outer rail 212 and the second outer rail 214 can be aligned with a mid-longitudinal axis L4 of the second platform portion 14, with the first outer rail 212 being positioned on one side of the mid-longitudinal axis L4, and the second outer rail 214 being positioned on the other side of the mid-longitudinal axis L4.

In addition to providing structural rigidity to the second platform portion 14, the first outer rail 212 and the second outer rail 214 can also be used to support the second patient support portion 210 that can include a first upper thigh support 220, a second upper thigh support 222, a first lower thigh support 224, and a second lower thigh support 226. The first upper thigh support 220, the second upper thigh support 222, the first lower thigh support 224, and the second lower thigh support 226 can be moveably adjusted or fixed in position along portions of the first outer rail 212 and the second outer rail 214 to accommodate differently-sized patients. As depicted in FIGS. 1A and 1C, the first upper thigh support 220 and the first lower thigh support 224 are supported by the first outer rail 212, and the second upper thigh support 222 and the second lower thigh support 226 are supported by the second outer rail 214. As such, the first outer rail 212 and the second outer rail 214 serve as tracks affording movement of the first upper thigh support 220, the second upper thigh support 222, the first lower thigh support 224, and the second upper lower support 226. In addition to the first upper thigh support 220, the second upper thigh support 222, the first lower thigh support 224, and/or the second lower thigh support 226, a lower leg support 228 of the second patient support portion 210 can be provided. As depicted in FIGS. 1B and 6-12, the patient P is supported in a prone position by the first upper thigh support 220, the second upper thigh support 222, the first lower thigh support 224, the second lower thigh support 226, and the lower leg support 228. The first upper thigh support 220, the second upper thigh support 222, the first lower thigh support 224, the second upper thigh support 226, and the lower leg support 228 can be configured and operate similar fashion to those disclosed in U.S. Ser. Nos. 17/740,559 and 17/740,588, both filed May 10, 2022, which are incorporated by reference herein.

As depicted in FIGS. 1B and 6-12, adjustment of the relative positions of the first platform portion 12 and the second platform portion 14 affords positioning/orienting and repositioning/reorienting of the patient P supported thereby before, during, and after surgery. To illustrate, the first platform portion 12 and the second platform portion 14 can be independently adjusted relative to another to position/orient and reposition/reorient portions of the patient supported thereby. The independent adjustment of the relative positions of the first platform portion 12 and the second platform portion 14 is afforded by the separation therebetween defined by the gap G, and such adjustment can correspondingly be used to change the position/orientation of a first portion of the patient P supported by the first platform portion 12 and a second portion of the patient P supported by the second platform portion 14 relative to one another.

As depicted in FIGS. 1B and 6-12, for example, the head and upper torso of the patient P are supported by the first platform portion 12 and the upper and lower legs of the patient P are supported by the second platform portion 14. And, while the head and upper torso of the patient P are supported by the first patient support portion 180 on the first platform portion 12, and the upper and lower legs of the patient P are supported by the second patient support portion 210 on the second platform portion 14, the position of the patient P could be reversed with the first patient support portion 180 supporting the head and upper torso of the patient P on the second platform portion 14, and the second patient support portion 210 supporting the upper and lower legs of the patient P on the first platform portion 12. Furthermore, while the patient is supported in the prone position in FIGS. 1B and 6-12 the patient P could be supported in the supine position on the first platform portion 12 and the second platform portion 12.

The first platform portion 12 can be raised and lowered via operation of the corresponding telescoping column 140, can be rotated with rotation of the corresponding axle 158 via actuation of the corresponding motor and transmission 156 of the corresponding rotational portion 154, can be titled with rotation of the corresponding axle 164 via actuation of the corresponding motor and transmission 162 of the corresponding tilt portion 160, can be moved in side-to-side directions relative to the mid-longitudinal axes L1 and L2 via actuation of the actuator 80 of the slider portion 40, and can be rotated about a vertically-oriented axis relative to the support portion 16 via actuation of the actuator 94 of the rotator portion 42. Furthermore, the second platform portion 14 can be raised and lowered via operation of the corresponding telescoping column 140, can be rotated with rotation of the corresponding axle 158 via actuation of the corresponding motor and transmission 156 of the corresponding rotational portion 154, can be titled with rotation of the corresponding axle 164 via actuation of the corresponding motor and transmission 162 of the corresponding tilt portion 160, and can be moved toward and away from the first platform portion 12 in directions aligned with the mid-longitudinal axes L1 and L2 via actuation of the actuator 132 of the slider portion 100. In addition to such movement, the chest support portion 130, the head support portion 132, the first the first upper thigh support 220, the second upper thigh support 222, the first lower thigh support 224, the second lower thigh support 226, and the lower leg support 228 can be adjusted to accommodate differently-sized patients.

In manipulating the patient P, the telescoping column 140 of the first vertically-oriented portion 22 could be actuated to raise the position of the first platform portion 12 and the tilt portion 160 of the first vertically-oriented portion 22 could be actuated to tilt the position/orientation of the first platform portion 12, and in doing so, bend the patient's body from a neutral position/orientation (FIG. 6) to tilt the head and upper torso upwardly. Similarly, the telescoping platform 140 of the second vertically-oriented portion 22 could be actuated to raise the position of the second platform portion 14 and the tilt portion 160 of the second vertically-oriented portion could be actuated to tilt the position/orientation of the second platform portion 14, and in doing so, bend the patient's body to tilt the legs upwardly. Furthermore, as depicted in FIG. 7, the first support platform 12 and the second support platform 14 could be positioned/oriented to both tilt the head and upper torso of the patient P upwardly and tilt the legs of the patient P upwardly. Accordingly, the positions/orientations of the first support platform 12 and the second support platform 14 via actuation of the telescoping columns 140 and the tilt portions 160 of the first vertically-oriented portion 22 and the second vertically-oriented portion 24 can be adjusted from a neutral position/orientation as depicted in FIG. 6, to bend the patient's body to move the head and upper torso upwardly and/or move the legs upwardly to introduce degrees of extension to the patient's spine.

Figure 6:
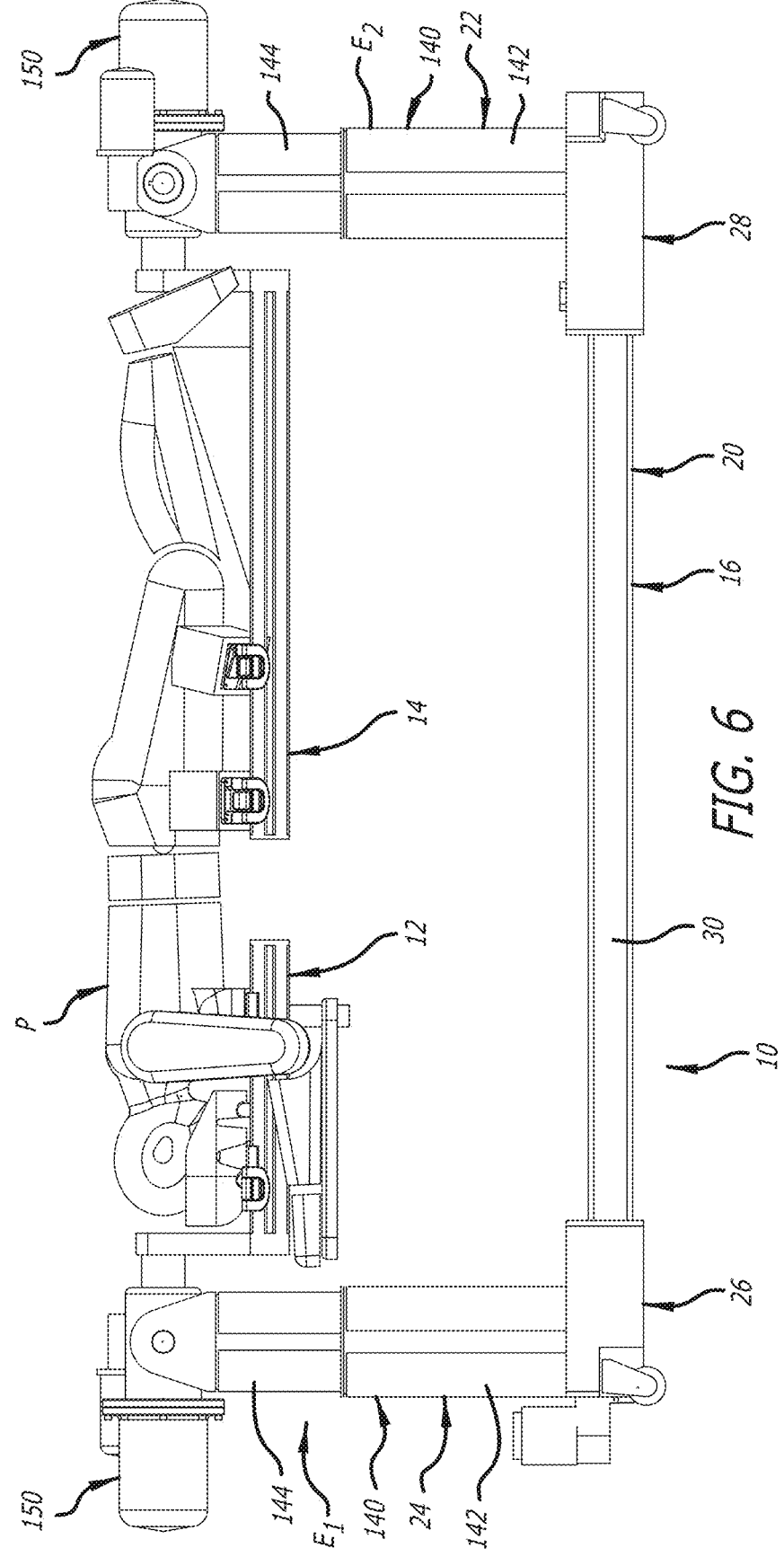
FIG. 6 is a side, elevational view that illustrates the patient positioned on the surgical table of FIG. 1A in the prone position with a first portion of the patient supported by a first platform portion and a second portion of the patient supported by a second platform portion in a neutral position.
Figure 7:
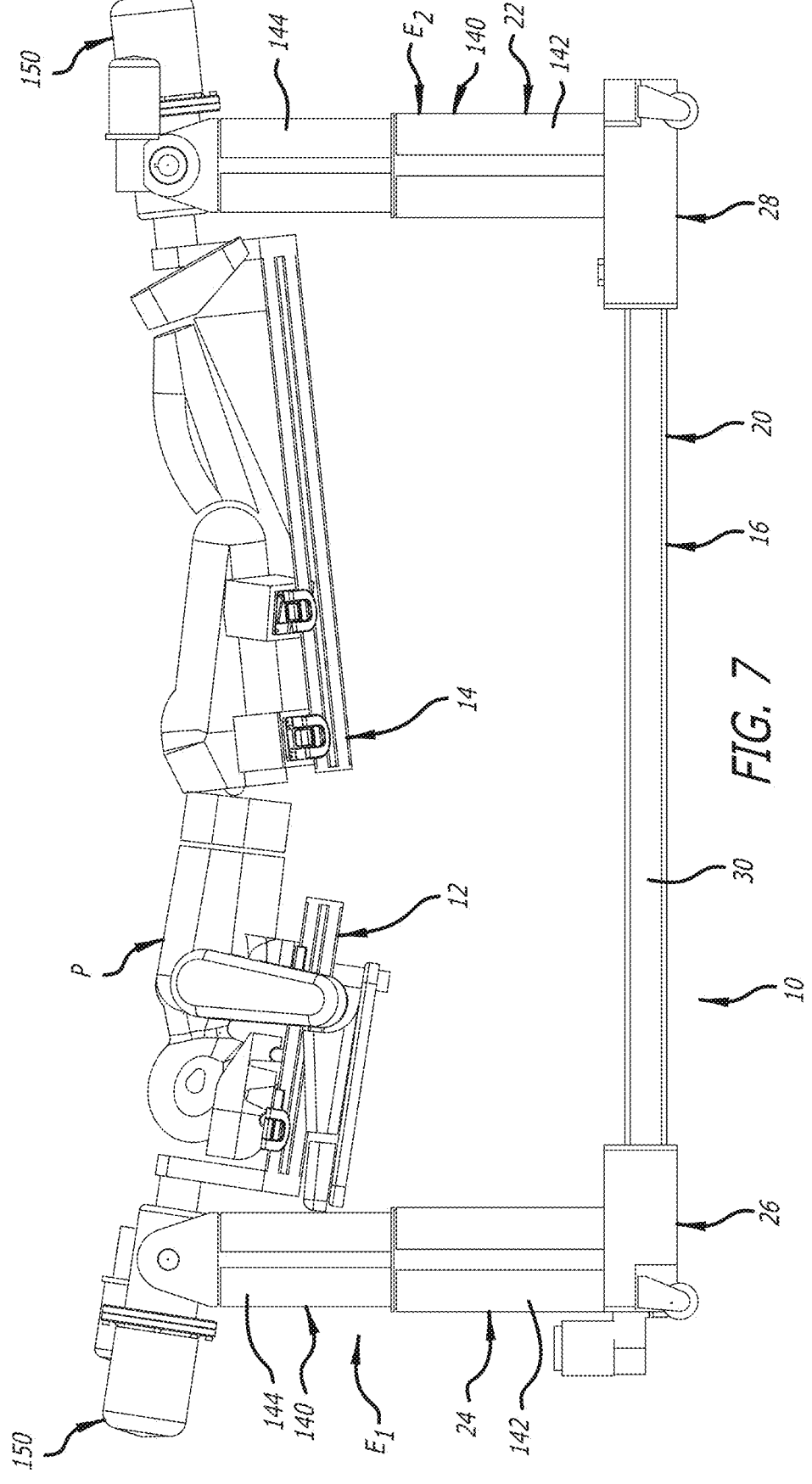
FIG. 7 is a side, elevational view that illustrates the first and second portions of the surgical table of FIG. 1A and the corresponding first and second portions of the patient supported thereon raised and tilted downwardly relative to another.
Figure 8:
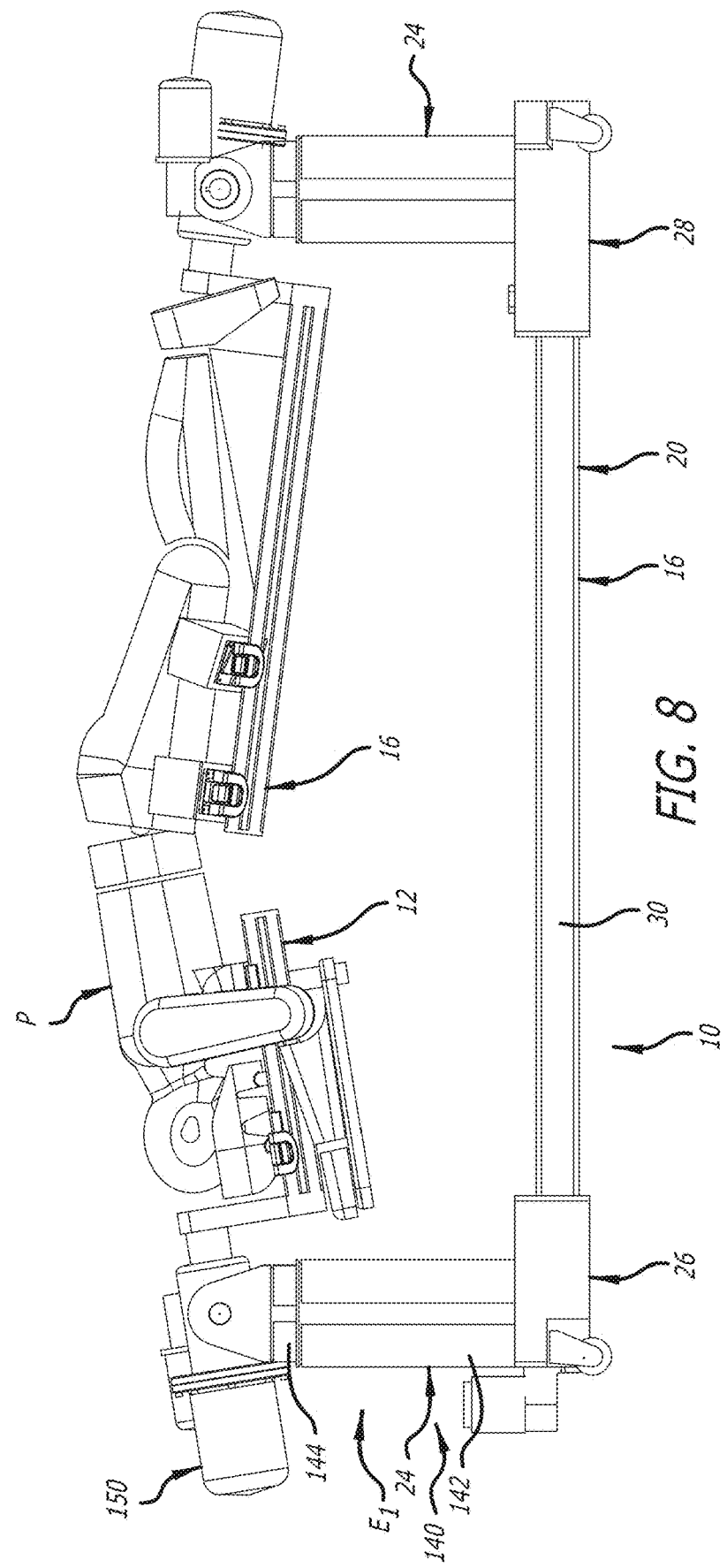
FIG. 8 is a side, elevational view that illustrates the first and second portions of the surgical table of FIG. 1A and the corresponding first and second portions of the patient supported thereon lowered and tilted upwardly relative to another.

Furthermore, the positions/orientations of the first support platform 12 and the second support platform 12, via actuation of the telescoping column 140 and the tilt portions 160 of the first vertically-oriented portion 22 and the second vertically-oriented portion 24, can be adjusted to bend the patient's body from the neutral position/orientation as depicted in FIG. 6, to move the head and upper torso downwardly and/or move the legs downwardly to introduce degrees of flexion to the patient's spine as depicted in FIG. 8.

In addition to the extension and the flexion of the patient's spine discussed above, the first portion of the patient's body supported by the first platform portion 12 and the second portion of the patient's body supported by the second platform portion 16 can be twisted relative to one another to introduce torsion therebetween via actuation of the rotational portions 154 of the first vertically-oriented portion 22 and the second vertically-oriented portion 24. Furthermore, the telescoping columns 140 of the first vertically-oriented portion 22 and the second vertically-oriented portion 24 can also be actuated (without tilting or twisting) to raise the first portion of patient's body supported by the first platform portion 12 relative to the second portion of the patient's body supported by the second platform portion 16, or vice versa. And, the sagittal position of the first portion relative to the second portion of the patient's body can be adjusted by operation of the slider portion 40 and the rotatable portion 42, and the patient's body can be stretched or contracted by operation of the slider portion 100.

Figure 9:
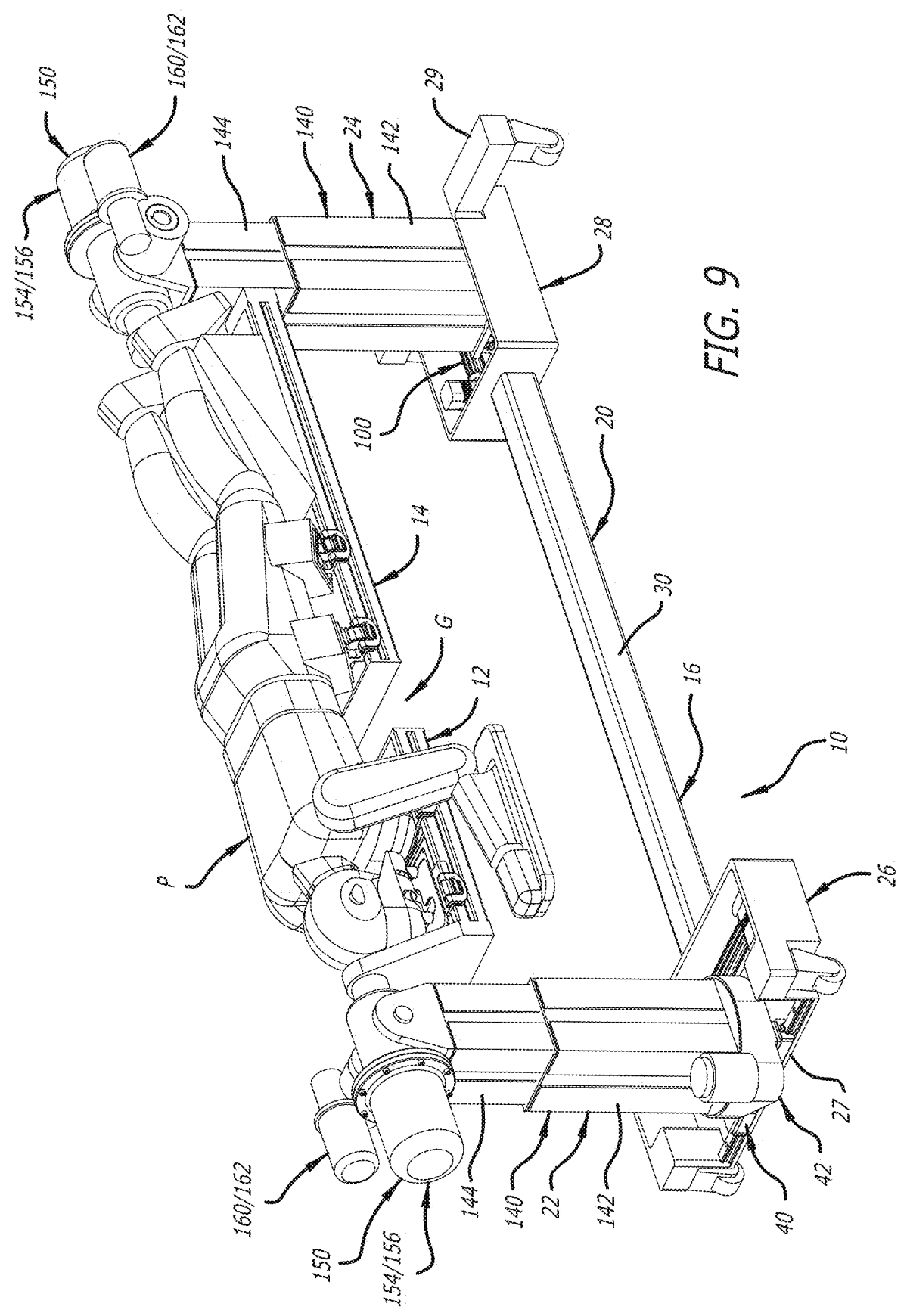
FIG. 9 is a side, perspective view that illustrates the patient positioned on the surgical table of FIG. 1A with the first portion of the patient positioned on the first platform portion and the second portion of the patient positioned on the second platform portion in a neutral position.
Figure 10:
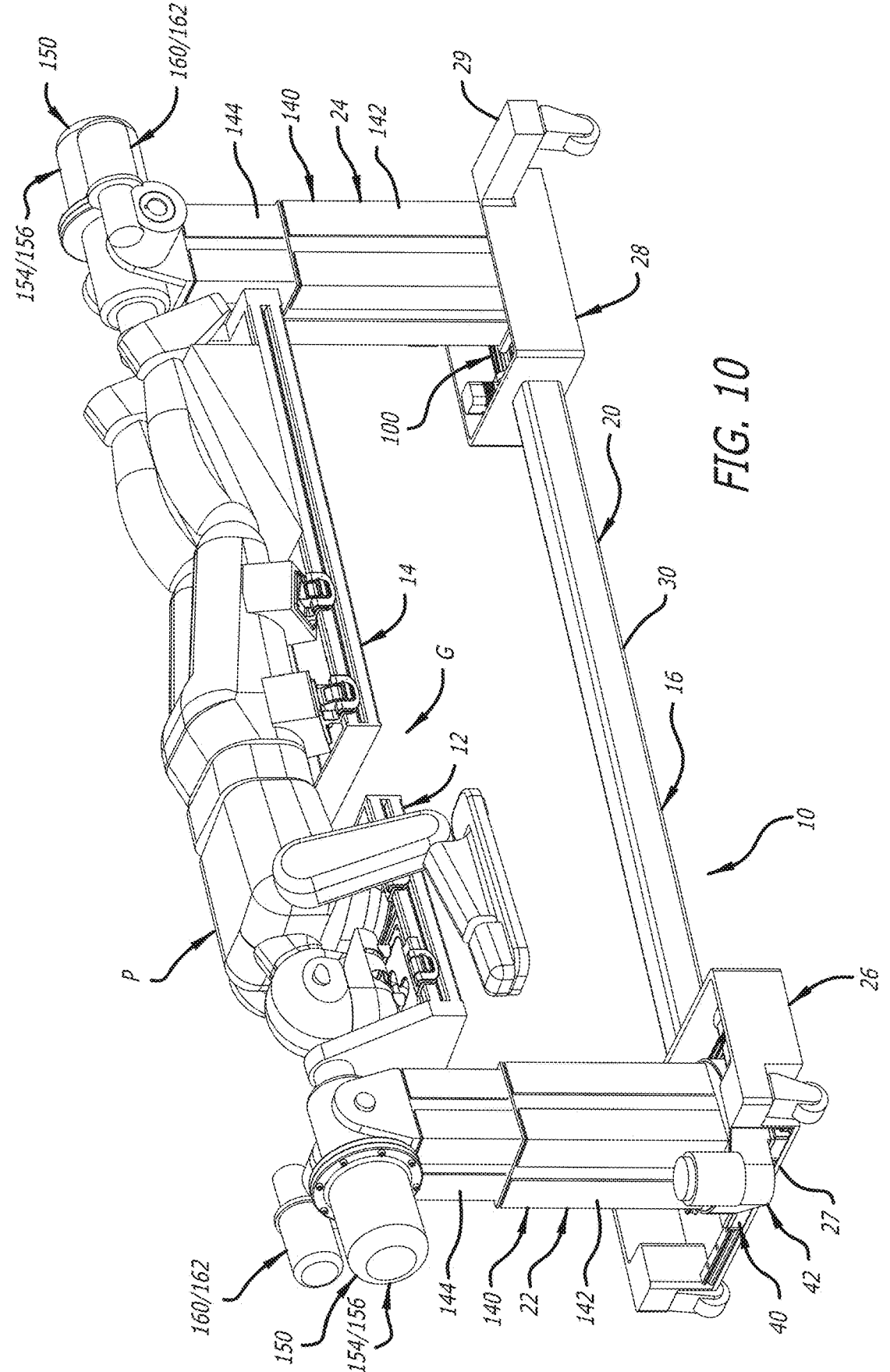
FIG. 10 is a side, perspective view similar to FIG. 9 that illustrates sagittal adjustment of the position/orientation of the patient via movement of the first platform portion relative to the second platform portion.
Figure 11:
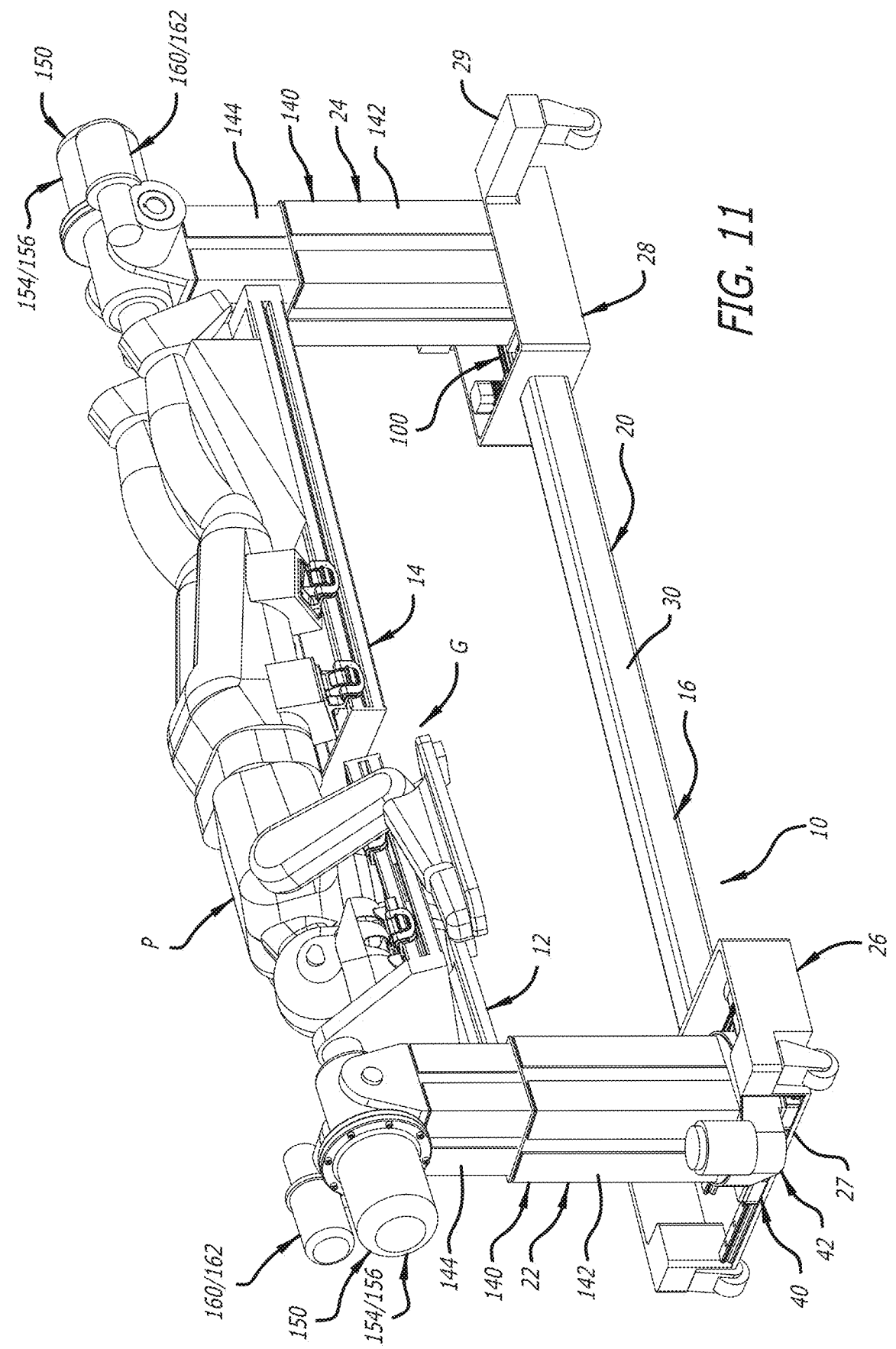
FIG. 11 is a side, perspective view similar to FIGS. 9 and 10 that illustrates torsional adjustment in addition to the sagittal adjustment of the position/orientation of the patient via movement of the first platform portion and the second platform portion relative to one another.
Figure 12:
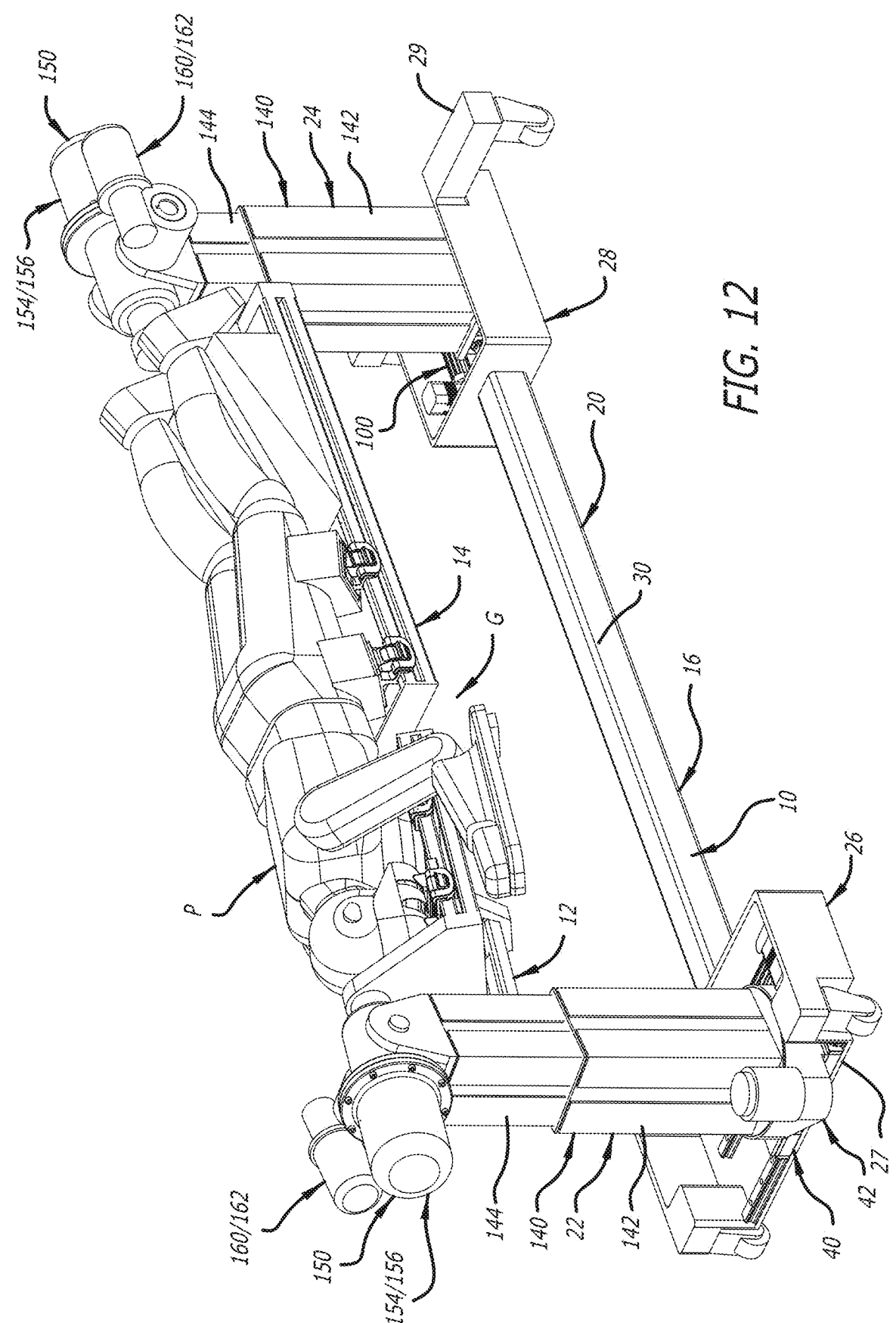
FIG. 12 is a side, perspective view similar to FIGS. 9-11 that illustrates extensional adjustment in addition to the sagittal and torsional adjustment of the position/orientation of the patient via movement of the first platform portion and the second platform portion relative to one another.
Figure 13:
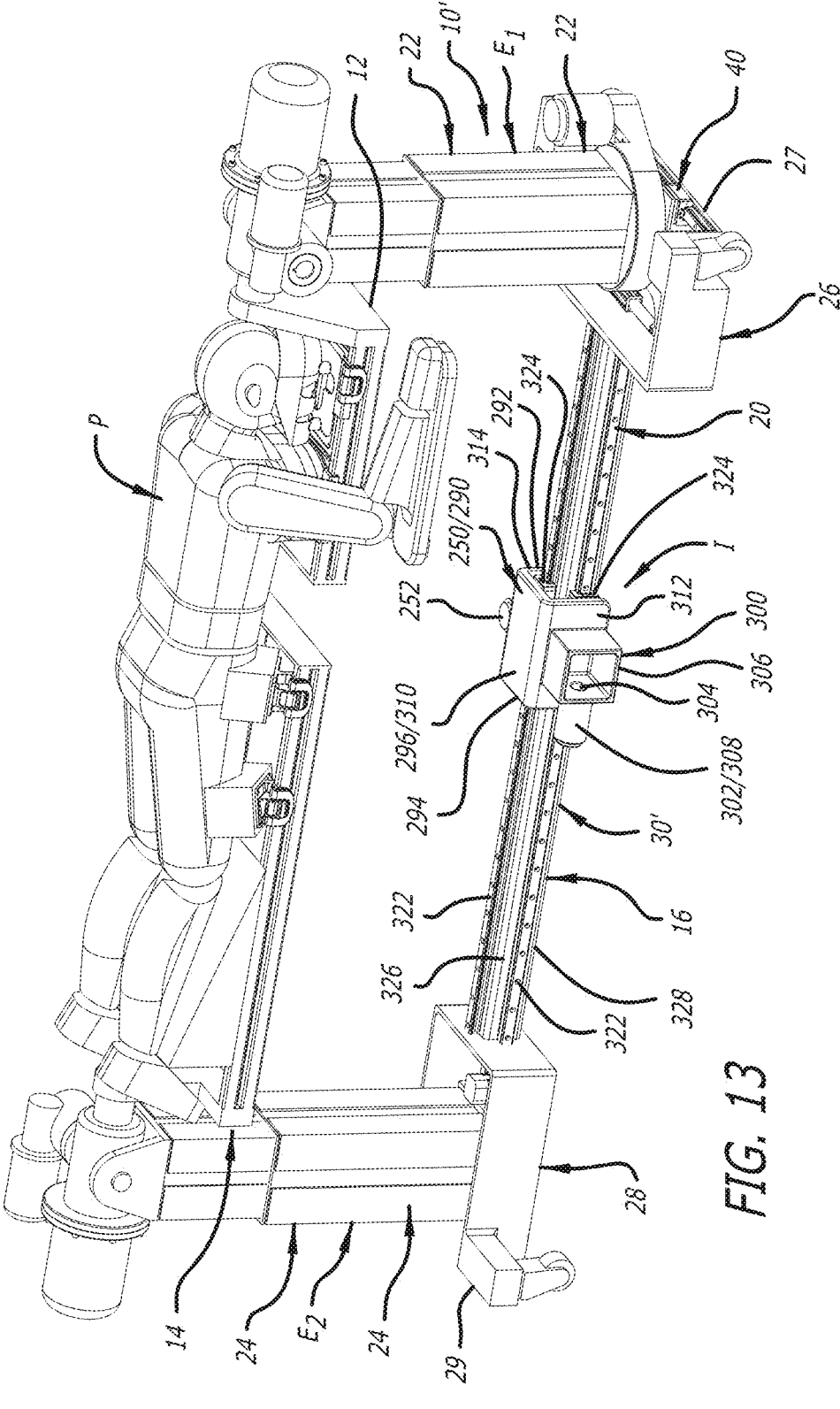
FIG. 13 is a side, perspective view of a surgical table of the present disclosure that illustrates the surgical table supporting a patient thereon and incorporating a collar portion of an interface thereon.
Figure 14:
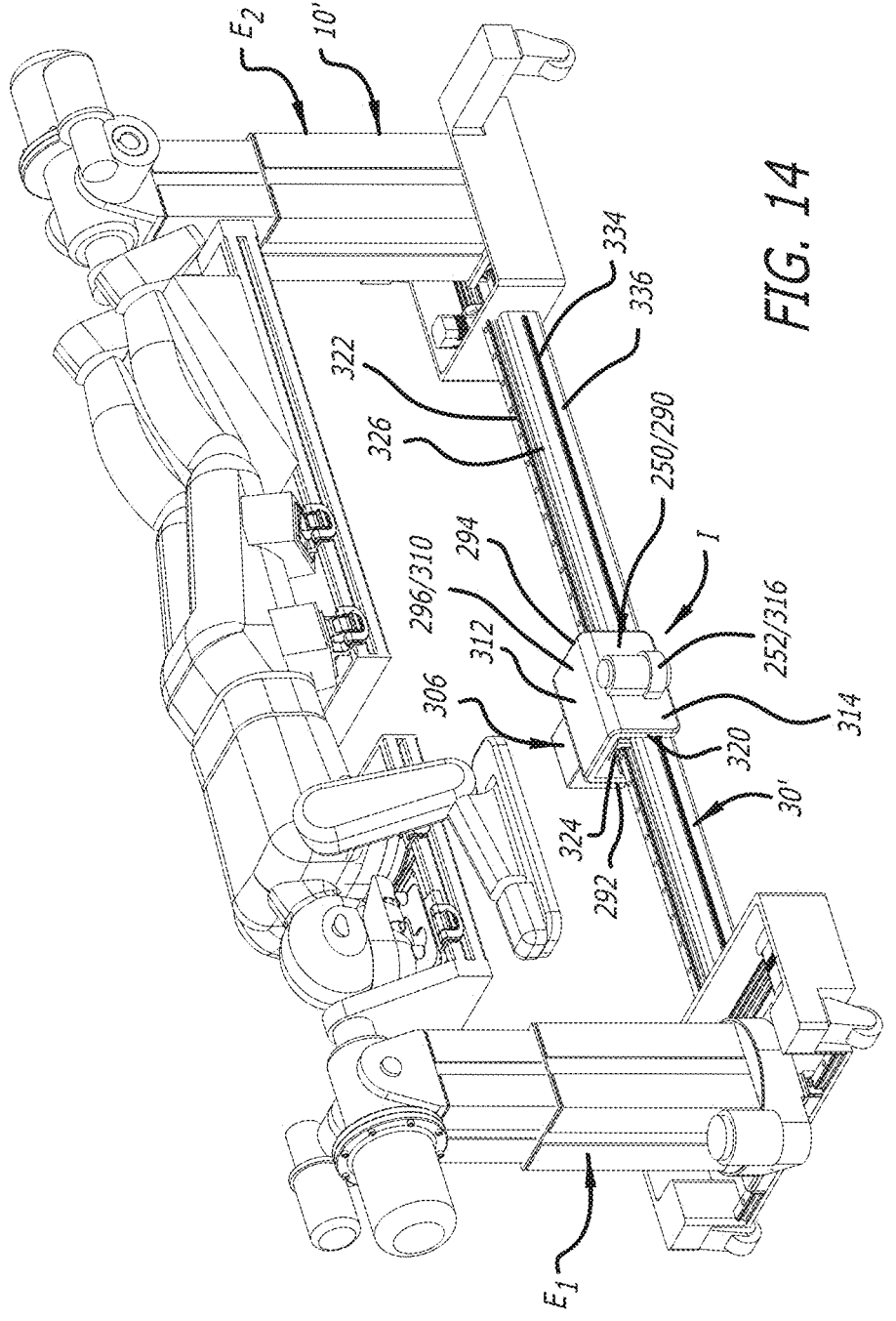
FIG. 14 is a side, perspective view of the surgical table of FIG. 13 supporting the patient thereon that illustrates a first actuator of the interface incorporated on the collar portion for facilitating movement afforded by the interface in a cranial-caudal direction.

As depicted in FIG. 9, the patient P is positioned/oriented in neutral position/orientation, and thereafter in FIGS. 10-12, independent adjustment of the first platform portion 12 and the second platform portion 14 relative to one another is used to adjust the position/orientation of the first portion of the patient's body supported by the first platform portion 12 and the second portion of the patient's body supported by the second platform portion 14 relative to one another. As depicted in FIG. 10, the slider portion 40 can be actuated to move the first platform portion 12 in a direction transverse to the mid-longitudinal axis L2, and the rotator portion 42 can be actuated to rotate the first platform portion 12 about a vertically-oriented axis. In doing so, the sagittal position/ orientation of the patient P can be adjusted, as depicted in FIG. 10, via relative adjustment of the first platform portion 12 with respect to the second platform portion 14 using the slider portion 40 and the rotator portion 42. Then, as depicted in FIG. 11, the first platform portion 12 can be rotated via actuation of the rotational portion 154 and the second platform portion 14 can be moved closer to the first platform portion 12 via actuation of the slider 100 to adjust the torsional position/orientation (in addition to the adjusted sagittal position) of the first portion and the second portion of the patient P relative to one another. And, as depicted in FIG. 12, the first platform portion 12 can be raised and tilted via respective actuation of the telescoping column 140 and the tilt portion 160 of the first vertically-oriented portion 22, and the second platform portion 14 can be lowered via actuation of the telescoping column 140 of the second vertically-oriented portion 24 to adjust the extensional position/orientation (in addition to the adjusted sagittal and torsional position/orientation) of the first portion and the second portion of the patient P relative to one another.

Accordingly, the actuation of the telescoping columns 140, the rotational portions 154, tilt portions 160, the slider portions 40, the rotational portions 42, and/or the slider portion 100 can be used to independently adjust the relative positions and orientations of the first platform portion 12 and the second platform portion 16. And the relative movement of the first platform portion 12 and the second platform portion 16 can be used to adjust the position/orientation of the patient's body P before, during, and after surgery. As discussed above, the surgical table 10 can include a controller or controllers for controlling actuatable portions thereof to facilitate the operation thereof to coordinate movement therebetween. And such coordinated movement via the controller or controllers, for example, can be used to manipulate and prevent over-extension or over-flexion of the spine of the patient before, during, and after surgery. Thereafter, when the surgery is complete, the patient can be removed from the first platform portion 12 and the second platform portion 14.

Figure 22:
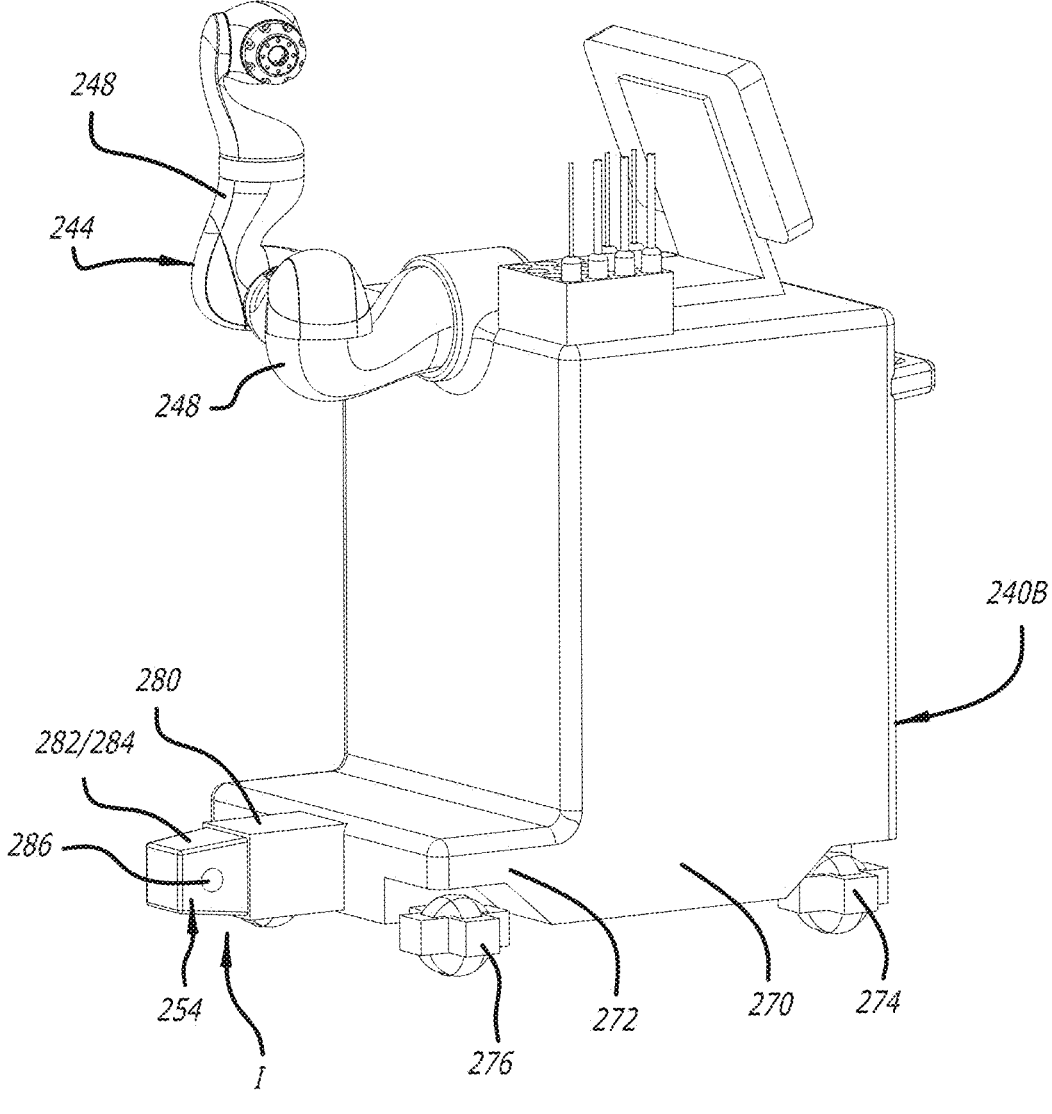
FIG. 22 is a side, perspective view of a second cart portion of the present disclosure that illustrates the cart portion incorporating a surgical robotic system and an extension portion of the interface thereon.
Figure 23:
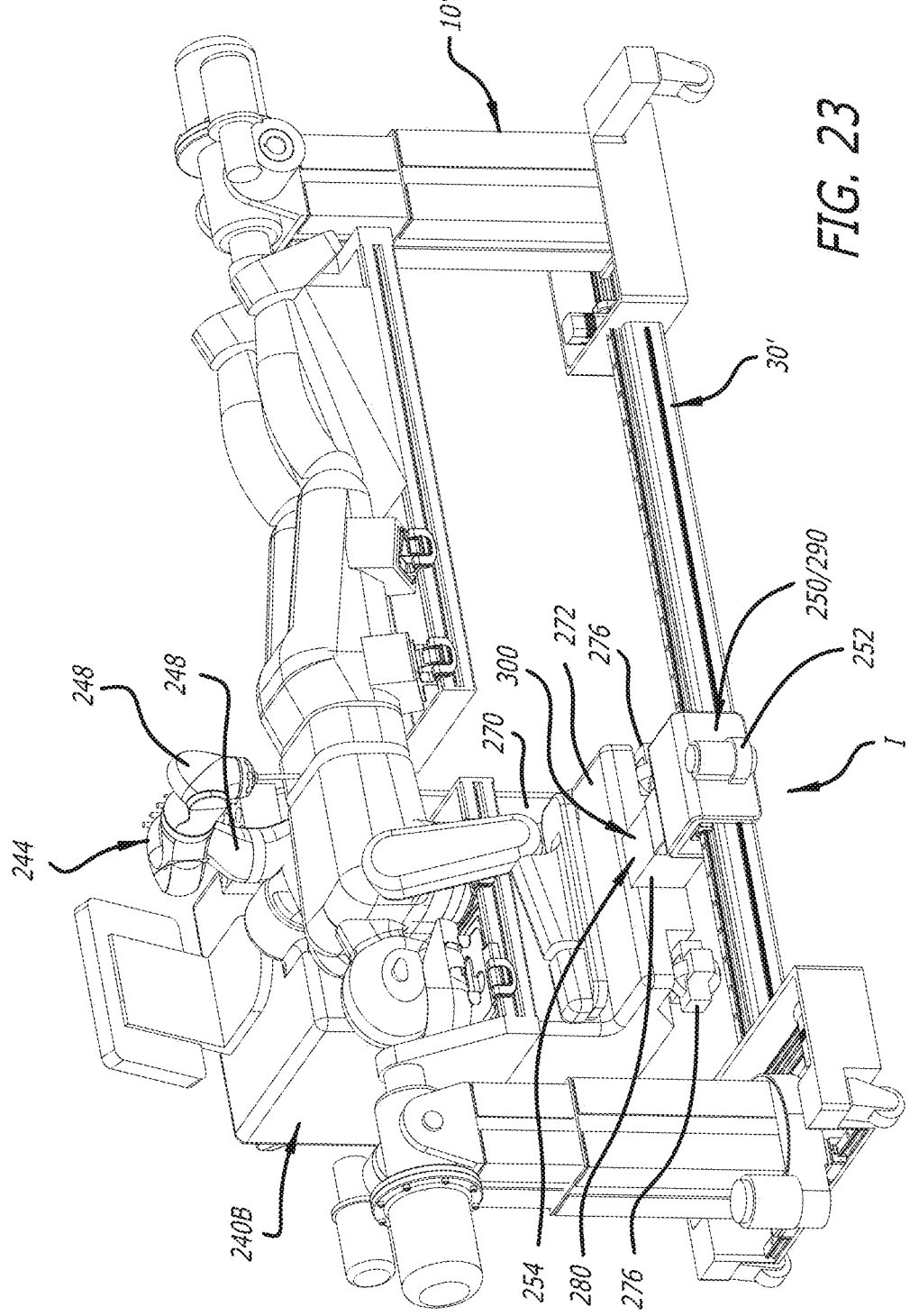
FIG. 23 is a side, perspective view of the second cart portion of FIG. 22 being interconnected with the surgical table of FIG. 13 supporting the patient thereon that illustrates the second cart portion and the surgical robotic system positioned in a first position relative to the surgical table and the patient.
Figure 24:
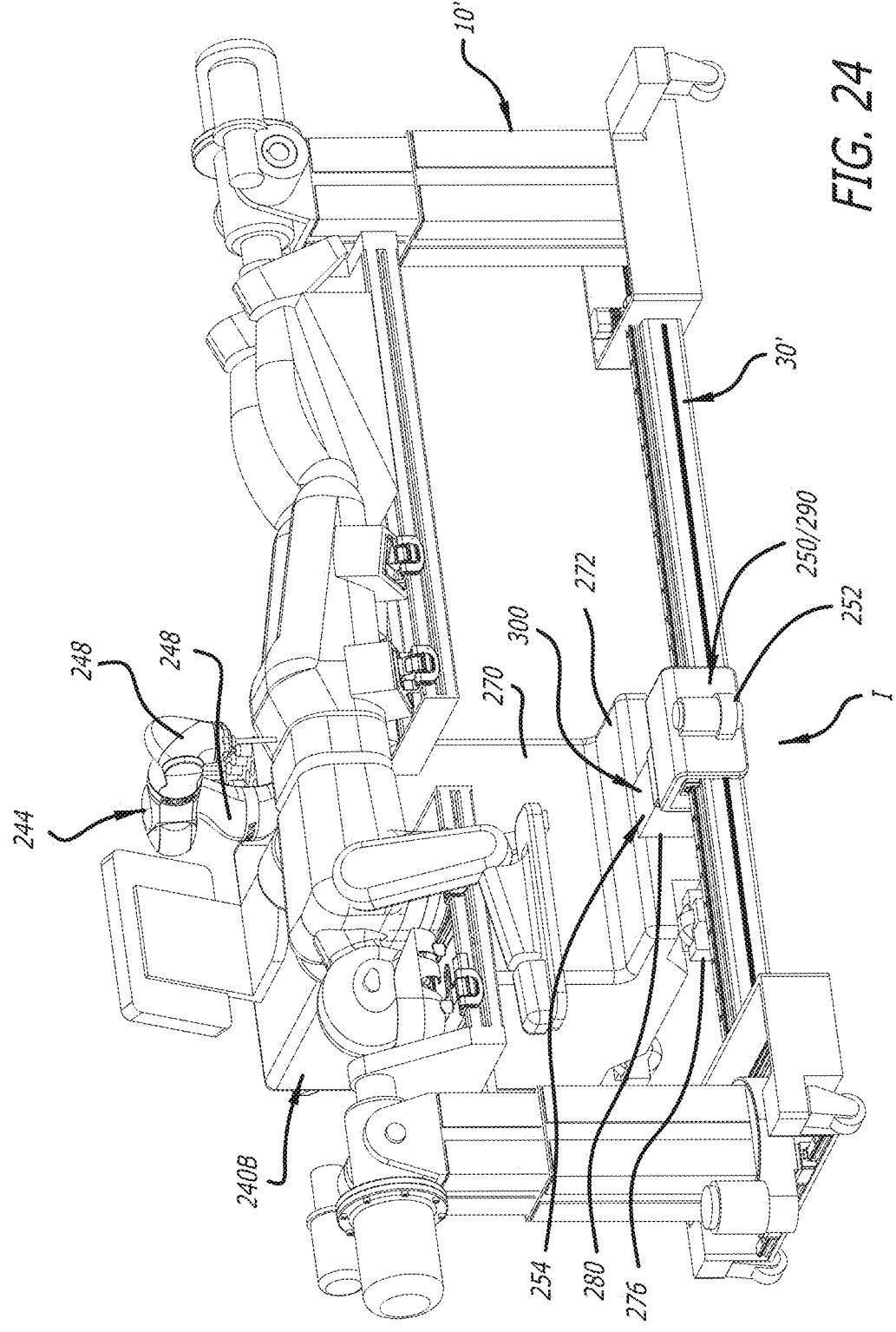
FIG. 24 is a side, perspective view, similar to FIG. 23, of the second cart portion of FIG. 22 being interconnected with the surgical table of FIG. 13 supporting the patient thereon that illustrates the second cart portion and the surgical robotic system positioned in a second position relative to the surgical table and the patient.

A preferred embodiment of a docking interface of the present disclosure is generally indicated by the letter I in FIGS. 13-24. Portions of the interface I can be incorporated on a modified version of the surgical table 10 (discussed hereinabove) referenced by the identifier 10' and in a surgical-equipment cart portions 240A or 240B. As depicted in FIGS. 13, 14, 17-21, 23, and 24, the surgical table 10' can include similar features to the surgical table 10, and identical numbering will be used to denote these similar features. The cart portions 240A or 240B can be attached and detached relative to the surgical table 10' using the docking interface I. The cart portion 240A, as depicted in FIGS. 16-21, can be used to support an imaging device 242, and the cart portion 240B, as depicted in FIGS. 22-24, can be used to support a surgical robot 244. The imaging device 242 and the surgical robot 244 can be supported by and/or integrated with the cart portions 240A and 240B, respectively. The imaging device 242, for example, can be an O-arm 246, and the surgical robot 244 can include one or more articulable arm portions 248. While the interface I is depicted in FIGS. 13-15, 17-21, 23, and 24 as being used with the surgical table 10', the interface I is not so limited, and the interface I can be used with other surgical tables.

As discussed below, portions of the interface I incorporated on the surgical table 10' and the cart portions 240A and 240B, and these portions can be positioned relative to and then docked with one another. As discussed below, the docking of the surgical table 10' moveably interconnects to the surgical table 10' and the surgical carts 240A or 240B to one another. Thereafter, the interface I affords controlled movement of the surgical table 10' relative to the surgical carts 240A or 240B, or movement of the surgical carts 240A or 240B relative to the surgical table 10'. The controlled movement afforded by the interface I can be used to position and reposition a patient P supported by the surgical table 10' and the imaging device 242 or the surgical robot 244 relative to one another in a cranial-caudal direction.

As such, the patient P supported by the surgical table 10' and the surgical carts 240A or 240B can be positioned and repositioned relative to one another before, during, and after surgery to adjust the position of the imaging device 242 or the surgical robot 244 so that the imaging device 242 or the surgical robot 244 can aid and/or perform surgery on the patient P. The imaging device 242 and the surgical robot 244 can reach significant portions of the bony anatomy of the patient P using the interface I, the surgical table 10', and surgical carts 240A and 240B.

As depicted in FIGS. 13-15, 17-21, 23, and 24, the interface I includes a first portion 250 attached and/or supported relative to the surgical table 10' that can include an actuator 252 actuatable to facilitate movement of the surgical table 10' relative to the surgical carts 240A or 240B, or movement of the surgical carts 240A or 240B relative to the surgical table 10'. Furthermore, as depicted in FIGS. 16-19 and 22-24, the interface I also includes a second portion 254 incorporated on or relative to the to the cart portions 240A and 240B. The first portion 250 and the second portion 254 of the interface I can be engaged to one another to moveably attach the surgical table 10' and the cart portions 240A and 240B relative to one another.

As depicted in FIGS. 16-19, the cart portion 240A includes a base portion 260, a shoulder portion 262, a set of wheels 264, and a set of casters 266. The shoulder portion 262 extends outwardly from the base portion 260, and the second portion 254 of the interface I can be attached and/or supported relative to the shoulder portion 262. And the shoulder portion 262, along with the base portion 260, also supports the imaging device 242 thereon. As depicted in FIGS. 16-21, the imaging device 242 is the O-arm 246, but the imaging device 242, for example, also could be a C-arm or other imaging device supported by the cart portion 240A. A first wheel of the set of wheels 264 can be positioned adjacent a first side of the cart portion 240A, a second wheel of the set of wheels 264 can be positioned adjacent a second side of the cart portion 240A, a first caster of the set of casters 266 can be positioned adjacent the first side of the cart portion 240A, and a second caster of the set of casters 266 can be positioned adjacent the second side of the cart portion 240A. Using the set of wheels 264 and the set of casters 266, the cart portion 240A can be positioned and repositioned relative to the surgical table 10'. The surgical table 10' can likewise be moved relative to the cart portion 240A using the casters 68 and 120 of the surgical table 10'.

As depicted in FIGS. 22, the cart portion 240B includes a base portion 270, a shoulder portion 272, a first set of casters 274, and a second set of casters 276. The shoulder portion 272 extends outwardly from the base portion 270, and the second portion of the 254 of the interface I can be attached and/or supported relative to the shoulder portion 272. As depicted in FIGS. 22-24, the surgical robot 244 can include the articulatable arm portions 248. A first caster of the first set of casters 274 and a first caster of the second set of casters 276 can be positioned on a first side of the cart portion 240B, and a second caster of the first set of casters 274 and a second caster of the second set of casters 276 can be positioned on a second side of the cart portion 240B. Using the first set of casters 274 and the second set of casters 276, the cart portion 240B can be positioned and repositioned relative to the surgical table 10. The surgical table 10' can likewise be moved relative to the cart portion 240B using the casters 68 and 120 of the surgical table 10'.

The second portion 254 of the interface I attached and/or supported relative to the cart portions 240A and 240B can include a neck portion 280 and an extension portion 282. For example, the neck portion 280 and the extension portion 282 can be provided on the shoulder portion 272, and the extension portion 282 can be moved inwardly and outwardly relative to the neck portion 280 between a first inward portion (FIG. 16) and a second outward portion (FIG. 17). The extension portion 282 includes an end portion 284 and a bolt-receiving aperture 286 formed in the end portion 284. Using the inward and outward movement of the extension portion 282, the end portion 284 can be positioned relative to the first portion 250 of the interface I attached and/or supported relative to the surgical table 10'. As discussed below, the end portion 284 can be lockably engaged to a portion of the first portion 250 of the interface I.

Figure 15:
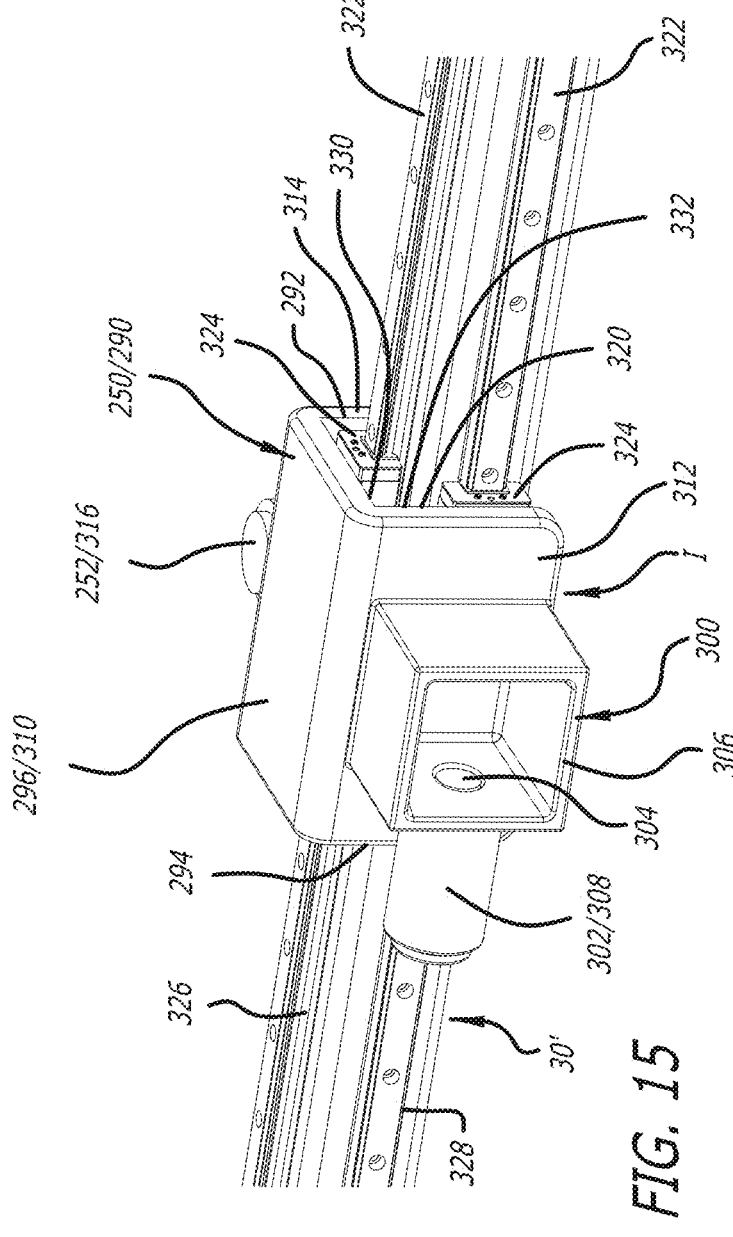
FIG. 15 is a side, perspective view of the collar portion included on the surgical table of FIG. 13 that illustrates the collar portion and a locking mechanism included on the collar portion.
Figure 16:
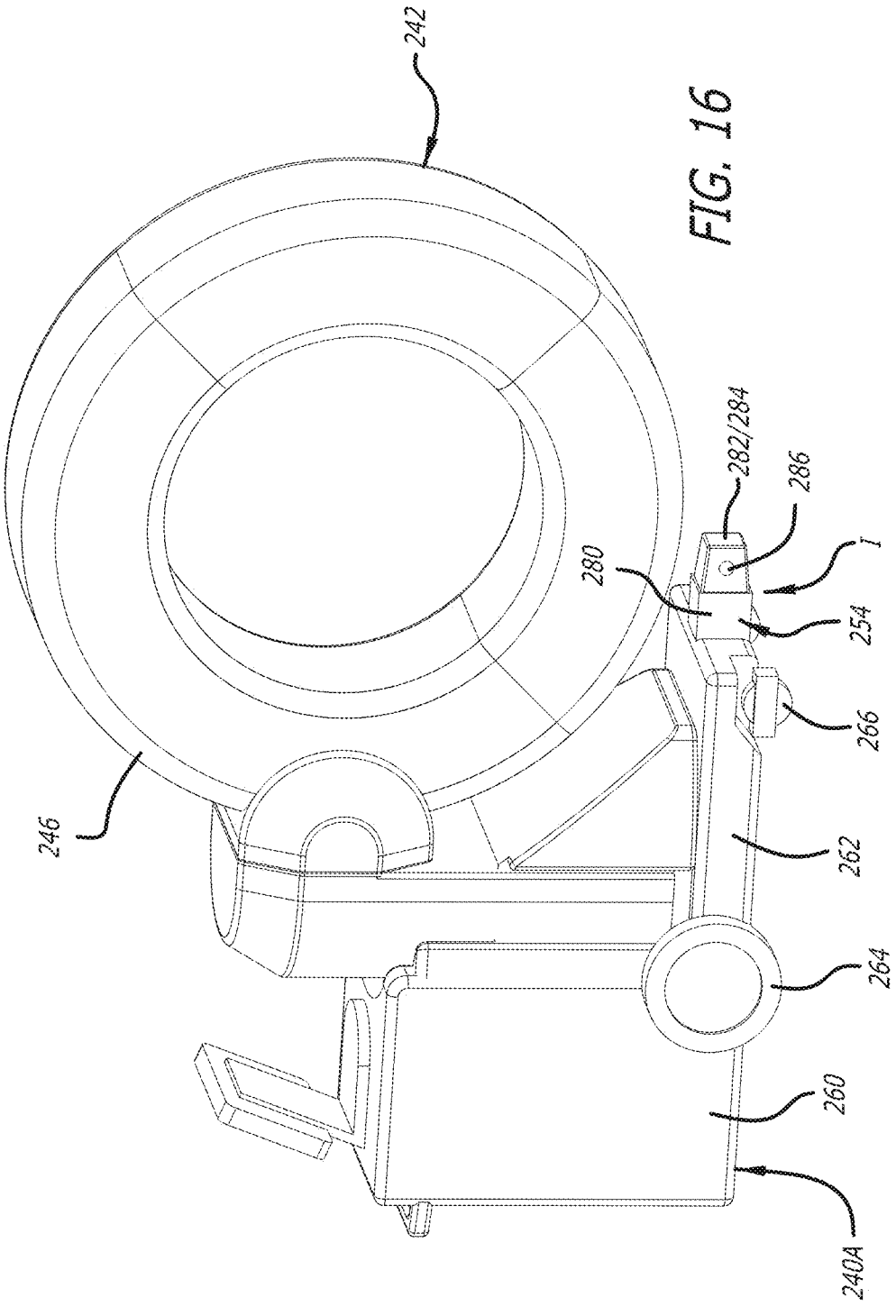
FIG. 16 is a side, perspective view of a first cart portion of the present disclosure that illustrates the cart portion incorporating an imaging device and an extension portion of the interface thereon.
Figure 17:
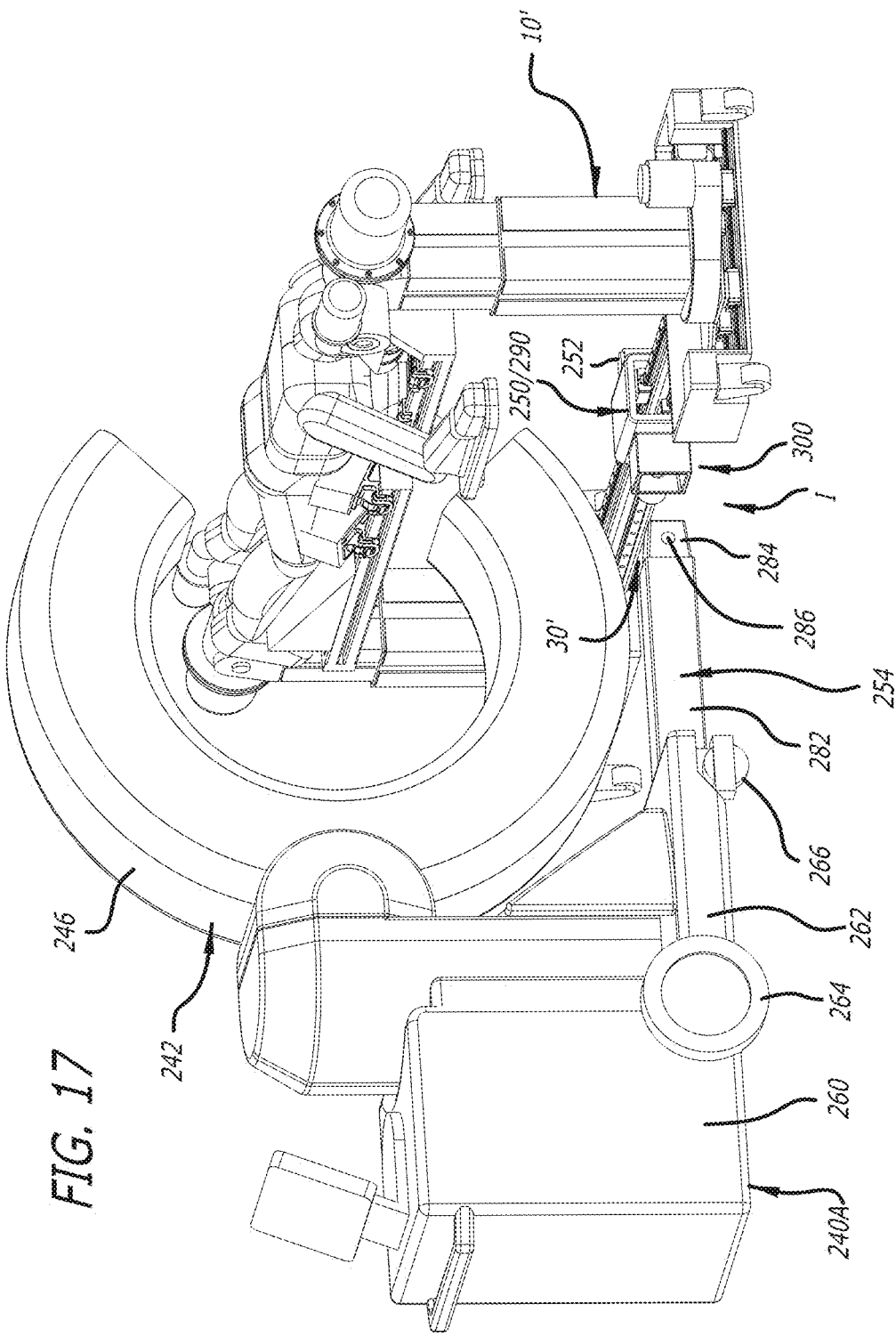
FIG. 17 is a side, perspective view of the first cart portion of FIG. 16 being positioned relative to the surgical table of FIG. 13 supporting the patient thereon that illustrates the extension portion of the interface being extended to engage the collar portion of the interface.

As depicted in FIGS. 15-17, for example, the first portion 250 of the interface I can include a collar portion 290 attached to and moveably supported by the surgical table 10'. As discussed below, a modified longitudinal cross member 30' of the horizontally-oriented portion 20 of the support portion 16 of the surgical table 10' is received through the collar portion 290. The collar portion 290 includes a first end 292, a second end 294, and a body portion 296 extending between the first end 292 and the second end 294. Furthermore, the collar portion 290 also includes a receiver portion 300, a locking actuator 302, and a locking bolt 304. The receiver portion 300 is provided on the body portion 296, and the receiver portion 300 includes a recess 306 with the locking bolt 304 being moveable into and out of the recess 306 via actuation of the locking actuator 302, and the locking actuator 302 includes a housing 308 attached to the receiver portion 300. When the end portion 284 is received in the recess 306, actuation of the locking actuator 302 can move the locking bolt 304 into position within the bolt-receiving aperture 286. And receipt of the locking bolt 304 in the bolt-receiving aperture 286 serves to securely attach the first portion 250 and the second portion 254 of the interface I to one another.

Although, as described above, the bolt-receiving aperture 286 is provided on the end portion 284, and the locking bolt 304 is moveable into and out of the recess 306, the present disclosure is not so limited. Instead, a locking bolt that is similar to locking bolt 304 could be provided on a first modified end portion that is similar to the end portion 284, and be moveable out of and into the first modified end portion. Furthermore, a bolt-receiving aperture that is similar to the bolt-receiving aperture 286 could be provided in a first modified receiver portion and a first modified recess that are similar to the receiver portion 300 and the recess 306. Thus, when the first modified end portion is received in the first modified recess, the locking bolt provided on the first modified end portion can be actuated and moved into the bolt-receiving aperture of the first modified receiver portion to facilitate engagement therebetween and attachment of the first portion 250 and the second portion 254 of the interface I to one another.

Furthermore, although, as described above, the end portion 284 provided on the extension portion 282 is received in the recess 306, the present disclosure is not so limited. Instead, a second modified receiver portion and a second modified recess similar to the receiver portion 300 and the recess 306 could be provided on the extension portions 282, and a second modified end portion similar to the end portion 284 could be provided on the collar portion 290. As such, the second modified end portion provided on the collar portion 290 can be received in the second modified recess of the second modified receiver portion provided on the extension portion 282. And the locking bolts and bolt-receiving apertures, as described above, whether respectively positioned in/on the second modified receiver portion and the second modified end portion, or vice versa, can be engaged to facilitate engagement therebetween and attachment of the first portion 250 and the second portion 254 of the interface I to one another.

With the first portion 250 and the second portion 254 are securely engaged to one another, the actuator 252 can be actuated to facilitate movement of the surgical table 10' and the surgical carts 240A or 240B relative to one another. The actuator 252, as depicted in FIG. 15, is attached to the collar portion 290, and can include a motor and a transmission (not shown). Actuation of the actuator 252 facilitates movement of the collar portion 290 and the cross member 30' relative to one another. When the first portion 250 and the second portion 254 are securely engaged to one another, the relative movement of the collar portion 290 and the cross member 30' also facilitates positioning and repositioning the surgical table 10' and the surgical carts 240A or 240B relative to one another. And as discussed above, such movement correspondingly can be used to adjust the position of the patient P supported by the surgical table 10' relative to the imaging device 242 and the surgical robot 244 before, during, and after surgery.

The body portion 296 includes an upper wall 310, a first sidewall 312, and a second sidewall 314, and the actuator 252 includes a housing 316 that can be attached to the second sidewall 314. The modified cross member 30', as discussed above, of the horizontally-oriented portion 20 of the support portion 16 is received through the collar portion 290. To that end, as depicted in FIG. 15, the body portion 296 includes a cavity 320 extending between the first end 292 and the second end 294 for receiving the modified cross member 30'. The cavity 320 can be defined at least in part by the upper wall 310, the first sidewall 312, and the second sidewall 314. During movement of the cross member 30' relative collar portion 290, portions of the cross member 30' move into and out of the cavity 320.

To facilitate movement of the collar portion 290 and the cross member 30' relative to one another, portions of the cross member 30', as depicted in FIG. 15, can include one or more tracks 322, and portions of the collar portion 290 can include one or more trucks 324 for operatively engaging the tracks 322. The operative engagement of the trucks 324 to the tracks 322 allows the cross member 30' to move relative to the collar portion 290 by sliding within the cavity 320. The tracks 322 can be provided on an upper surface 326 and a side surface 328 of the cross member 30'. To operatively engage the tracks 322, the one or more trucks 324 can be provided on an inner surface 330 of the upper wall 310 and an inner surface 332 of the first sidewall 312. The one or more trucks 324 provided on the inner surface 330 of the upper wall 310 engage the track 322 provided on the upper surface 326, and the one or more trucks 324 provided on the inner surface 332 of the first sidewall 312 engage the track 322 provided on the side surface 328.

A first gear portion in the form of circular gear (or pinion) (not shown) can be provided in the cavity 320 and driven by the actuator 252, and, in addition to the tracks 312, a second gear portion in the form of a linear gear (or rack) 334 can be provided on the modified cross member 30'. As depicted in FIGS. 23 and 24, the linear gear 334 can be provided on a side surface 336 of the cross member 30'. Furthermore, the circular gear can be attached to a shaft (not shown) that extends through the second sidewall 314, and the shaft can be rotated by operation of the actuator 252. The circular gear can be engaged to the linear gear 334, and rotation of the circular gear via actuation of the actuator 252 serves to move the cross member 30' relative to the collar portion 290. For example, rotation of the circular gear in a first rotational direction can move the cross member 30' in a first linear direction relative to the collar portion 290, and rotation of the circular gear in an opposite rotational direction can move the cross member 30' in an opposite second linear direction relative to the collar portion 290.

When the first portion 250 and the second portion 254 of the interface I are securely engaged to one another, rotation of the circular gear (via actuation of the actuator 252) serves to move the cross member 30' and the collar portion relative to one another, and correspondingly adjusts the position of the surgical table 10' and the surgical carts 240A or 240B relative to one another. As such, actuation of the actuator 252 and the interface I affords controlled movement of the surgical table 10' relative to the surgical carts 240A or 240B, or controlled movement of the surgical carts 240A or 240B relative to the surgical table 10'. Accordingly, the surgical table 10' and the surgical carts 240A or 240B can be positioned and repositioned relative to one another to correspondingly adjust the position the imaging device 242 or the surgical robot 244 relative to the patient P supported by surgical table 10'. Thus, such adjustment allows the patient P and the imaging device 242 or the surgical robot 244 relative to one another to be positioned and repositioned relative to one another in a cranial-caudal direction before, during, and after surgery to perform and/or aid the performance of surgery on the patient P.

During use thereof, the surgical table 10' and the surgical carts 240A or 240B can be brought into position relative to one another. Thereafter, the first portion 250 and the second portion 254 of the interface I can be engaged with one another. In doing so, the end portion 284 of the extension portion 282 can be received in the recess 306 of the receiver portion 300, and then the locking actuator 302 can be actuated to move the locking bolt 304 into the bolt-receiving aperture 286. If necessary, the extension portion 282 can be moved inwardly and/or outwardly using an actuator (not shown) to facilitate receipt of the end portion 284 into the recess 306 of the receiver portion 300, and movement of the surgical carts 240A or 240B relative to the surgical table 10'. With the first portion 250 and the second portion 254 of the interface I are securely engaged to one another, the actuator 252 can be actuated to move the cross member 30' and the collar portion 290 relative to one another, and in doing so, facilitate controlled movement of the surgical table 10' and the surgical carts 240A or 240B relative to one another. Such controlled movement correspondingly adjusts the position the imaging device 242 or the surgical robot 244 relative to the patient P supported by surgical table 10' relative to the cross member 30' in a cranial-caudal direction. Furthermore, the extension portion 282 can be used to move the imaging device 242 or the surgical robot 244 in a transverse direction to the cranial-caudal direction.

Figure 18:
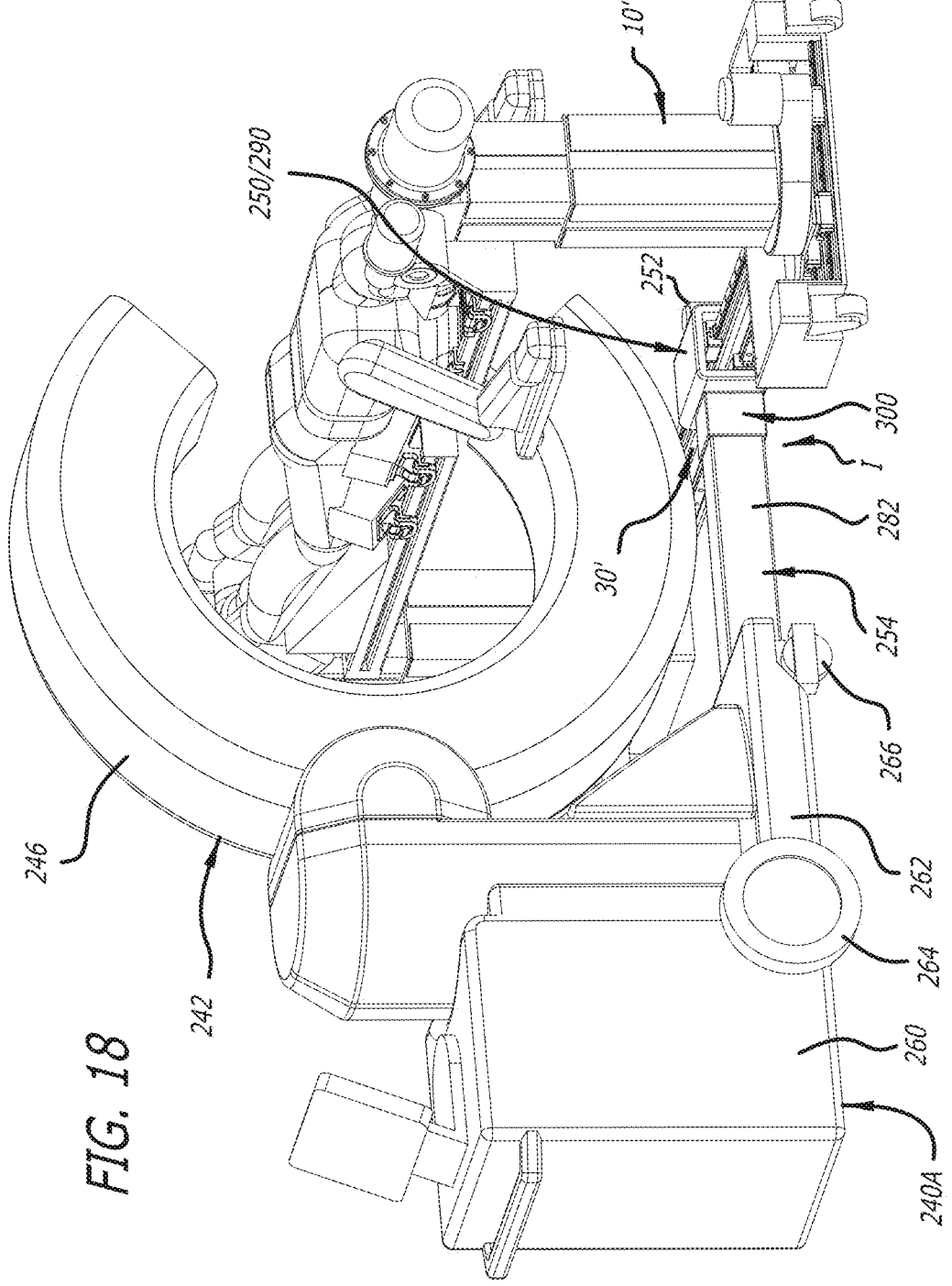
FIG. 18 is a side, perspective view, similar to FIG. 17, of the first cart portion of FIG. 16 being interconnected with the surgical table of FIG. 13 supporting the patient thereon that illustrates the extension portion of the interface being initially interconnected with the collar portion of the interface.
Figure 19:
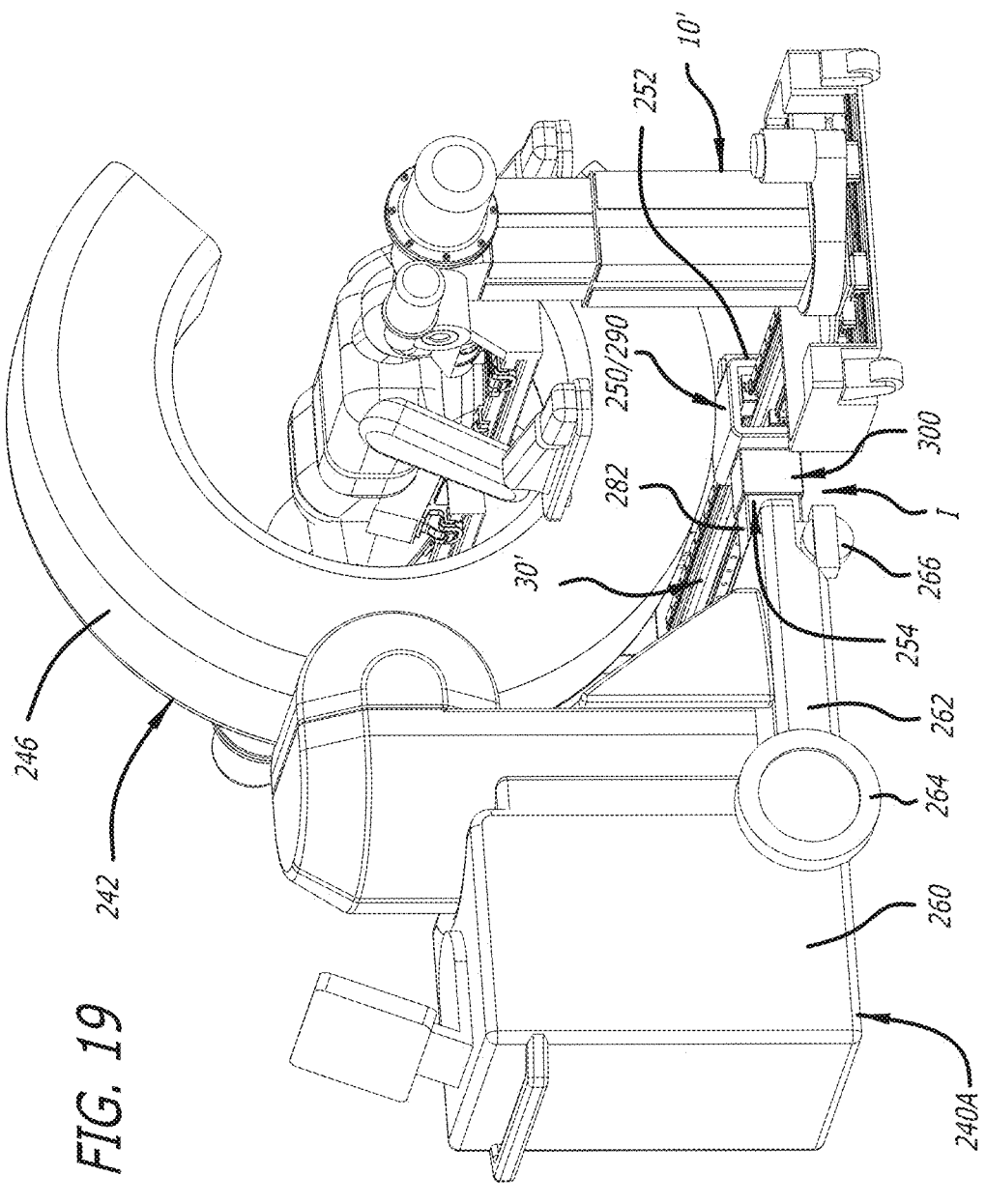
FIG. 19 is a side, perspective view, similar to FIG. 17, of the first cart portion of FIG. 16 being interconnected with the surgical table of FIG. 13 supporting the patient thereon that illustrates the collar portion and the extension portion of the interface being interconnected and portions of the surgical table and the patient positioned within the imaging device.
Figure 20:
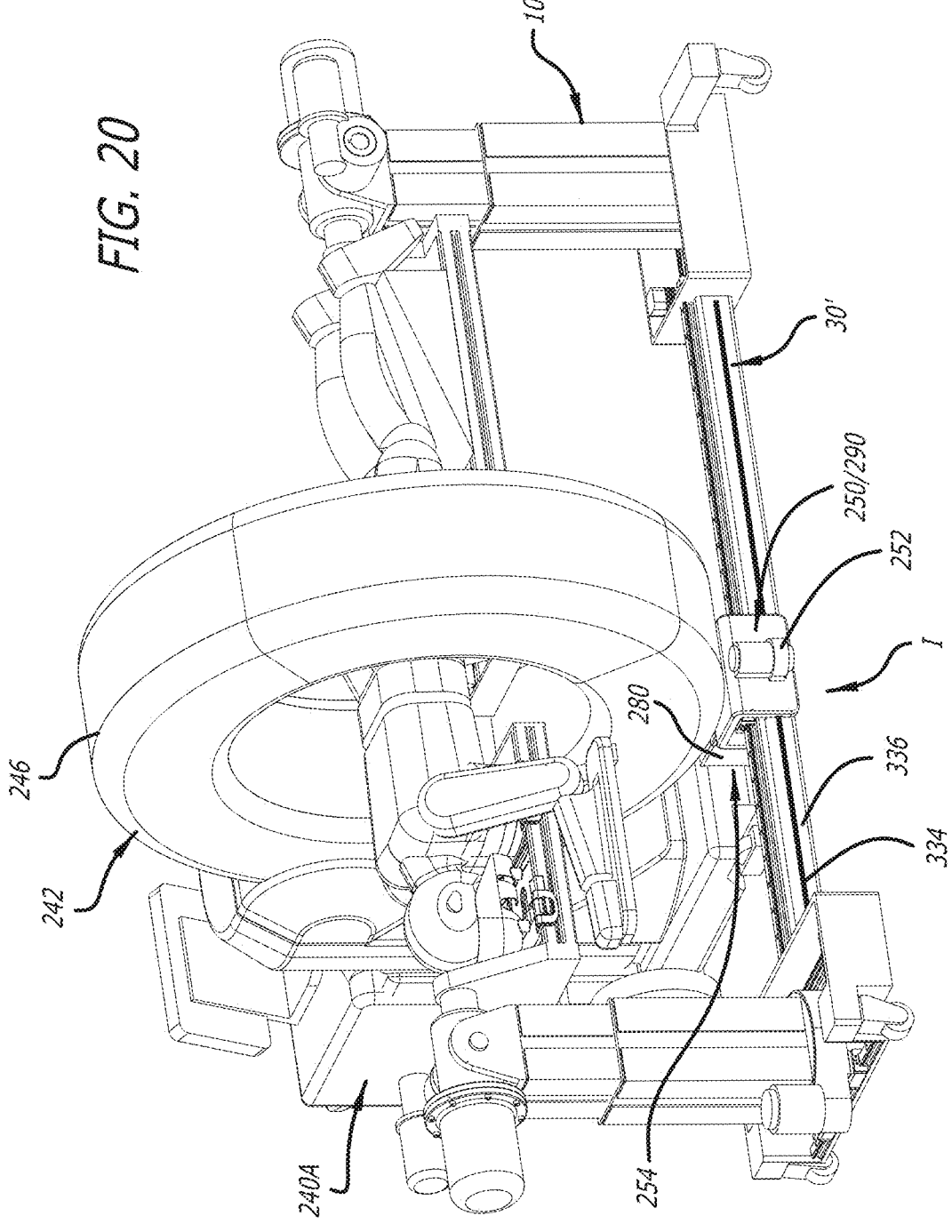
FIG. 20 is a side, perspective view of the first cart portion of FIG. 16 being interconnected with the surgical table of FIG. 13 supporting the patient thereon that illustrates portions of the surgical table and the patient positioned within the imaging device, and with the first cart portion and the imaging device positioned in a first position relative to the surgical table and the patient.
Figure 21:
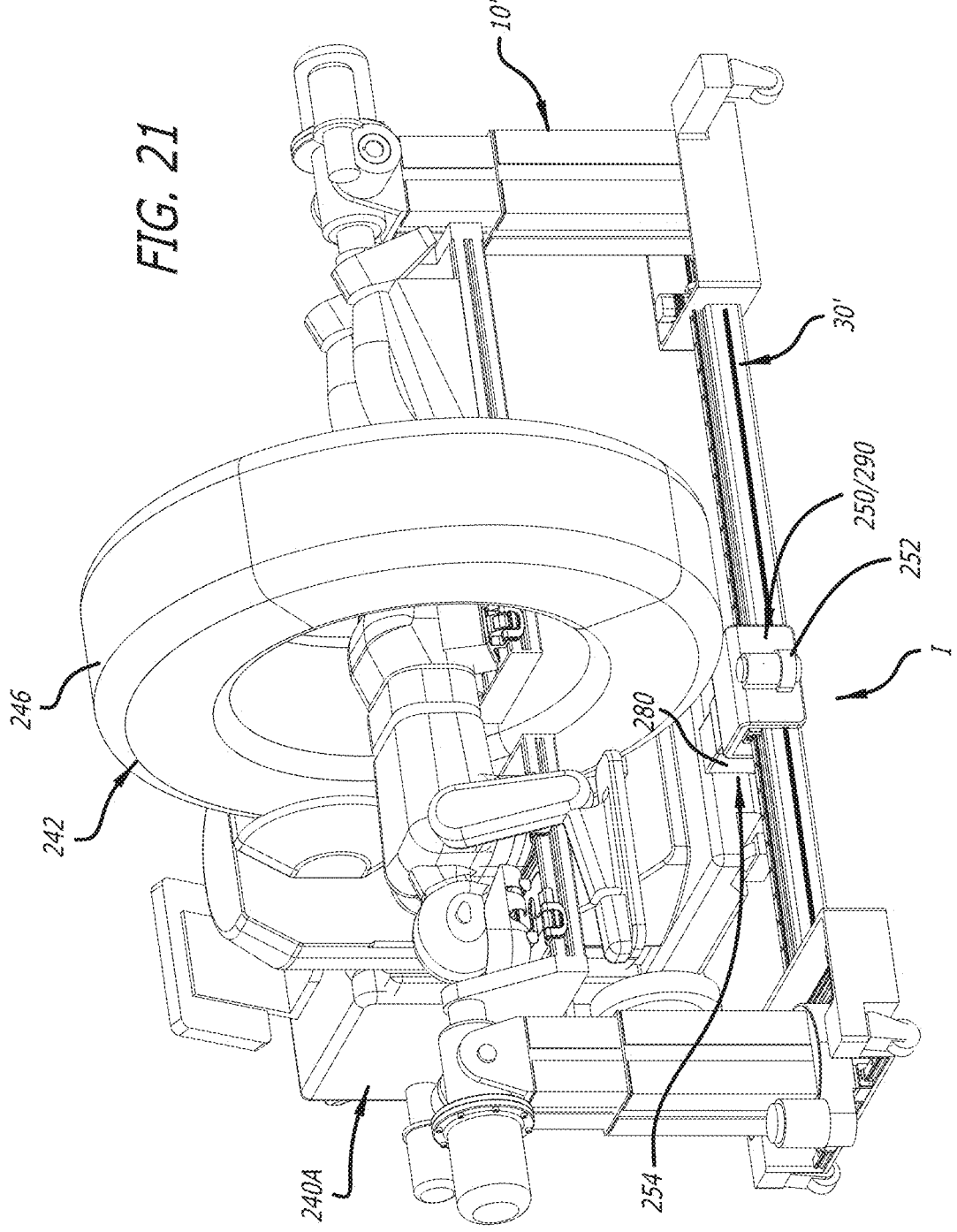
FIG. 21 is a side, perspective view, similar to FIG. 20, of the first cart portion of FIG. 16 being interconnected with the surgical table of FIG. 13 supporting the patient thereon that illustrates portions of the surgical table and the patient positioned within the imaging device, and with the first cart portion and the imaging device positioned in a second position relative to the surgical table and the patient.

Using the surgical cart 240A that supports the imaging device 242, the imaging device 242 can be positioned relative to the patient P. To engage the surgical cart 240A and the surgical table 10' relative to one another, the imaging device 242, when it is the O-arm 246, can be opened (as depicted in FIG. 17) and the surgical cart 240A initially can be positioned relative to the surgical table 10' and the patient P supported thereby. The extension portion 282 can be moved inwardly and/or outwardly to facilitate receipt of the end portion 284 into the recess 306 of the receiver portion 300. When the first portion 250 and the second portion 254 of the interface I are engaged to one another, the extension portion 282 can be moved inwardly relative to the neck portion 280 to position the patient P supported by the surgical table 10' into the imaging device 242, when it is the O-arm 246 (as depicted in FIGS. 18 and 19). Then, the imaging device 242, when it is the O-arm 246, can be closed (as depicted in FIG. 20) around the patient P, and the surgical cart 240A and the surgical table 10' (and the patient P supported thereby) can be moved relative to one another, so that the imaging device 242, when it is the O-arm 246, can reach significant portions of the bony anatomy of the patient P. The surgical table 10' can remain stationary relative to the floor by locking the casters 68 and 120, so that the surgical cart 240A (and the imaging device 242) can move relative to the surgical table 10' and the patient P supported thereby via actuation of the actuator 252. Alternatively, the surgical cart 240A (and the imaging device 242) can remain stationary relative to the floor by locking the set of wheels 264 and the set of casters 266, so that the surgical table 10' and the patient P supported thereby can move relative to the surgical cart 240A via actuation of the actuator 252.

Using the surgical cart 240B that supports the surgical robot 244, the articulatable arm portions 248 of the surgical robot 244 can be moved relative to the patient P. To engage the surgical cart 240B and the surgical table 10' relative to one another, the surgical cart 240B initially can be positioned relative to the surgical table 10' and the patient support thereby. The extension portion 282 can be moved inwardly and/or outwardly to facilitate receipt of the end portion 284 into the recess 306 of the receiver portion 300. When the first portion 250 and the second portion 254 of the interface I are engaged to one another, the extension portion 282 can be moved inwardly relative to the neck portion 280 to position the articulable arm portions 248 of the surgical robot 244 relative to the patient P supported by the surgical table 10'. Then, the surgical cart 240B and the surgical table 10' (and the patient P supported thereby) can be moved relative to one another, so that the articulable arm portions 248 of the surgical robot 244 can reach significant portions of the body anatomy of the patient P. The surgical table 10' can remain stationary relative to the floor by locking the casters 68 and 120, so that the surgical cart 240B (and the surgical robot 244) can move relative to the surgical table 10' and the patient P supported thereby via actuation of the actuator 252. Alternatively, the surgical cart 240B (and the surgical robot 244) can remain stationary relative to the floor by locking the first set of casters 274 and the second set of casters 276, so that the surgical table 10' and the patient P supported thereby can move relative to the surgical cart 240B via actuation of the actuator 252.

A surgical cart or cart portion 400, similar to the cart portion 240B, is depicted in FIGS. 25-37, and includes a radiographic imaging device 402 and a first robotic arm 404 supported thereby. Like the cart portion 240B, the cart portion 400 can include the second portion 254 of the interface I attached thereto and/or supported thereby to facilitate interconnection of the cart portion 400 with the first portion 250 of the interface I attached to and/or supported by the surgical table 10'. The engagement of the first portion 250 and the second portion 254 of the interface I facilitate this interconnection.

Figure 25:
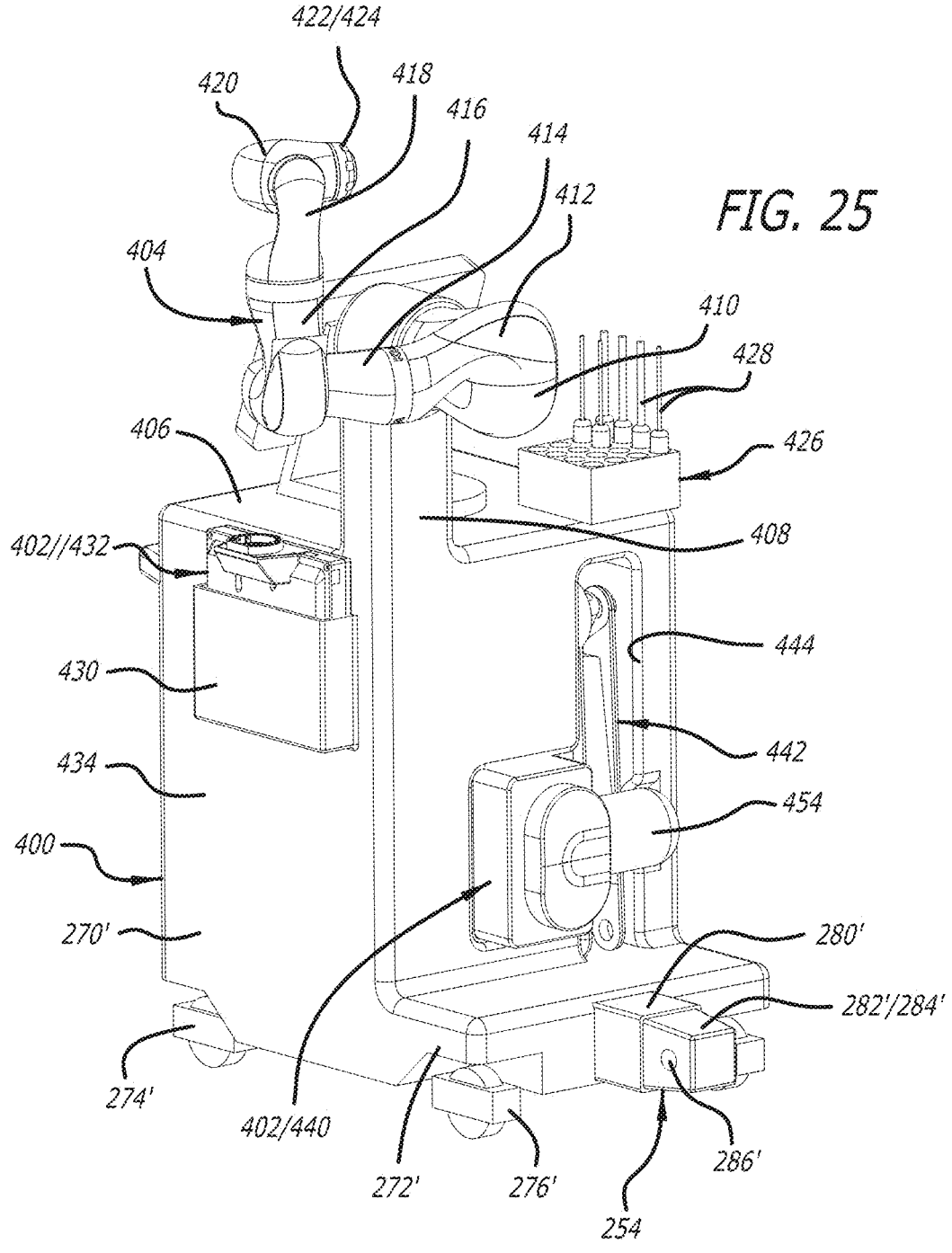
FIG. 25 is a front and first lateral side, perspective view of a surgical cart or cart portion of the present disclosure including a portion of an interface facilitating moveable interconnection with a surgical table, and supporting two surgical robotic arms thereon with a first robotic arm in a disengaged position, and a second robotic arm supporting a portion of an imaging system thereon in an unextended position.
Figure 26:
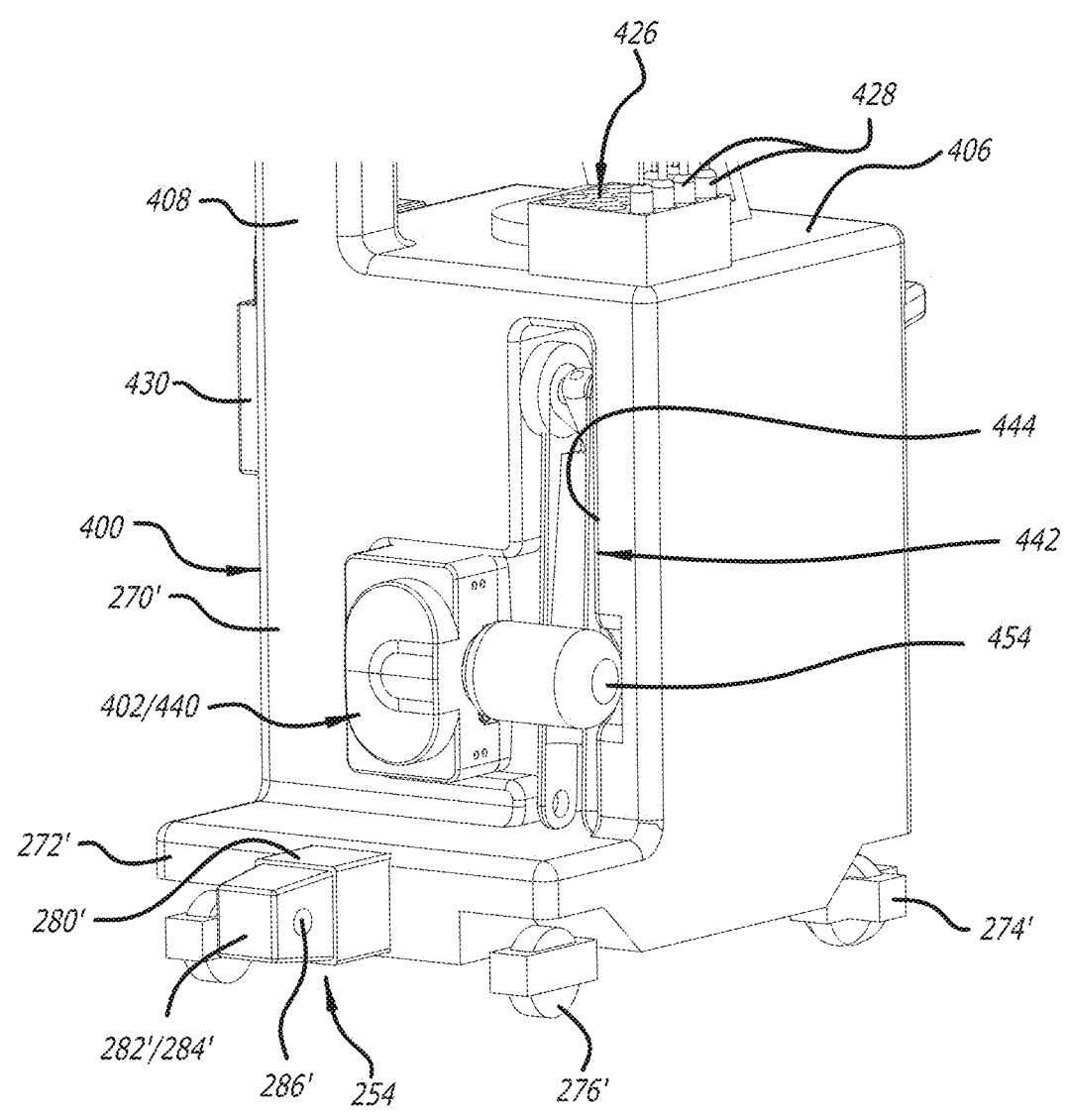
FIG. 26 is a front and second lateral side, partial, perspective view of the surgical cart of FIG. 25 that illustrates the second robotic arm supporting the portion of the imaging system thereon in the unextended position.
Figure 27:
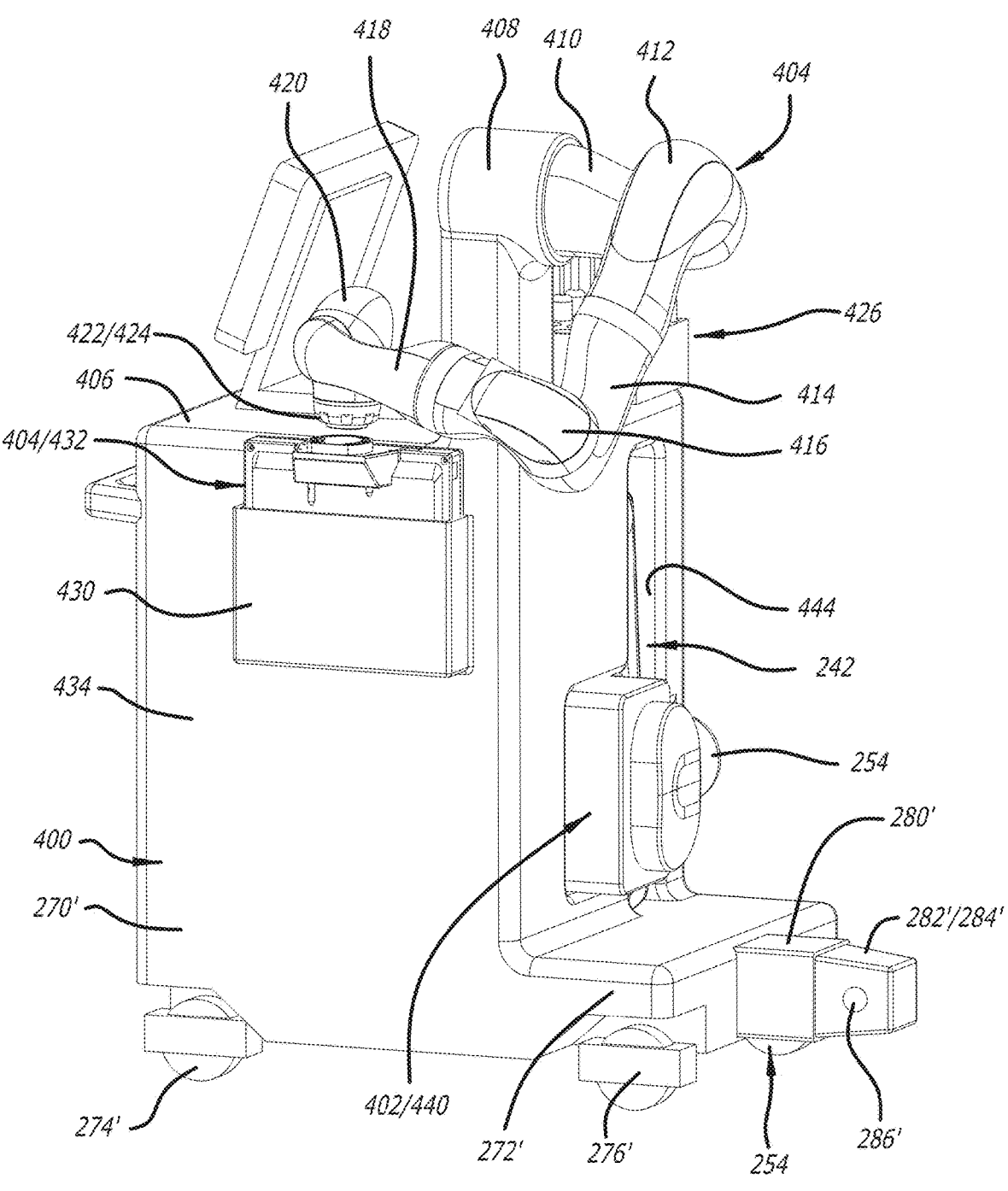
FIG. 27 is a first lateral side, perspective view of the of the surgical cart of FIG. 25 that illustrates positioning of the first robotic arm into an engaged position relative to another portion of the imaging system.
Figure 28:
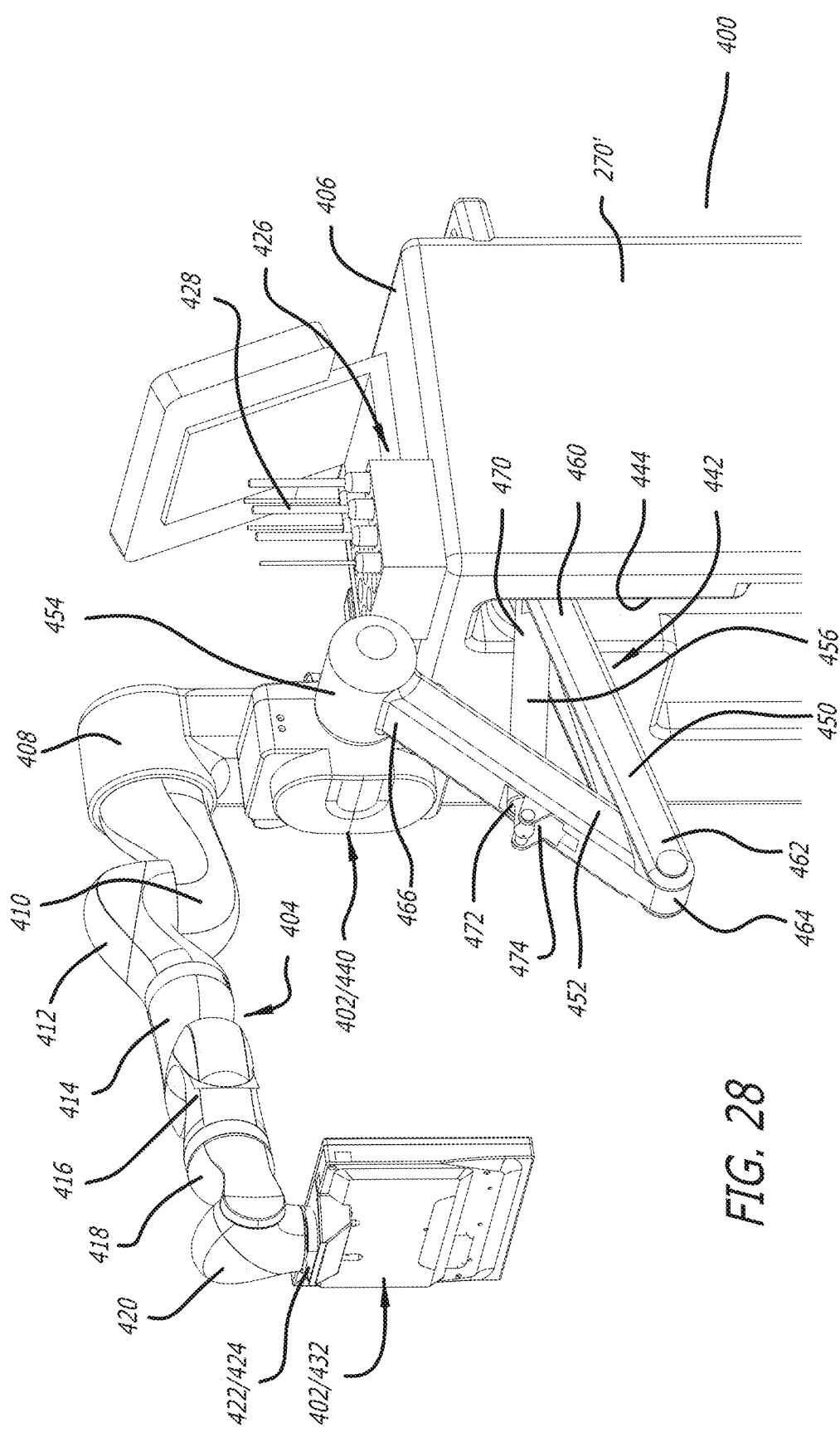
FIG. 28 is a front and second lateral side, partial, perspective view of the surgical cart of FIG. 25 that illustrates the first robotic arm and the second arm supporting the portions of the imaging system oriented such that radiographic energy is directed horizontally therebetween.
Figure 29:
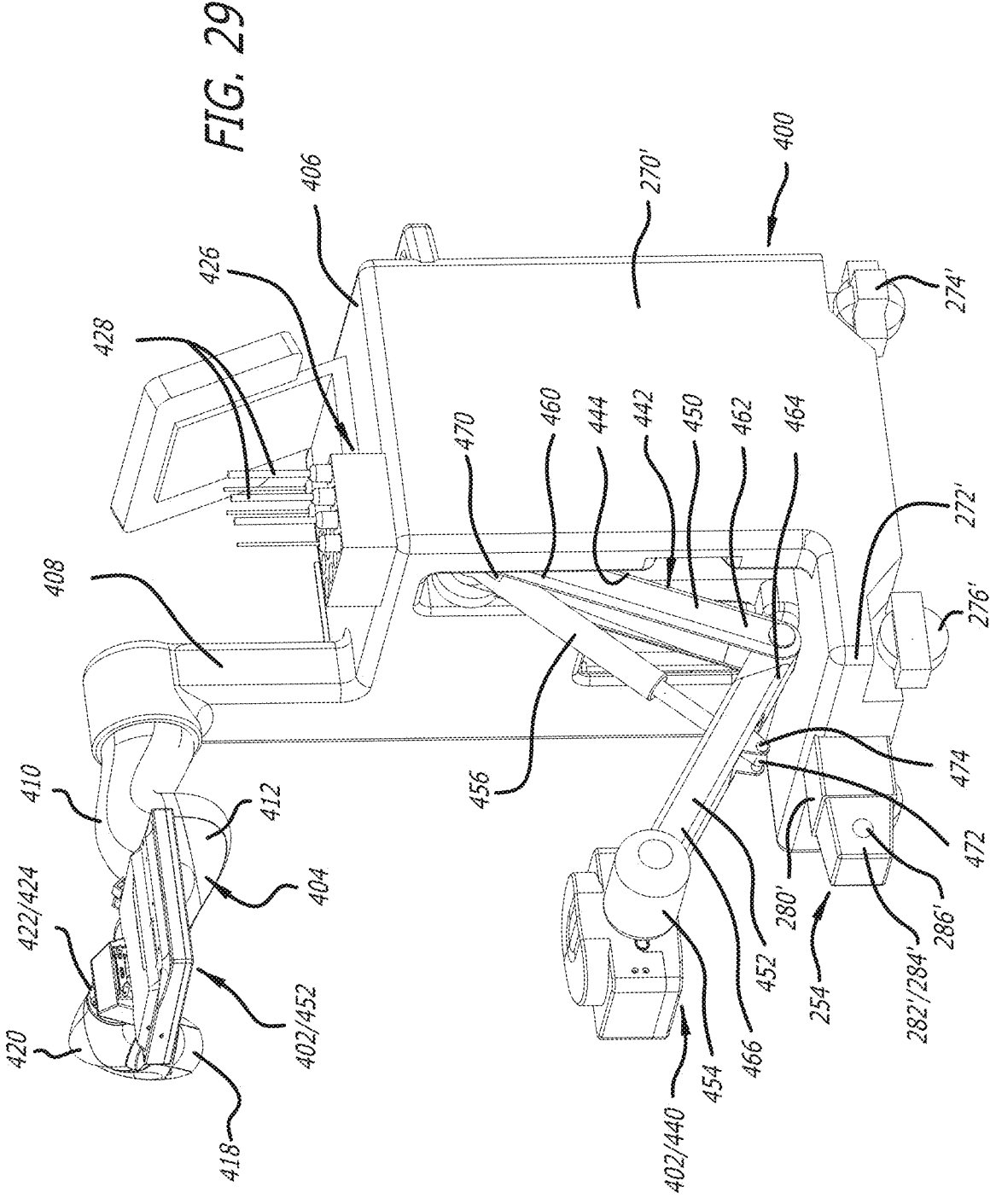
FIG. 29 is a front and second lateral side, perspective view of the surgical cart of FIG. 25 that illustrates the first robotic arm and the second robotic arm supporting the portions of the imaging system oriented such that the radiographic energy is directed vertically therebetween.
Figure 30:
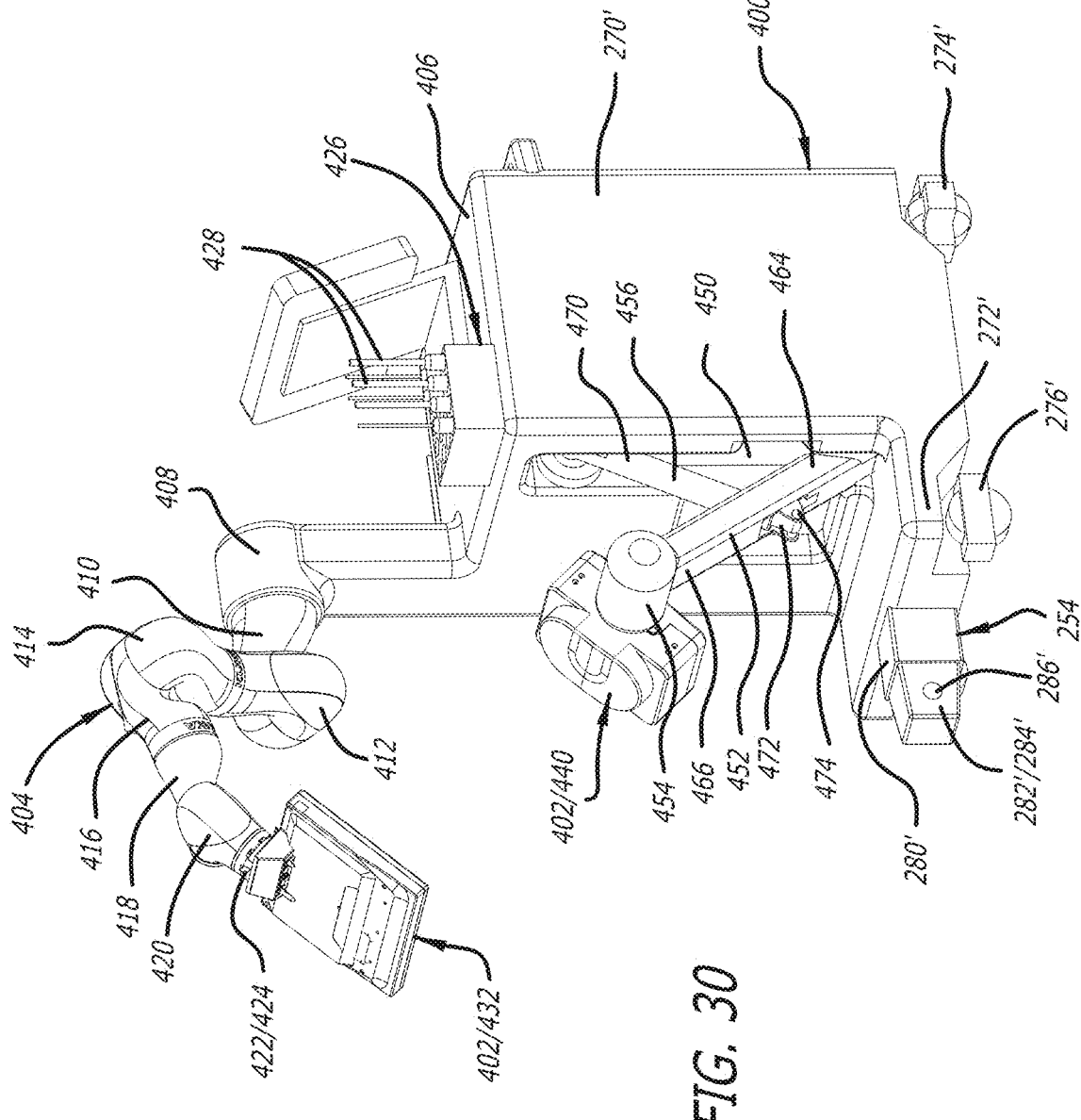
FIG. 30 is a front and second lateral side, perspective view of the surgical cart of FIG. 25 that illustrates the first robotic arm and the second robotic arm supporting portion of the imaging system oriented such that the radiographic energy is directed in a first diagonal direction therebetween.
Figure 31:
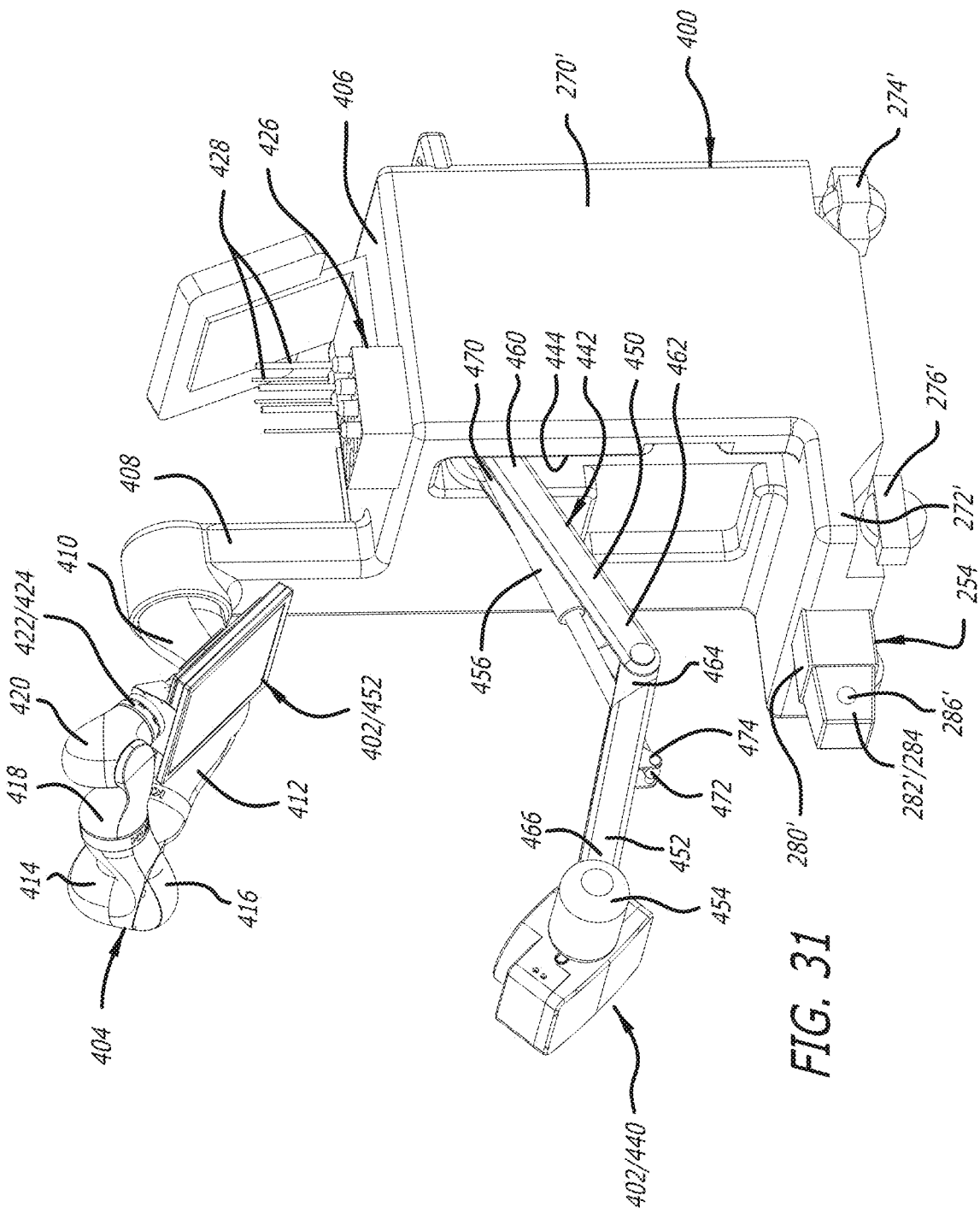
FIG. 31 is a front and second lateral side, perspective view of the surgical cart of FIG. 25 that illustrates the first robotic arm and the second robotic arm supporting portion of the imaging system oriented such that the radiographic energy is directed in a second diagonal direction therebetween.

The cart portion 400 shares many similar features with the cart portion 240B, and similar numbering will be used to denote these similar features. Like the cart portion 240B, as depicted in FIGS. 25-27, the cart portion 400 includes a base portion 270', a shoulder portion 272', a first set of casters 274', and a second set of casters 276'. The base portion 270' supports the imaging device 402 and the first robotic arm 404. Furthermore, the shoulder portion 272' extends outwardly from the base portion 270', and the second portion of the 254 of the interface I can be attached and/or supported relative to the shoulder portion 272'. A first caster of the first set of casters 274' and a first caster of the second set of casters 276' can be positioned on a first side of the cart portion 400, and a second caster of the first set of casters 274' and a second caster of the second set of casters 276' can be positioned on a second side of the cart portion 400. Using the first set of casters 274' and the second set of casters 276', the cart portion 400 can be positioned and repositioned relative to the surgical table 10'.

The second portion 254 of the interface I attached and/or supported relative to the cart portion 400 can include a neck portion 280' and an extension portion 282'. For example, the neck portion 280' and the extension portion 282' can be provided on the shoulder portion 272', and the extension portion 282' can be moved inwardly and outwardly relative to the neck portion 280' between a first inward portion and a second outward portion. The extension portion 282' includes an end portion 284' and a bolt-receiving aperture 286' formed in the end portion 284'. Using the inward and outward movement of the extension portion 282', the end portion 284' can be positioned relative to the first portion 250 of the interface I attached and/or supported relative to the surgical table 10'. As discussed below, the end portion 284' can be lockably engaged to a portion of the first portion 250 of the interface I.

The first portion 250 of the interface I can include the collar portion 290 attached to and moveably supported by the surgical table 10', and the collar portion 290 includes the receiver portion 300, the locking actuator 302, and the locking bolt 304. As discussed above, the receiver portion 300 is provided on the body portion 296 of the collar portion 290, and the receiver portion 300 includes the recess 306 with the locking bolt 304 being moveable into and out of the recess 306 via actuation of the locking actuator 302. When the end portion 284' is received in the recess 306, actuation of the locking actuator 302 can move the locking bolt 304 into position within the bolt-receiving aperture 286'. And receipt of the locking bolt 304 in the bolt-receiving aperture 286' serves to securely attach the first portion 250 and the second portion 254 of the interface I to one another to moveably interconnect the surgical table 10' and the cart portion 400 with one another.

As described above, although the bolt-receiving aperture 286 'is provided on the end portion 284', and the locking bolt 304' is moveable into and out of the recess 306, the present disclosure is not so limited. Instead, a locking bolt that is similar to locking bolt 304 could be provided on a first modified end portion that is similar to the end portion 284', and be moveable out of and into the first modified end portion. Furthermore, a bolt-receiving aperture that is similar to the bolt-receiving aperture 286' could be provided in a first modified receiver portion and a first modified recess that are similar to the receiver portion 300 and the recess 306. Thus, when the first modified end portion is received in the first modified recess, the locking bolt provided on the first modified end portion can be actuated and moved into the bolt-receiving aperture of the first modified receiver portion to facilitate engagement therebetween and attachment of the first portion 250 and the second portion 254 of the interface I to one another.

Furthermore, although, as described above, the end portion 284' provided on the extension portion 282' is received in the recess 306, the present disclosure is not so limited. Instead, a second modified receiver portion and a second modified recess similar to the receiver portion 300 and the recess 306 could be provided on the extension portions 282', and a second modified end portion similar to the end portion 284' could be provided on the collar portion 290. As such, the second modified end portion provided on the collar portion 290 can be received in the second modified recess of the second modified receiver portion provided on the extension portion 282'. And the locking bolts and bolt-receiving apertures, as described above, whether respectively positioned in/on the second modified receiver portion and the second modified end portion, or vice versa, can be engaged to facilitate engagement therebetween and attachment of the first portion 250 and the second portion 254 of the interface I to one another.

With the first portion 250 and the second portion 254 securely engaged to one another to moveably interconnect the surgical table 10' and the cart portion 400, the actuator 252 can be actuated to facilitate movement of the surgical table 10' and the cart portion 400 relative to one another. Actuation of the actuator 252 facilitates movement of the collar portion 290 and the cross member 30' relative to one another. When the first portion 250 and the second portion 254 are securely engaged to one another, the relative movement, as discussed above, of the collar portion 290 and the cross member 30' facilitates positioning and repositioning the surgical table 10' and the cart portion 400 relative to one another. Such movement correspondingly can be used to adjust the position of the cart portion 400 and the imaging device 402 relative to the patient P supported by the surgical table 10', or vice versa, before, during, and after surgery. Given that the surgical table 10' is heavier than the cart portion 400, actuation of the actuator 252 can serve to move of the cart portion 400 relative to surgical table 10', and such movement can be used to position and reposition the imaging device 402 relative to the patient P.

As discussed above, the base portion 270' supports the imaging device 402 and the first robotic arm 404 thereon. The first robotic arm 404 can be used for positioning and repositioning portions of the imaging device 402. The first robotic arm 404 is supported relative to an upper surface 406 of the base portion 270' by a post portion 408 extending upwardly from the upper surface 406. And the first robotic arm 404 can include a first portion 410, a second portion 412, a third portion 414, a fourth portion 416, a fifth portion 418, a sixth portion 420, an end portion 422 having a mating portion 424. The first portion 410 is rotatable relative to the post portion 408, the second portion 412 is rotatable relative to the first portion 410, the third portion 414 is rotatable relative to the second portion 412, the fourth portion 416 is rotatable relative to the third portion 414, the fifth portion 418 is rotatable relative to the fourth portion 416, the sixth portion 420 is rotatable relative to the fifth portion 418, and the end portion 422 is rotatable relative to the sixth portion 420. And the first robotic arm 404 can include one or more actuators (not shown) to facilitate such rotation.

Such rotational movement, as depicted in FIGS. 27-31, allows the first robotic arm 404 to be manipulated, and such manipulation affords attachment of surgical equipment such as tools and/or attachments to the mating portion 424. For example, the relative rotational movement of the first portion 410, the second portion 412, the third portion 414, the fourth portion 416, the fifth portion 418, the sixth portion 420, and the end portion 422, and the corresponding manipulation of the first robotic arm 404 allows the first robotic arm 404 to be move from a disengaged position (FIG. 25) to an engaged position to afford the mating portion 424 being positioned relative to a storage tray 426 including various tools 428, or positioned (FIG. 27) relative a storage compartment 430 including a radiographic receptor (or receiver) 432 of the imaging device 402. The storage tray 426 (and the various tools 428 stored therein) can be provided on the upper surface 406 of the base portion 270', and the storage compartment 430 (and the radiographic receptor 432 stored thereon) can be provided on a side surface 434 of the base portion 270'. Using the manipulation of the first robotic arm 404, the mating portion 424 can be positioned and repositioned to facilitate attachment of the various tools 428 and/or the radiographic receptor 432 thereto.

After attachment of the surgical equipment (such as the various tools 428 and the radiographic receptor 432) to the mating portion 424, the relative rotational movement of the first portion 410, the second portion 412, the third portion 414, the fourth portion 416, the fifth portion 418, the sixth portion 420, and the end portion 422, and the corresponding manipulation of the first robotic arm 404 allows the surgical equipment to be positioned and repositioned relative to other portions of the cart portion 400, and, when the surgical table 10' and the cart portion 400 are moveably interconnected, to be positioned and repositioned relative to the surgical table 10' and the patient P supported thereby. For example, the various tools 428 can be used to aid and/or perform surgery on the patient P, and the radiographic receptor 432 can be used to receive radiographic energy directed through the patient P before, during, or after surgery.

In addition to the radiographic receptor 432, the imaging device 402 can include a radiographic projector (or emitter) 440 for directing radiographic energy through the patient P to the radiographic receptor 432. The cart portion 400 can include a second robotic arm (or armature) 442 for supporting additional surgical equipment such as tools and/or attachments (including the radiographic projector 440), and manipulation of the second robotic arm 442 allows the additional surgical equipment to be positioned and repositioned relative to other portions of the cart portion 400, and, when the surgical table 10' and the cart portion 400 are moveably interconnected, to be positioned and repositioned relative to the surgical table 10' and the patient P supported thereby. In particular, the second robotic arm 442 can be used to position and reposition the radiographic projector 440 relative to the patient P and the radiographic receptor 432, so that the radiographic energy can be directed from the radiographic projector 440 to the radiographic receptor 432 through the patient P.

As depicted in FIGS. 25-31, the second robotic arm 442 can be moved into and out of a recess 444 formed in a side portion of the base portion 270' of the cart portion 400 from unextended positions (FIGS. 25-27) to various extended positions. The second robotic arm 442 can include a first arm portion 450, a second arm portion 452, an end portion 454, and an actuator 456. The first arm portion 450 can include a first end 460 and a second end 462, and the second arm portion 452 can include a first end 464 and a second end 466. The first end 460 of the first arm portion 450 can be pivotally attached to the cart portion 400 within the recess 444; the second end 462 of the first arm portion 450 can be pivotally attached to the first end 464 of the second arm portion 452; the second end 466 of the second arm portion 452 can be attached to the end portion 454; and the radiographic projector 440 can be rotatably attached to the end portion 454. The end portion 454 could be attached to second arm portion 452 to allow the end portion 454 to swivel about an axis aligned or substantially aligned with the second arm portion 452.

The actuator 456 can extend between the first end 460 of the first arm portion 450, and a portion of the second arm portion 452 between the first end 464 and the second end 466 of the second arm portion 452. A first end 470 of the actuator 456 can be pivotally attached relative to the pivotal attachment of the first end 460 of the first arm portion 450 to the cart portion 400, and a second end 472 of the actuator 456 can be pivotally attached via a clevis connection 474 to the second arm portion 452. Actuation of the actuator 456 can be used to pivot the second arm portion 452 relative to the first arm portion 454. The actuator 456 can be a piston actuator moveable between a first retracted position and a second extended position. When the actuator 456 is in the first retracted position, the end portion 454, via pivotal movement of the second arm portion 452 relative to the first arm portion 450, is positioned adjacent the first arm portion 450. And, when the actuator 456 is in the second retracted position, the end portion 454, via pivotal movement of the second arm portion 452 relative to the first arm portion 450, is positioned away from the first arm portion 450.

Additionally, an actuator (not shown) can be used to pivot the first arm portion 450 relative to the cart portion 400, another actuator (not shown) can be used to rotate the radiographic projector 440 relative to the end portion 454, and yet another actuator (not shown) can be used to swivel the end portion 454 relative to the second arm portion 452. As such, using the actuator 456 for pivoting the second arm portion 452 relative to the first arm portion 450, the actuator for rotating the first arm portion 450 relative to the cart portion 400, the actuator for rotating the radiographic projector 440 relative to the end portion 454, and/or the actuator for swiveling the end portion 454 relative to the second arm portion 452, the radiographic projector 440 can be positioned and repositioned relative to the patient P and the radiographic receptor 432. The first robotic arm 404 and the second robotic arm 442, and the surgical equipment supported thereby can be moved within at least a first two-dimensional plane that extends through the base portion 270'. In doing so, the first robotic arm 404 and the second robotic arm 442 can be moved independently or coordinately in simultaneous or non-simultaneous fashion relative to the patient P and one another. Given the arrangement of the first robotic arm 404 and the second robotic arm 442, as depicted in FIGS. 28-37, the first two-dimensional plane is oriented vertically. If the end portion 454 is configured to swivel relative to the second arm portion 452, then imaging can occur in additional two-dimensional planes angled to relative to vertical. When the cart portion 400 is moveably interconnected with the surgical table 10' via the interface I, the above-described two-dimensional planes (including the first two-dimensional plane) extend transversely to the cranial-caudal axis of the patient P supported by the surgical table 10'. During movement of the cart portion 400 relative to the surgical table 10' using the interface I, the first two-dimensional plane can be moved relative to the patient P in the cranial-caudal directions to afford access to different portions of the patient P, and a three-dimensional operational area thereby can be formed by such movement of the first two-dimensional plane. As such, the first robotic arm 404 and the second robotic arm 442 can be moveable within at least the three-dimensional operational area to access different portions of the patient P by the surgical equipment supported thereby. To illustrate, the use of the interface I to position and reposition the cart portion 400 relative to the surgical table 10' and the patient P increases the areas of the patient P accessible by the various tools 428 attached to the first robotic arm 404 via creation of the three-dimensional operational area, Similarly, the use of the interface I to position and reposition the cart portion 400 relative to the surgical table 10' and the patient P also increases the areas of the patient P accessible by the radiographic receptor 432 and the radiographic projector 440 attachable to the first robotic arm 404 and the second robotic arm 442, respectively, via creation of the three-dimensional operational area.

To facilitate use of the imaging device 402, movement of the robotic arm 404 and the second robotic arm 442 can be coordinated with one another to facilitate positioning and repositioning of the radiographic receptor 432 and the radiographic projector 440, respectively, into alignment with one another in the first two-dimensional plane across different portions of the patient P before, during, and after surgery. As such, the radiographic receptor 432 and the radiographic projector 440 can be moved in concert with one another over different portions of the patient P in the first two-dimensional plane to facilitate imaging of those portions of the patient P. To illustrate, using the manipulation of the first robotic arm 404 and the second robotic arm 442, the radiographic receptor 432 and the radiographic projector 440 can be aligned with one another in the first two-dimensional plane such that radiographic energy can be directed from the radiographic projector 440 to the radiographic receptor 432 horizontally (FIG. 28), vertically (FIG. 29), diagonally (FIGS. 30 and 31), and therebetween.

Figure 32:
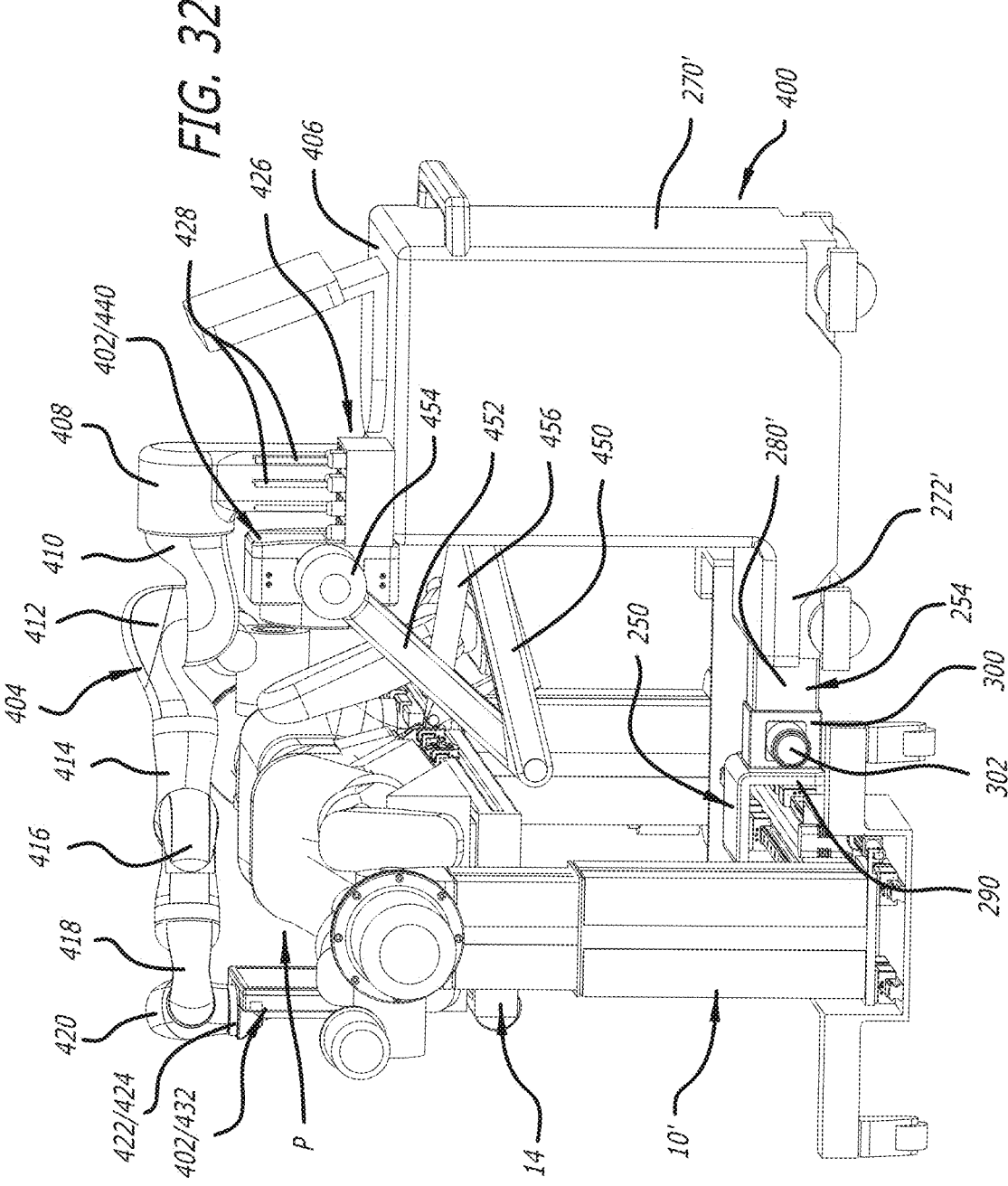
FIG. 32 is a second lateral side, perspective view of the surgical cart of FIG. 25 and an end, perspective view of a surgical table that illustrates the moveable interconnection between the surgical cart and the surgical table via an interface, and illustrates the portions of the imaging system oriented for direction of the radiographic energy horizontally through a patient supported by the surgical table.
Figure 33:
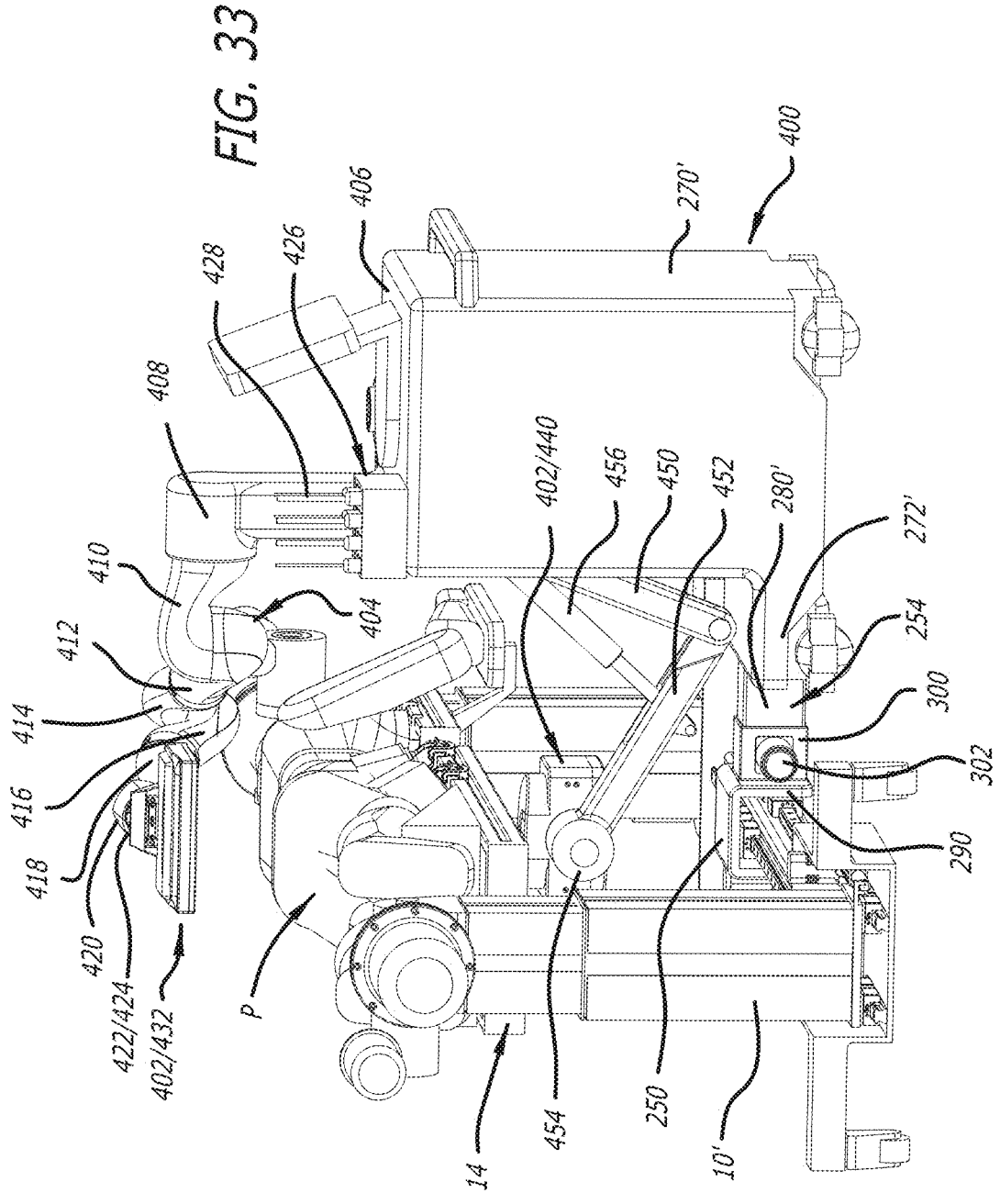
FIG. 33 is a second lateral side, perspective view of the surgical cart of FIG. 25 and an end, perspective view of the surgical table of FIG. 32 interconnected with the surgical cart via the interface that illustrates the portions of the imaging system oriented for the direction of the radiographic energy vertically through the patient supported by the surgical table.
Figure 34:
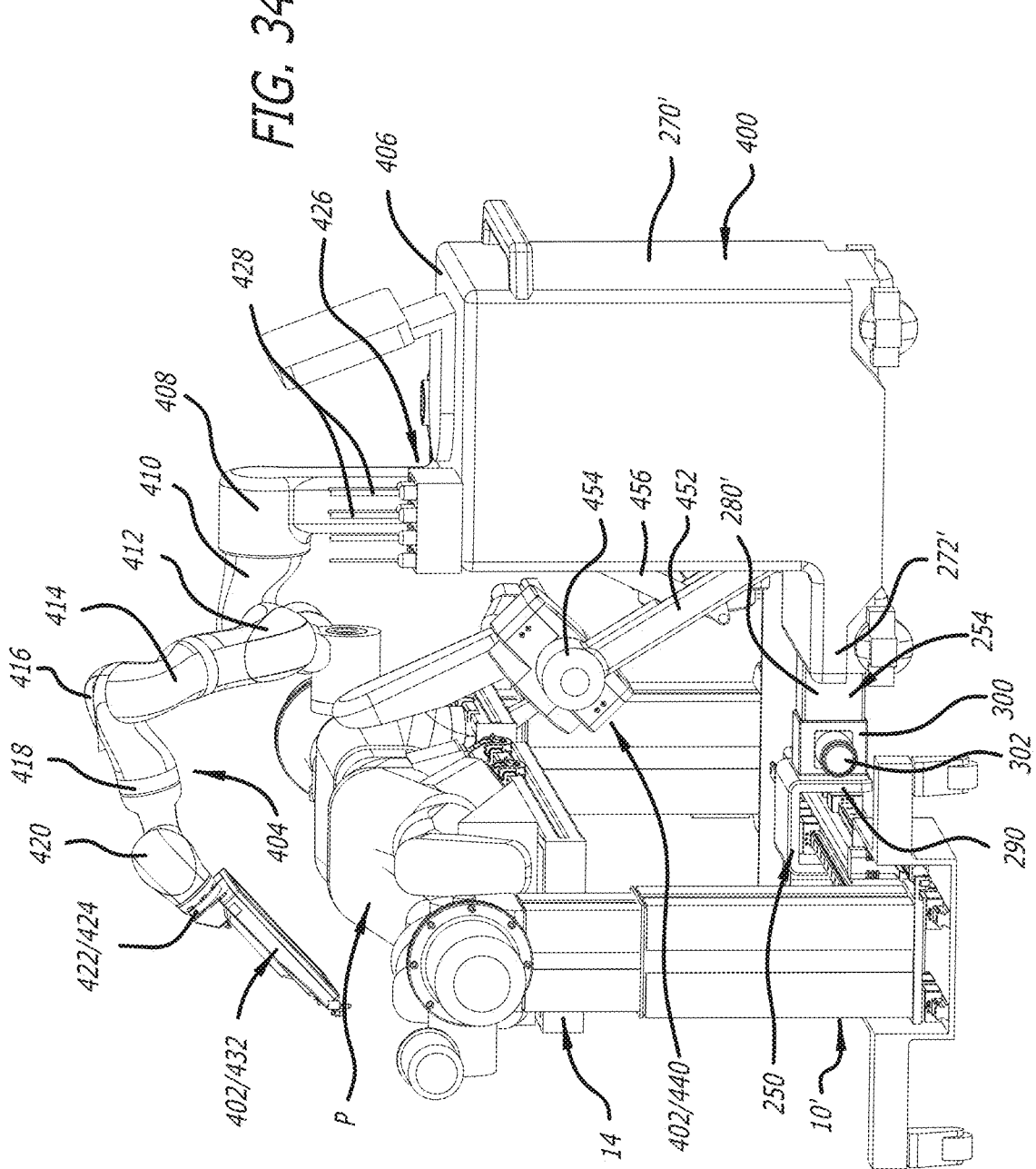
FIG. 34 is a second lateral side, perspective view of the surgical cart of FIG. 25 and an end, perspective view of the surgical table of FIG. 32 interconnected with the surgical cart via the interface that illustrates the portions of the imaging system oriented for the direction of the radiographic energy in the first diagonal direction through the patient supported by the surgical table.
Figure 35:
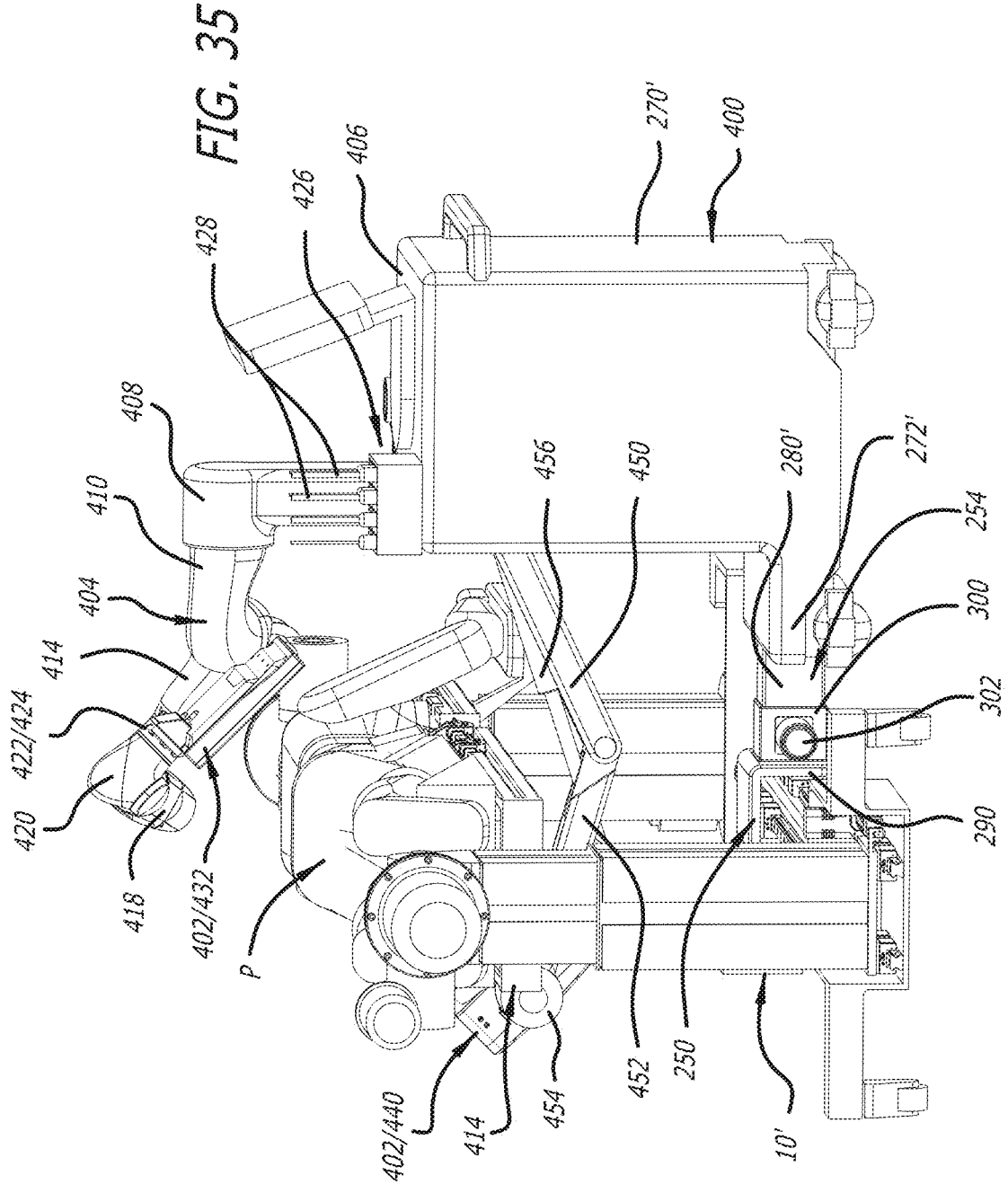
FIG. 35 is a second lateral side, perspective view of the surgical cart of FIG. 25 and an end, perspective view of the surgical table of FIG. 32 interconnected with the surgical cart via the interface that illustrates the portions of the imaging system oriented for the direction of the radiographic energy in the second diagonal direction through the patient supported by the surgical table.
Figure 36:
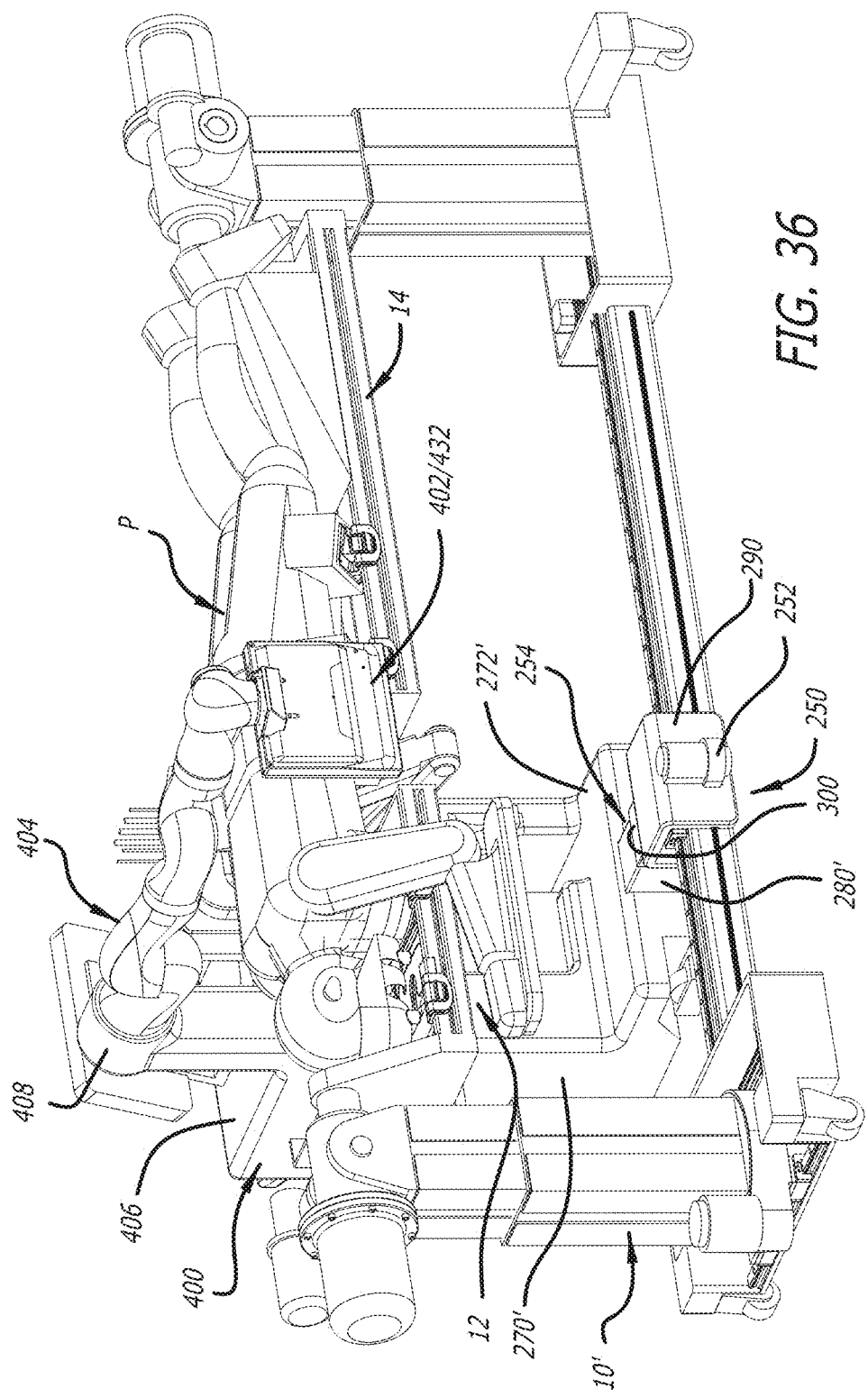
FIG. 36 is a front, perspective view of the surgical cart of FIG. 25 and a side, perspective view of the surgical table of FIG. 32 interconnected with the surgical cart via the interface that illustrates the portions of the imaging system oriented for the direction of the radiographic energy horizontally through the patient supported by the surgical table.
Figure 37:
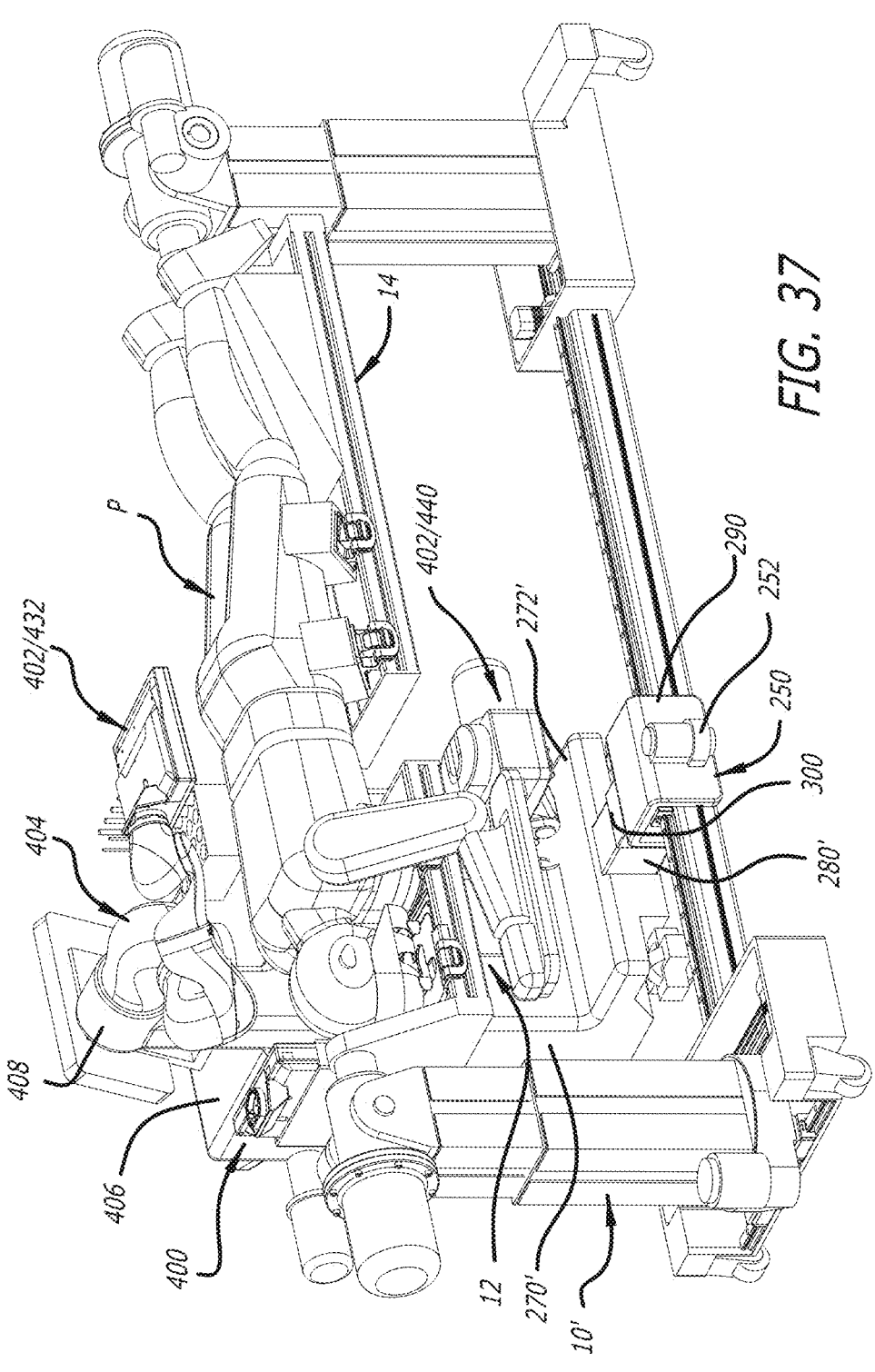
FIG. 37 is a front, perspective view of the surgical cart of FIG. 25 and a side, perspective view of the surgical table of FIG. 32 interconnected with the surgical cart via the interface that illustrates the portions of the imaging system oriented for the direction of the radiographic energy horizontally through the patient supported by the surgical table.

The manipulation of the first robotic arm 404 and the second robotic arm 442, as depicted in FIGS. 32-37, can afford positioning and repositioning of the radiographic receptor 432 and the radiographic projector 440 to provide at least 180° imaging of portions of the patient P in the first two-dimensional plane. As depicted in FIGS. 32-37, the patient P is positioned on the surgical table 10' in the prone position. When the radiographic receptor 432 and the radiographic projector 440 are aligned horizontally, as depicted in FIGS. 32 and 36, 2D imagery from one lateral portion to the other lateral portion of the patient P relative to the first two-dimensional plane can be generated using the imaging device 402. When the radiographic receptor 432 and the radiographic projector 440 are aligned vertically, as depicted in FIGS. 33 and 37, 2D imagery from an anterior portion to a posterior portion of the patient P relative to the first two-dimensional plane can be generated using the imaging device 402. When the radiographic receptor 432 and the radiographic projector 440 are aligned diagonally, as depicted in FIGS. 34 and 35, 2D imagery from a first anterior-lateral portion to an opposite first posterior-lateral portion of the patient P relative to the first two-dimensional plane, and from a second anterior-lateral portion to an opposite second posterior-lateral portion relative to the first two-dimensional plane can be generated using the imaging device 402. Furthermore, the movement of the cart portion 400 relative to the surgical table 10' via actuation of the interface I affords movement of the first two-dimensional plane in the cranial-caudal directions to afford 2D image generation by the imaging device 402 of different portions of the patient P along the cranial-caudal axis.

The manipulation of the first robotic arm 404 and the second robotic arm 442 to position and reposition the radiographic receptor 432 and the radiographic projector 440, in conjunction with rotation of the patient P via rotation of the first platform portion 12 and the second platform portion 14 supporting the patient P thereon, can be used to provide 360° imaging of portions of the patient P in the first two-dimensional plane. For example, the patient P can be rotated from the prone position to the supine position via rotation of the first platform portion 12 and the second platform portion 14, and the images generated using the imaging device 402 would be the reverse as those described above with the patient P in the prone position. While the above-discussed imagery generated using the image device 402 would typically be 2D imagery, continuous manipulation of the first robotic arm 404 and the second robotic arm 442 and/or continuous rotation of the patient P using the first platform portion 12 and the second platform portion 14, in combination continuous use of the radiographic receptor 432 and the radiographic projector 440, can generate 3D imagery around all or portions of the patient P. Additionally, the movement of the cart portion 400 relative to the surgical table 10' via actuation of the interface I affords imaging of various portions of the patient P along the cranial-caudal axis of the patient P supported by the surgical table 10' that can be used to generate other 3D imagery using the imaging device.

During use of the cart portion 400 and the surgical table 10", the patient P can be positioned on the surgical table 10' in a prone position, a supine position, lateral positions, and positions therebetween. Thereafter, the patient P can be articulated and rotated using the surgical table 10', and the cart portion 400 can be moveably interconnected relative to surgical table 10' using the interface I. As depicted in FIGS. 32-37, the patient P is supported by the surgical table 10' in the prone position, and the cart portion 400 is moveably interconnected with the surgical table 10' using the interface I. As discussed above, the actuation of the interface I affords positioning and repositioning of the cart portion 400 in the cranial-caudal directions relative to the surgical table 10' and the patient P supported thereby to move the first robotic arm 404 and the second robotic arm 442 through the above-discussed three-dimensional operational area. As discussed above, the cart portion 400 can be positioned and repositioned using the relative movement before, during, and after manipulation of the first robotic arm 404 and the second robotic arm 442 (and the surgical equipment attached thereto) to afford use of thereof at different portions on the patient P and within corresponding three-dimensional operational area afforded thereby.

The surgical table 10' and the cart portion 400 can include a controller or controllers for controlling actuatable features thereof. To illustrate, when using the surgical table 10', the controller or controllers included therein can control the operation of the slider portion 40 and the actuator 80 thereof; the operation of the rotator portion 42 and the actuator 94 thereof; the operation of the slider portion 100 and the actuator 132 thereof; the operation of the telescoping columns 140; the operation of the motors and transmissions 156 of the rotational portions 154; and the operation of the motors and transmissions 162 of the tilt portions 160.

During use, the controller or controllers, in addition to controlling the actuatable features of the surgical table 10", can control operation of actuatable features including the actuator 252 of the interface I to facilitate movement of the cart portion 400 relative to the gantry; the actuators of the first robotic arm 404 and the second robotic arm 442 to control manipulation thereof; and operation of the attachments/tools (including the radiographic receptor 432 and the radiographic projector 440).

Each or some of the surgical table 10', the cart portion 400, and/or components thereof can include at least one controller for controlling operation of the corresponding actuatable features associated therewith. For example, each of the surgical table 10' and the cart portion 400 can include a controller or controller, and the controllers can communicate with the above-discussed actuatable features and one another to control and coordinate operation with the above-discussed actuatable features. Or, for example, one or more controllers can be included on a single one or multiple ones of the surgical table 10', the cart portion 400, and/or the components thereof, and the controller or controllers can communicate with the above-discussed actuatable features and one another to control and coordinate operation with the above-discussed actuatable features.

As such, the controller or controllers can be used to actuate movement of the actuatable features of the surgical table 10' and the cart portion 400 in coordination and concert with one another to synchronize movement therebetween. Such synchronized movement, for example, can allow the cart portion 400 (and the first robotic arm 404 and the second robotic arm 442) to move relative to the surgical table 10', and the first robotic arm 404 and the second robotic arm 442 with the surgical equipment attached thereto to be moved independently or coordinatedly in simultaneous or non-simultaneous fashion relative to the patient P to aid and/or perform surgery on the patient P before, during, or after the relative movement of the surgical table 10' and the cart portion 400. The controllers can communicate with one another and the actuatable above-discussed features via hardwired and/or wireless connections.

It should be understood that various aspects disclosed herein may be combined in different combinations than the combinations specifically presented in the description and the accompanying drawings. It should also be understood that, depending on the example, certain acts or events of any of the processes of methods described herein may be performed in a different sequence, may be added, merged, or left out altogether (e.g., all described acts or events may not be necessary to carry out the techniques). In addition, while certain aspect of this disclosure are described as being performed by a single module or unit for purposes of clarity, it should be understood that the techniques of this disclosure may be performed by a combination of units or modules associated with, for example, a medical device.

We claim:

1. A combination of a surgical table, a surgical cart supporting at least two surgical robotic arms, and an interface for moveably interconnecting the surgical cart with the surgical table, the combination comprising:

the surgical table comprising a first end, an opposite second end, a longitudinal cross-member extending between the first end and the second end, at least one track attached to the longitudinal cross-member, and at least one patient support portion being configured to rotatably support a patient thereon;

the surgical cart comprising:

a base portion having at least an upper portion and a side portion; and a first surgical robotic arm and a second surgical robotic arm of the at least two surgical robotic arms supported by the base portion, the first surgical robotic arm supported relative to the upper portion, and the second surgical robotic arm supported relative to the side portion, the first surgical robotic arm including at least an end portion, and the second surgical robotic arm including a first arm portion, a second arm portion, and an end portion, the first arm portion and the second arm portion each including a first end and a second end, the first end of the first arm portion being pivotally attached relative to the to the side portion, the second end of the first arm portion and the first end of the second arm portion being pivotally attached to one another, and the second end of the second arm portion supporting the end portion of the second surgical robotic arm, the end portions of the first surgical robotic arm and the second surgical robotic arm each supporting surgical equipment thereon; and the interface comprising:

an extension portion attached relative to the surgical cart, the extension portion including an end portion and a receiving aperture formed in the end portion, and the extension portion being moveable outwardly and inwardly relative to the surgical cart;

a receiver portion provided on the collar portion, the receiver portion including a recess and a locking member moveable into and out of the recess, and the recess being configured to receive the end portion of the extension portion, and the locking member configured to be moved into and out of the receiving aperture;

a collar portion moveably attached relative to the longitudinal cross-member of the surgical table, the collar portion including a first end, an opposite second end, an interior cavity extending between the first end and the second end, an interior surface defining a portion of the interior cavity, and at least one truck attached relative to the interior surface; and an actuator portion actuatable to facilitate movement of the at least one truck along the at least one track;

wherein portions of the longitudinal cross member of the surgical table are received in the interior cavity to attach the collar portion to the surgical table with the at least one truck being engaged to at least one track portion attached to the longitudinal cross member;

wherein, when the end portion of the extension portion is received in the recess, the locking member can be received in the receiving aperture to attach the extension portion and the collar portion to one another, and after attachment of the extension portion and the collar portion, the surgical cart is moveably interconnected to the surgical table via actuation of the actuator portion; and wherein the first surgical robotic arm and the second surgical robotic arm can be manipulated to position and reposition the surgical equipment thereon relative to the patient supported by the surgical table.

2. The combination of claim 1, wherein the surgical equipment supported by the end portions of the first surgical robotic arm and the second surgical robotic arm includes a first portion of an imaging device supported by the end portion of the first surgical robotic arm, and a second portion of the imaging device supported by the end portion of the second surgical robotic arm.

3. The combination of claim 2, wherein, after the surgical cart and the surgical table are moveably interconnected with one another, the first portion and the second portion of the imaging device can be aligned with one another on opposite sides of the patient.

4. The combination of claim 3, wherein the first portion and the second portion of the imaging device can be aligned with one another for directing radiographic energy one of vertically through the patient, horizontally through the patient, and diagonally through the patient.

5. The combination of claim 4, wherein the patient can be rotated on the at least one patient support by the surgical table when the first portion and the second portion of the imaging device are aligned for direction of the radiographic energy vertically, horizontally, and diagonally.

6. The combination of claim 5, wherein the surgical cart can be moved in cranial-caudal directions relative to the patient supported by the at least one patient support via actuation of the actuator portion when the first portion and the second portion of the imaging device are aligned for direction of the radiographic energy vertically, horizontally, and diagonally.

7. The combination of claim 1, wherein the actuator portion is one of attached to the collar portion and attached to and/or supported by the surgical cart, the actuator portion including a first gear portion being configured to operatively engage a second gear portion attached to the longitudinal cross member.

8. The combination of claim 7, wherein the first gear portion is a circular gear and the second gear portion is a linear gear, and wherein rotation of the circular gear in a first rotational direction via actuation of the actuator portion moves the collar portion in a first linear direction relative to the longitudinal cross member, and rotational of the circular gear in an opposite second rotational direction via actuation of actuator portion moves the collar portion in an opposite second linear direction relative to the longitudinal cross member.

9. The combination of claim 8, wherein movement of the collar portion in the first and second linear directions relative to the longitudinal cross member correspondingly moves the surgical cart in the first and second linear directions relative to the surgical table to afford positioning and repositioning of the first surgical robotic arm and the second robotic surgical arm relative to the patient in corresponding cranial-caudal directions.

10. A combination of a surgical table, a surgical cart supporting at least two surgical robotic arms, and an interface for moveably interconnecting the surgical cart with the surgical table, the combination comprising:

the surgical table comprising a first end, an opposite second end, a longitudinal cross-member extending between the first end and the second end, and at least one patient support portion being configured to support a patient thereon;

the surgical cart comprising:

a base portion; and a first surgical robotic arm and a second surgical robotic arm of the at least two surgical robotic arms supported by the base portion, the first surgical robotic arm including at least an end portion, and the second surgical robotic arm including a first arm portion, a second arm portion, and an end portion, the first arm portion and the second arm portion each including a first end and a second end, the first end of the first arm portion being pivotally attached relative to the to the side portion, the second end of the first arm portion and the first end of the second arm portion being pivotally attached to one another, and the second end of the second arm portion supporting the end portion of the second surgical robotic arm, the end portions of the first surgical robotic arm and the second surgical robotic arm each supporting surgical equipment thereon; and the interface comprising:

an extension portion attached relative to the surgical cart, the extension portion including an end portion and a receiving aperture formed in the end portion;

a collar portion moveably attached relative to the longitudinal cross-member of the surgical table, the collar portion including a first end, an opposite second end, an interior cavity extending between the first end and the second end, an interior surface defining a portion of the interior cavity;

a receiver portion provided on the collar portion, the receiver portion including a recess and a locking member moveable into and out of the recess, and the recess being configured to receive the end portion of the extension portion, and the locking member configured to be moved into and out of the receiving aperture; and an actuator portion actuatable to facilitate movement of the collar portion relative to the longitudinal cross member;

wherein portions of the longitudinal cross member of the surgical table are received in the interior cavity to attach the collar portion to the surgical table;

wherein, when the end portion of the extension portion is received in the recess, the locking member can be received in the receiving aperture to attach the extension portion and the collar portion to one another, and after attachment of the extension portion and the collar portion, the surgical cart is moveably interconnected to the surgical table via actuation of the actuator portion; and wherein the first surgical robotic arm and the second surgical robotic arm can be manipulated to position and reposition the surgical equipment thereon relative to the patient supported by the surgical table.

11. The combination of claim 10, wherein the surgical equipment supported by the end portions of the first surgical robotic arm and the second surgical robotic arm includes a first portion of an imaging device supported by the end portion of the first surgical robotic arm, and a second portion of the imaging device supported by the end portion of the second surgical robotic arm.

12. The combination of claim 11, wherein, after the surgical cart and the surgical table are moveably interconnected with one another, the first portion and the second portion of the imaging device can be aligned with one another on opposite sides of the patient.

13. The combination of claim 12, wherein the first portion and the second portion of the imaging device can be aligned with one another for directing radiographic energy one of vertically through the patient, horizontally through the patient, and diagonally through the patient.

14. The combination of claim 13, wherein the patient can be rotated on the at least one patient support by the surgical table when the first portion and the second portion of the imaging device are aligned for direction of the radiographic energy vertically, horizontally, and diagonally.

15. The combination of claim 14, wherein the surgical cart can be moved in cranial-caudal directions relative to the patient supported by the at least one patient support via actuation of the actuator portion when the first portion and the second portion of the imaging device are aligned for direction of the radiographic energy vertically, horizontally, and diagonally.

16. A combination of a surgical table, a surgical cart supporting at least two surgical robotic arms, and an interface for moveably interconnecting the surgical cart with the surgical table, the combination comprising:

the surgical table comprising a first end, an opposite second end, a longitudinal cross-member extending between the first end and the second end, and at least one patient support portion being configured to support a patient thereon;

the surgical cart comprising:

a base portion; and a first surgical robotic arm and a second surgical robotic arm of the at least two surgical robotic arms supported by the base portion, the first surgical robotic arm including at least an end portion, and the second surgical robotic arm including a first arm portion, a second arm portion, and an end portion, the first arm portion and the second arm portion each including a first end and a second end, the first end of the first arm portion being pivotally attached relative to the to the side portion, the second end of the first arm portion and the first end of the second arm portion being pivotally attached to one another, and the second end of the second arm portion supporting the end portion of the second surgical robotic arm, the end portions of the first surgical robotic arm and the second surgical robotic arm each supporting surgical equipment thereon; and the interface comprising:

an extension portion attached relative to the surgical cart, the extension portion including an end portion and a receiving aperture formed in the end portion;

a collar portion moveably attached relative to the longitudinal cross-member of the surgical table;

a receiver portion provided on the collar portion, the receiver portion including a recess and a locking member moveable into and out of the recess, and the recess being configured to receive the end portion of the extension portion, and the locking member configured to be moved into and out of the receiving aperture; and an actuator portion actuatable to facilitate movement of the collar portion relative to the longitudinal cross member;

wherein, when the end portion of the extension portion is received in the recess, the locking member can be received in the receiving aperture to attach the extension portion and the collar portion to one another, and after attachment of the extension portion and the collar portion, the surgical cart is moveably interconnected to the surgical table via actuation of the actuator portion; and wherein the first surgical robotic arm and the second surgical robotic arm can be manipulated to position and reposition the surgical equipment thereon relative to the patient supported by the surgical table.

17. The combination of claim 16, wherein the surgical equipment supported by the end portions of the first surgical robotic arm and the second surgical robotic arm includes a first portion of an imaging device supported by the end portion of the first surgical robotic arm, and a second portion of the imaging device supported by the end portion of the second surgical robotic arm.

18. The combination of claim 17, wherein, after the surgical cart and the surgical table are moveably interconnected with the another, the first portion and the second portion of the imaging device can be aligned with one another for directing radiographic energy one of vertically through the patient supported by the at least one patient support portion, horizontally through the patient supported by the at least one patient support portion, and diagonally through the patient supported by the at least one patient support portion.

19. The combination of claim 18, wherein the patient can be rotated on the at least one patient support by the surgical table when the first portion and the second portion of the imaging device are aligned for direction of the radiographic energy vertically, horizontally, and diagonally.

20. The combination of claim 19, wherein the surgical cart can be moved in cranial-caudal directions relative to the patient supported by the at least one patient support via actuation of the actuator portion when the first portion and the second portion of the imaging device are aligned for direction of the radiographic energy vertically, horizontally, and diagonally.

* * * * *